(12) United States Patent
Bansal

(10) Patent No.: US 8,435,512 B2
(45) Date of Patent: May 7, 2013

(54) ANTI-PROPERDIN ANTIBODIES

(75) Inventor: Rekha Bansal, Twinsburg, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 72 days.

(21) Appl. No.: 12/920,997

(22) PCT Filed: Jun. 27, 2008

(86) PCT No.: PCT/US2008/068530
§ 371 (c)(1),
(2), (4) Date: Sep. 3, 2010

(87) PCT Pub. No.: WO2009/110918
PCT Pub. Date: Sep. 11, 2009

(65) Prior Publication Data
US 2011/0008340 A1    Jan. 13, 2011

Related U.S. Application Data

(60) Provisional application No. 61/033,127, filed on Mar. 3, 2008.

(51) Int. Cl.
*A61K 39/395* (2006.01)
*A61K 39/00* (2006.01)

(52) U.S. Cl.
USPC ............... 424/130.1; 424/132.1; 424/133.1; 424/139.1; 424/140.1; 424/141.1

(58) Field of Classification Search .................. None
See application file for complete search history.

(56) References Cited

U.S. PATENT DOCUMENTS

| | | |
|---|---|---|
| 6,333,034 B1 | 12/2001 | Gupta-Bansal et al. |
| 2006/0093599 A1 | 5/2006 | Gazit-Bornstein |
| 2006/0292141 A1* | 12/2006 | Holers et al. ............... 424/144.1 |
| 2010/0263061 A1 | 10/2010 | Song |

\* cited by examiner

*Primary Examiner* — Daniel E Kolker
*Assistant Examiner* — James Rogers
(74) *Attorney, Agent, or Firm* — Tarolli, Sundheim, Covell & Tummino LLP

(57) ABSTRACT

A method of inhibiting alternative complement pathway activation in a mammal includes administering an amount of an antibody and/or fragment thereof that specifically binds to an epitope of the N terminus end of properdin effective to the inhibit alternative complement pathway in the subject.

22 Claims, 44 Drawing Sheets

Properdin – Antibody Model
Ratio 1:1

Peptide⁷¹⁻¹¹⁰ (g lcqpCRSPRW SLWStwapcs vtcsegsqlRYRRCVGWNGq)
Inhibits Alternative Pathway Dependent rRBC Hemolysis $IC_{50} = 115 \pm 2.1 \mu M$ Peptide⁷¹⁻¹¹⁰, uM

Fig. 9

ANTI-PROPERDIN ANTIBODIES

RELATED APPLICATION

This application corresponds to PCT/US2008/68530, filed Jun. 27, 2008, which claims the benefit of U.S. Provisional Application No. 61/033,127, filed Mar. 3, 2008, the subject matter, which is herein incorporated by reference in its entirety.

FIELD OF THE INVENTION

The present invention relates to antibodies specific to properdin and to the use of such antibodies to inhibit alternative complement pathway function in a mammal.

BACKGROUND OF THE INVENTION

The complement system is responsible for initiating and amplifying the inflammatory response to microbial infection and other acute insults. Inappropriate activation of complement has been implicated in pathological situations. For instance, the complement system has been implicated in contributing to the pathogenesis of several acute and chronic conditions, including atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

Complement can be activated through three distinct enzymatic cascades, referred to as the "classical", "Lectin/MBL", and "alternative" pathways (CP, MBL, and AP respectively). These pathways are shown schematically in FIG. 1. The CP is usually triggered by antibody bound to a foreign pathogen. Thus, this pathway requires prior exposure to that pathogen for the generation of specific antibodies. There are three plasma proteins specifically involved in the CP: C1, C2, and C4. MBL is a variation of CP, and is activated by the presence Lectin/MASP-2 but the cascade is similar to the CP.

In contrast to the CP and MBL, the AP is spontaneously triggered by foreign surfaces (e.g., bacteria, yeast, damaged tissue) or other abnormal surfaces, such as the artificial surfaces of medical devices (e.g., the surface of a machine where blood is circulated). There are three plasma proteins specific to the AP: factors B, D, and P (properdin). All three pathways converge at C3 and share C3 to C5-9 proteins that are involved in the later stages of the activation cascades. Anaphylatoxins C3a and C5a are produced because of complement activation. The terminal complement complex known as C5b-9, also known as the membrane attack complex (MAC), is the terminal product of the pathway.

FIG. 2 illustrates a schematic of AP activation. As a result of C3 tick over, C3b is generated. In the schematic, assumption has been made that tick-over of C3 and cleavage of C3 generates the same activated C3b with the released C3a. Activated C3b binds properdin oligomers present in blood to generated (P)n (C3b)n complex. Factor B having higher affinity to properdin bound C3b makes the complex PC3bB, which is then cleaved by factor D to generate PC3bBb. This active convertase cleaves additional C3 to make C3b and release C3a. The same C3 convertase with additional C3b molecules forms C5 convertase. The C5 convertase or C3 convertase cleave C5 to make C5b and C5a. The C5b molecule inserts into the lipid bilayer and forms the nucleus for MAC deposition.

It is well accepted that the alternative pathway serves as the amplification loop of all three pathways. To block the amplification loop function, antibodies to all three AP specific proteins have been developed and tested. Factor P monoclonal antibodies have been developed that inhibit both complement pathways. Anti-factor D and B antibodies have also been developed. While anti-properdin monoclonal antibodies have been developed, these monoclonal antibodies inhibit both the classical pathway and the alternative pathway (U.S. Pat. No. 6,333,034).

Polyclonal antibodies developed against TSR5 show that TSR5 is involved in C3b binding and AP activation (Perdikoulis, M. V., U. Kishore, and K. B. Reid, *Expression and characterisation of the thrombospondin type I repeats of human properdin*, Biochim Biophys Acta, 2001. 1548(2): p. 265-77). While the inhibition of P binding and AP hemolysis was only 40-50%, these authors suggested that TSR5 is important for properdin function. As a comparison, polyclonal antibodies to TSR1 and TSR2 demonstrated lack of inhibition in both assays. This publication teaches that TSR1 and TSR2 are functionally not active.

A more recent study teaches that total inhibition of properdin binding to C3b is required for inhibition of the C3a, C5a, and MAC (U.S. Pat. No. 6,333,034). This invention teaches that such antibodies will inhibit the classical complement pathway directly by inhibiting the classical pathway C3 convertase activity. While the patent teaches use of extracorporeal circulation as a model system with whole human blood, these studies do not teach the effect of anti-properdin monoclonal antibodies on monocyte and platelet activation. Activated monocytes are known to release TNF and form conjugates with platelets. The invention does not teach whether anti-properdin monoclonal antibodies will inhibit activation of monocytes and platelets. One would predict that inhibition of anaphylatoxin formation should have positive effects on inhibition of cellular activation; however, it is possible that such antibodies will activate cells via non-specific mechanisms.

U.S. Patent Application Pub. No. 2006/0093599 teaches that inhibition of properdin binding to C3b is not essential for inhibition of C3b and C5b-9 formation. In the patent application, fully human monoclonal antibodies were used that inhibited properdin binding to C3b and inhibited C3a, C5a, and C5b-9 production in whole blood. Unfortunately, these fully human monoclonal antibodies activated platelets, caused leukocyte platelet aggregate formation, and aggregated properdin monomers into higher oligomeric structures rendering such antibodies useless for therapeutic applications. The patent application provides no evidence/data that supports the fully human monoclonal antibody inhibits oligomerization of the properdin monomer. Blood is known to contain dimmers, trimers and tetramers of properdin. No monomers have been reported. It is unclear how the fully human monoclonal of U.S. Patent Application Pub. No. 2006/0093599 prevents the oligomerization of properdin monomer. The invention appears to be hypothetical and not founded on facts. Moreover, it was observed that the monoclonal antibody of U.S. Patent Application Pub. No. 2006/0093599 actually enhanced oligomer formation possibly explaining the observed platelet activation observed in extracorporeal circulation.

SUMMARY OF THE INVENTION

The present invention relates to a method of inhibiting alternative complement pathway activation in a mammal. The method includes administering to the mammal a therapeutically effective amount of an antibody that specifically binds to an epitope of SEQ ID NO: 2 to inhibit alternative complement pathway in the mammal without affecting classical pathway activation in the mammal. The ratio of binding of the antibody to properdin can be about 0.5:1 to about 1.5:1 (e.g., about 1:1).

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The antibody can be produced in a cell, mammal, genetically engineered mammal, or by phage display.

The administration of the antibody or fragment thereof to the subject can result in at least one of the following: properdin (monomer/oligomer) binding to C3b is inhibited, the formation of C3bB is reduced, C3 convertase formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, TNF is reduced, neutrophil elastase is reduced. The antibody or fragment thereof can also inhibit alternative pathway dependent rabbit erythrocyte lysis in human serum/plasma.

The antibody can be administered in vivo or ex vivo. The antibody can lack the ability to activate Fcγ receptors as well as lack immunogenicity in a human.

Another aspect of the invention relates to a method of inhibiting alternative complement pathway activation in a mammalian host that includes administering to the host a therapeutically effective amount of an anti-properdin monoclonal antibody that specifically binds to an epitope of SEQ ID NO: 2 of properdin.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The administration of the antibody or fragment thereof to the subject can result in at least one of the following: properdin (monomer/oligomer) binding to C3b is inhibited, the formation of C3bB is reduced, C3 convertase formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, TNF is reduced, neutrophil elastase is reduced. The antibody or fragment thereof can also inhibit alternative pathway dependent rabbit erythrocyte lysis in human serum/plasma.

The antibody can be administered in vivo or ex vivo. The antibody can lack the ability to activate Fcγ receptors as well as lack immunogenicity in a human.

A further aspect of the invention relates to a method of inhibiting alternative complement pathway activation in a mammal that includes administering to the mammal an amount of an antibody that specifically binds to properdin in the N terminal region and inhibits both, properdin oligomer formation and properdin binding to C3bB complex without affecting the classical pathway activation in the mammal. The properdin oligomers can contain two to five properdin monomers. The antibody binding to properdin monomer can prevent binding of additional properdin monomers to the properdin oligomers.

The antibody can specifically bind to an epitope on the properdin monomer at its N terminal end. The epitope can comprise a portion of SEQ ID NO: 2, SEQ ID NO: 3, SEQ ID NO: 4 or SEQ ID NO: 5.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

Another aspect of the invention relates to a method of inhibiting alternative complement pathway activation without inhibiting the classical pathway activation in a mammal. The method includes administering to the mammal a therapeutically effective amount of an antibody that specifically binds to an epitope of properdin that blocks the alternative pathway activation without affecting the classical pathway activation. The antibody can inhibit properdin binding to additional properdin monomers. The antibody can also reduce the level of free properdin in a mammal.

The antibody can specifically bind to an epitope on the properdin monomer at its N terminal end. The epitope can comprise a portion of SEQ ID NO: 2, SEQ ID NO: 3, SEQ ID NO: 4, or SEQ ID NO: 5.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The administration of the antibody or fragment thereof to the subject can result in at least one of the following: properdin (monomer/oligomer) binding to C3b is inhibited, the formation of C3bB is reduced, C3 convertase formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, TNF is reduced, neutrophil elastase is reduced. The antibody or fragment thereof can also inhibit alternative pathway dependent rabbit erythrocyte lysis in human serum/plasma.

Another aspect of the invention relates to a method of treating a subject. The method includes passing circulating blood from a blood vessel of the subject, through a conduit, and back to a blood vessel of the subject. The conduit has a luminal surface that includes a material capable of causing at least one of complement activation, platelet activation, leukocyte activation, or platelet-leukocyte adhesion in the subject's blood. A monoclonal antibody is introduced into the subject's bloodstream in an amount effective to reduce at least one of the following: complement activation, platelet activation, leukocyte activation, or platelet-leukocyte adhesion resulting from passage of the circulating blood through the conduit. The passing of blood through the conduit can occur before and/or during and/or after introducing the monoclonal antibody into the subject's bloodstream. The monoclonal antibody can reduce the alternative pathway-dependent formation of C5b-9 and does not reduce the classical pathway-dependent formation of C5b-9. The monoclonal antibody can also reduce at least one of alternative pathway-dependent conversion of factor B into Bb, formation of C3a, C5a and C3b, or alternative pathway-dependent leukocyte, and platelet activation.

In an aspect of the invention, the medical procedure can be an extracorporeal circulation procedure, such as a cardiopulmonary bypass procedure. The antibody can lack the ability to activate Fcγ receptors as well as lack immunogenicity in a human.

The antibody can specifically bind to an epitope on the properdin monomer at its N terminal end of properdin sequence. The epitope can comprise a portion of SEQ ID NO: 2, SEQ ID NO: 3, SEQ ID NO: 4, or SEQ ID NO: 5.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The present invention further relates to a method of treating alternative pathway activation mediated by disease-related or pathological conditions. The method includes administering to the mammal a therapeutically effective amount of an antibody or fragment thereof that specifically binds to an epitope of properdin that blocks the alternative pathway activation without affecting the classical pathway activation.

The antibody can specifically bind to an epitope on the properdin monomer at its N terminal end. The epitope can comprise a portion of SEQ ID NO: 2, SEQ ID NO: 3, SEQ ID NO: 4, or SEQ ID NO: 5.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The disease or condition can be selected from the group consisting of post-cardiopulmonary bypass inflammation, cardiopulmonary bypass, percutaneous coronary intervention (PTCA), ischemia-reperfusion following acute myocardial infarction, myocardial infarction, atherosclerosis, hemodialysis, leukopheresis, plasmapheresis, heparin-induced extracorporeal membrane oxygenation LDL precipitation, extracorporeal membrane oxygenation, multiple organ failure, rheumatoid arthritis, macular degeneration, acute respiratory distress syndrome, asthma, chronic obstructive pulmonary disease, transfusion-related acute lung injury, acute lung injury, transplant rejection, cardiac Surgery, spontaneous abortion, transplant rejection, xeno transplantation, Henoch-Schonlein purpura nephritis, immune complex vasculitis, arteritis, aneurysm, stroke, cardiomyopathy, hemorrhagic shock, crush injury, hypovolemic shock and intestinal ischemia, neuronal injury, spinal cord injury, myasthenia gravis, Huntington's disease, amyotrophic lateral sclerosis, multiple sclerosis, Guillain Barre syndrome, Parkinson's disease, Alzheimer's disease, Goodpasture's disease, septic shock, burn injury, systemic lupus erythematosus, membranous nephritis, Berger's disease, psoriasis, pemphigoid, dermatomyositis, anti-phospholipid syndrome, inflammatory bowel disease, and combinations thereof.

Another aspect of the invention relates to a method of making a rat or mouse anti-properdin monoclonal antibodies in properdin knockout mice/rodent. The method includes administering to the properdin knockout an effective amount of the properdin or fragment thereof that causes the knockout rodent to produce antibodies against properdin. The mouse or rat can include human immunoglobulin genes. The fragment includes a peptide having an amino acid sequence of at least one of SEQ ID NO: 2, SEQ ID NO: 3, SEQ ID NO: 4, or SEQ ID NO: 5.

The present invention also relates to an isolated antibody or antigen binding portion thereof that binds to human properdin. The antibody or antigen binding portion thereof comprises a heavy chain variable domain that includes the amino acid sequences of the three CDRs in SEQ ID NO: 7 and a light chain variable domain that includes the amino acid sequences of the three CDRs in SEQ ID NO: 8.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The ratio of antibody binding to properdin can be about 0.5:1 to about 1.5:1. The antibody can exhibit at least one of the following functional properties: the antibody inhibits oligomeric properdin binding to C3b, the antibody reduces the formation of C3bB, the antibody reduces the formation of C3 convertase, the antibody reduces the production of C3a and C5a, the antibody reduces C5b-9 complex formation, the antibody reduces the activation of neutrophils, the antibody reduces the activation of monocytes, the antibody reduces the activation of platelets, or the antibody reduces the formation of leukocyte-platelet conjugates. The antibody reduced the formation of TNF and elastase. The antibody or antigen binding fragment thereof can also inhibit alternative pathway dependent rabbit erythrocyte lysis in human serum/plasma. The antibody or antigen binding fragment thereof can specifically bind to oligomeric properdin to inhibit alternative pathway complement activation at a molar ratio of antibody to properdin of about 0.5:1, 1:1, to 1.5:1.

In another aspect, the antibody can specifically bind to an epitope on oligomeric properdin at its N terminal end of the properdin amino acid sequence, the epitope comprising at least a portion of the amino acid sequence of SEQ ID NO: 2, SEQ ID NO: 3, SEQ ID NO: 4, or SEQ ID NO: 5. The antibody or antigen binding fragment can also specifically bind to properdin oligomers and promote dissociation of the properdin oligomers to properdin monomers.

In yet another aspect, the heavy chain variable regions CDR1, CDR2, and CDR3 can comprise the amino acid sequences of SEQ ID NO: 9, 10, and 11, respectively. The light chain variable regions CDR1, CDR2, and CDR3 can comprise the amino acid sequences of SEQ ID NO: 12, 13, and 14, respectively.

In a further aspect, the antibody or antigen binding fragment thereof can comprise the heavy chain variable regions and the light chain variable regions of an antibody produced by the hybridoma cell line deposited under ATCC Accession Number PTA-9019 and human constant regions.

The present invention further relates to an isolated antibody or antigen binding portion thereof that binds to human properdin. The antibody or antigen binding fragment thereof comprises a heavy chain variable domain comprising the amino acid sequences of the three CDRs in SEQ ID NO: 7.

The present invention further relates to an isolated antibody or antigen binding portion thereof that binds to human properdin. The antibody or antigen binding fragment thereof comprises a light chain variable domain comprising the amino acid sequences of the three CDRs in SEQ ID NO: 8.

The present invention still further relates to an isolated antibody or antigen binding portion thereof that specifically binds to properdin oligomers. The antibody promotes dissociation of properdin oligomers to properdin monomers.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The ratio of antibody binding to properdin is about 0.5:1 to about 1.5:1. The antibody can exhibit at least one of the following functional properties: the antibody inhibits oligomeric properdin binding to C3b, the antibody reduces the formation of C3bB, the antibody reduces the formation of C3 convertase, the antibody reduces the production of C3a and C5a, the antibody reduces C5b-9 complex formation, the antibody reduces the activation of neutrophils, the antibody reduces the activation of monocytes, the antibody reduces the activation of platelets, or the antibody reduces the formation of leukocyte-platelet conjugates. The antibody inhibits TNF and elastase formation.

The antibody or antigen binding fragment thereof can also inhibit alternative pathway dependent rabbit erythrocyte lysis in human serum/plasma. The antibody or antigen binding fragment thereof can specifically bind to oligomeric properdin to inhibit alternative pathway complement activation at a molar ratio of antibody to properdin of about 1:1.

The present invention still further relates to a method of inhibiting alternative pathway complement activation in a mammal. The method includes administering to the mammal a therapeutically effective amount of an antibody or antigen binding portion thereof that specifically binds to properdin oligomers to inhibit alternative pathway complement activation at a molar ratio of antibody to properdin monomer of about 1:1.

In an aspect of the invention, the antibody can be administered in vivo or ex vivo. The antibody or antigen binding portion thereof can specifically bind to an epitope of SEQ ID NO: 2 to the inhibit alternative complement pathway in the mammal.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

In another aspect, the antibody can be produced by the hybridoma cell line deposited under ATCC Accession Number PTA-9019.

In a further aspect, the antibody or antigen binding portion thereof can bind to the same epitope on properdin as an antibody produced by the hybridoma cell line deposited under ATCC Accession Number PTA-9019.

In a still further aspect, the antibody or antigen binding portion thereof comprises the murine variable regions of an antibody produced by the hybridoma cell line deposited under ATCC Accession Number PTA-9019 and human constant regions.

The present invention still further relates to a method of ameliorating a disease or condition associated with excessive or uncontrolled alternative pathway complement activation. The method includes administering to the mammal a therapeutically effective amount of an antibody or antigen binding portion thereof that specifically binds to properdin to inhibit alternative pathway complement activation at a molar ratio of antibody to Factor P of about 1:1.

In an aspect of the invention, the antibody can be administered in vivo or ex vivo. The antibody or antigen binding portion thereof can specifically bind to an epitope of SEQ ID NO: 2 to the inhibit alternative complement pathway in the mammal.

The antibody can be a monoclonal, polyclonal, chimeric, recombinant, humanized, de-immunized, or fully human antibody. The antibody can also be an antibody fragment, such as a single chain antibody, IgG, $F(ab)_2$, F(ab) fragment, or truncated antibody (e.g., Fc truncated antibody).

In another aspect the antibody can be produced by the hybridoma cell line deposited under ATCC Accession Number PTA-9019.

In a further aspect, the antibody or antigen binding portion thereof can bind to the same epitope on properdin as an antibody produced by the hybridoma cell line deposited under ATCC Accession Number PTA-9019.

In a still further aspect, the antibody or antigen binding portion thereof comprises the murine variable regions of an antibody produced by the hybridoma cell line deposited under ATCC Accession Number PTA-9019 and human constant regions.

Another aspect of the invention relates to a method of inhibiting method of inhibiting alternative complement pathway mediated hemolysis without affecting classical pathway mediated hemolysis in a mammal. The method includes administering to the mammal a therapeutically effective amount of an antibody that specifically binds to an epitope of properdin that blocks the alternative pathway activation without affecting the classical pathway activation. The antibody can inhibit properdin binding to additional properdin monomers. The antibody can also reduce the level of free properdin in a mammal.

The antibody can specifically bind to an epitope on the properdin monomer at its N terminal end. The epitope can comprise a portion of SEQ ID NO: 2, SEQ ID NO: 3, SEQ ID NO: 4, or SEQ ID NO: 5.

The antibody can be a monoclonal, polyclonal, chimeric, recombinant, humanized, de-immunized, or fully human antibody. The antibody can also be an antibody fragment, such as a single chain antibody, IgG, F(ab)2, F(ab')2, F(ab), F(ab') fragment, or truncated antibody (e.g., Fc truncated antibody).

The administration of the antibody or fragment thereof to the subject can result in at least one of the following: properdin (monomer/oligomer) binding to C3b is inhibited, the formation of C3bB is reduced, C3 convertase formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, TNF is reduced, neutrophil elastase is reduced. The antibody or fragment thereof can also inhibit alternative pathway dependent rabbit erythrocyte lysis in human serum/plasma.

BRIEF DESCRIPTION OF THE DRAWINGS

FIG. 9 shows the inhibition of alternative pathway dependent hemolysis of rabbit erythrocytes by the large peptide (71-110) covering both sequences CRSPRWSLWS (SEQ ID NO: 4) and RYRRCVGWNG (SEQ ID NO: 5). Hemolysis assay is a cellular assay for measuring C5b-9 formation. The line marked with filled circles represents the inhibition of hemolysis with greater than 70% inhibition occurring at 100 µM concentration.

FIG. 27 demonstrates dose dependent inhibition of C3a formation with complete inhibition observed at ~10 µg/ml.

FIG. 28 demonstrates that MoAb$^{71-110}$ inhibits C5a formation dose dependently with complete inhibition observed at ~10 μg/ml.

DETAILED DESCRIPTION

Figure 1:
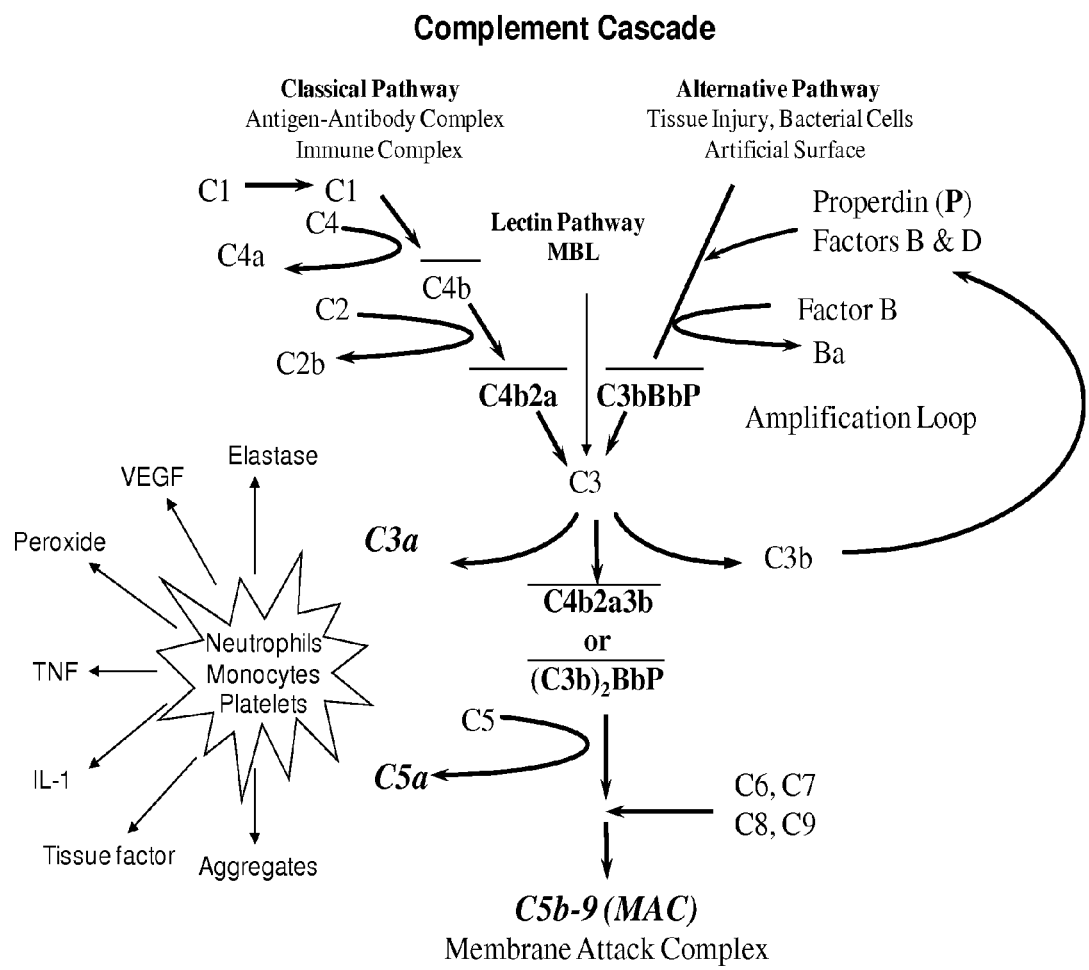
FIG. 1 illustrates the three complement pathways of complement.
Figure 2:
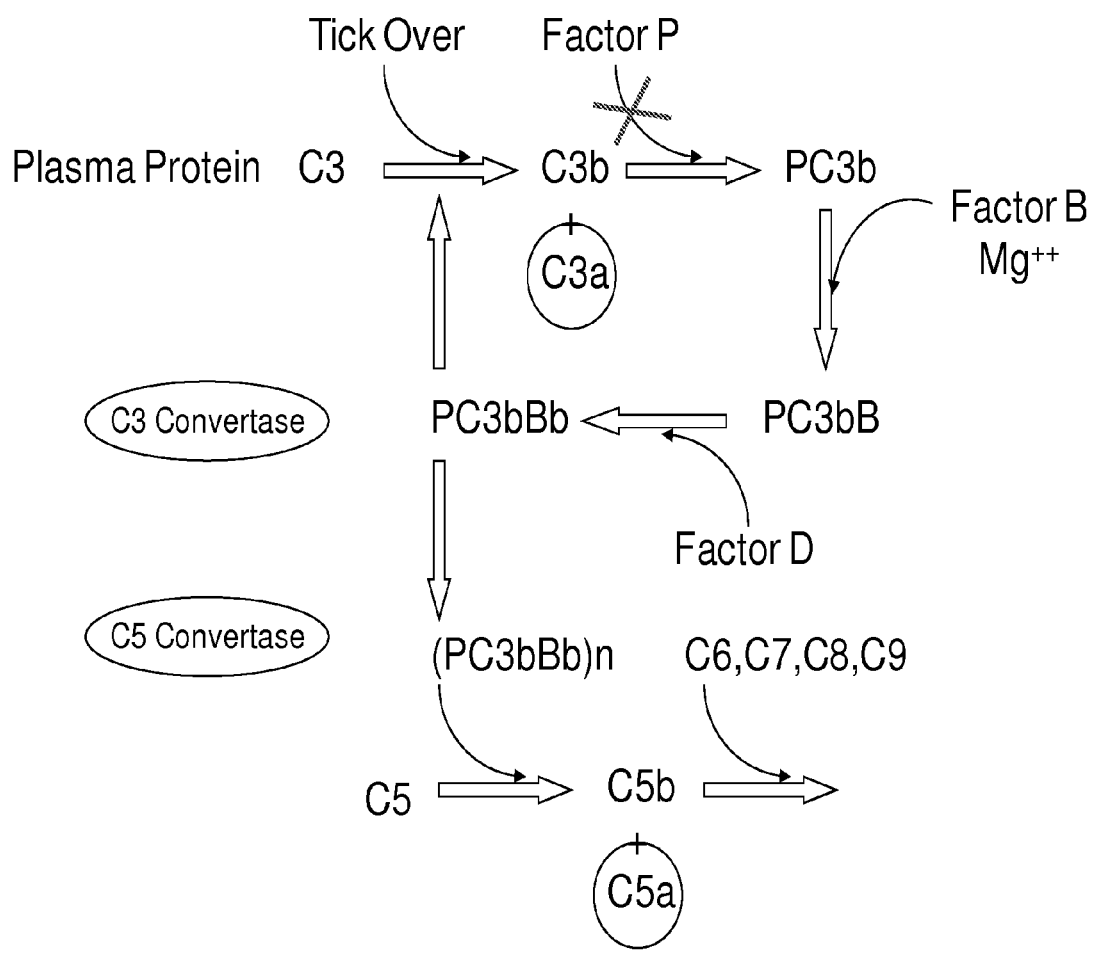
FIG. 2 illustrates a schematic of AP activation.

The term "polypeptide" is used herein as a generic term to refer to native protein, fragments, or analogs of a polypeptide sequence. Hence, native protein, fragments, and analogs are species of the polypeptide genus.

The term "polypeptide fragment" as used herein refers to a polypeptide that has an amino-terminal and/or carboxyl-terminal deletion, but where the remaining amino acid sequence is identical to the corresponding positions in the naturally occurring sequence deduced, for example, from a full-length properdin sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a polypeptide to a specific binding partner when an excess of antibody reduces the quantity of the polypeptide bound to the specific binding partner by at least about 20%, 40%, 60% or 80%, and more usually greater than about 85% (as measured in an in vitro competitive binding assay).

The term "monoclonal" refers to an antibody that binds to a sequence of amino acid and has a single specific epitope on its target antigen. For example, MoAb$^{71-110}$ is a monoclonal antibody that is specific only to the 71-110 amino acid sequence of properdin. Because the antibody is monoclonal, it would recognize a domain/motif that contains the sequence contained in 71-110 peptide (SEQ ID NO: 2).

The term "polyclonal" refers to an antibody that recognizes multiple epitope sites on a single antigen. For example, a polyclonal antibody against properdin indicates that the antibody will bind several sites of the properdin protein.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The terms "oligomer" and "polymer" are used interchangeable. The terms "oligomer" and "polymer" refer to the association of more than one monomer of a specific protein, peptide, or peptide fragments. The terms "oligomer" and "polymer" in this invention specifically relates to the ability of properdin protein monomers to form protein complexes with it or with other proteins.

The term "agent" is used herein to denote a chemical compound, a mixture of chemical compounds, a biological macromolecule, or an extract made from biological materials.

The terms "patient," "mammalian host," and the like are used interchangeably herein, and refer to mammals, including human and veterinary subjects.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "a disease or disorder associated with the alternative complement pathway," as used herein, refers to a disease or disorder caused, directly or indirectly, by activation of the alternative complement pathway, a disease or disorder that is mediated, directly or indirectly, by one or more components of the alternative complement pathway, or a product generated by the alternative complement pathway. The term also refers to a disease or disorder that is exacerbated by one or more components of the alternative complement pathway, or a product generated by the alternative complement pathway.

The term "knockout" refers to the technique in which a specific gene(s) are removed from a target animal. This technique is usually applied to rodents in which the gene of interest is removed via homologous recombination of an empty vector with the native animal chromosome. The technique works by swapping the animal's chromosome containing the gene with the empty vector containing a marker or random DNA sequences. This method results in an animal that is deficient of the gene of interest. The present invention would utilize this technique to generate antibodies against an antigen that is removed from the animal's genome to enhance generation of antibodies.

It is to be understood that this invention is not limited to particular embodiments described, as such may, of course, vary. It is also to be understood that the terminology used herein is for describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are encompassed within the invention, subject to any specifically excluded limit in the stated range. Where the stated range includes one or both of the limits, ranges excluding either or both of those included limits are also included in the invention.

The present invention relates to antibodies that specifically bind to properdin (i.e., anti-properdin antibody) and to the use of such antibodies to inhibit alternative complement pathway activation. The anti-properdin antibodies of the present invention are directed to or specifically bind to domains on properdin that are involved in controlling properdin function. The anti-properdin antibodies or fragments thereof of the present invention can inhibit alternate complement pathway activation without inhibiting or effecting classical complement activation as well as inhibit binding of properdin (oligomer/monomer) to C3b, inhibit binding of properdin to factor B, inhibit properdin binding to C3bB complex, inhibit factor D cleavage of factor B, reduce half life of the C3 convertase, prevent oligomerization of properdin monomers by blocking the N terminus of properdin which associates with TSR6 to generate oligomers, reduce formation of membrane attack complex C5b-9, reduce formation of anaphylatoxins, e.g., C3a and/or C5a, reduce formation of C3b, reduce activation of neutrophils, monocytes and platelets, and/or reduce leukocyte aggregate formation.

Studies have shown that the affinity of properdin to C3b is enhanced by factor B (DiScipio, R. G., *The binding of human complement proteins C5, factor B, beta 1H and properdin to complement fragment C3b on zymosan.* Biochem J, 1981. 199(3): p. 485-96). Thus, factor B and P are in close proximity in the trimolecular complex. Factor B association with C3b further enhances the affinity of P binding to C3bB. The complex PC3bB complex is oriented for factor D attack on factor B to generate Ba and Bb fragments. Free Ba and Bb do not bind C3b and therefore would not affect the binding of properdin to C3b. Properdin binding to factor D facilitates factor B cleavage by factor D. As a result, Ba is released and Bb remains bound to C3b. The active complex PC3bBb, a serine protease cleaves C3 to generate additional C3b molecules. It has been shown that properdin stabilizes convertase complex PC3bBb and the half-life is increased at least 10 fold (Fearon, D. T. and K. F. Austen, *Properdin: binding to C3b and stabilization of the C3b-dependent C3 convertase. J Exp Med,* 1975. 142(4): p. 856-63.).

The amino acid sequences of mammalian properdin are known. For example, the amino acid sequence of human properdin is disclosed in the GenBank database under Accession No. AAA36489 as SEQ ID NO: 1. Human properdin (SEQ ID NO: 1) is a 469 amino acid protein that includes a signal peptide (amino acids 1-28), and six, non-identical thrombospondin type 1 repeats (TSR) of about 60 amino acids each, as follows: amino acids 80-134 (TSR1), amino acids 139-191 (TSR2), amino acids 196-255 (TSR3), amino acids 260-313 (TSR4), amino acids 318-377 (TSR5), and amino acids 382-462 (TSR6). Reid et al have shown that all six TSRs of properdin have different function with TSR 5 being involved in properdin function (Higgins, J. M., et al., *Characterization of mutant forms of recombinant human properdin lacking single thrombospondin type I repeats. Identification of modules important for function.* J Immunol, 1995. 155(12): p. 5777-85). These studies utilized polyclonal TSR5 monoclonal antibody to inhibit alternative pathway dependent hemolysis of rabbit erythrocytes. Additional studies by the same authors demonstrated that deletions of TSRs 3, 4, and 6 did not affect properdin function. Both very strong studies suggested that it is the TSR5 that is responsible for properdin binding to C3b.

Unexpectedly, it was found that the N-terminal region of properdin including the first half of the TSR1 is important for properdin functions and that monoclonal antibodies, which specifically bind to an epitope of the N-terminal region (e.g. SEQ ID NO: 2, i.e., the 71-110 amino acid region of SEQ ID NO: 1), can inhibit properdin function.

An embodiment of the present invention therefore relates to anti-properdin antibodies that can bind to the N-terminal segment spanning into the TSR1 of properdin. Anti-properdin monoclonal antibodies in accordance with the invention, due to their large molecular weight, can potentially have some shielding effects on TSR6 in a dimer, trimer and tetrameric properdin and as a result abrogate the function of TSR6. Properdin monomers associate in a head to tail fashion with (N terminal+TSR1) domain associating with TSR6 of a second properdin monomer. As a result, dimeric, trimeric, and tetrameric properdin are assembled. The involvement of TSR6 was shown in a study in which TSR6 was deleted in a properdin mutant. Such properdin preparation did not produce dimers, trimers and tetramers of properdin.

Figure 3:
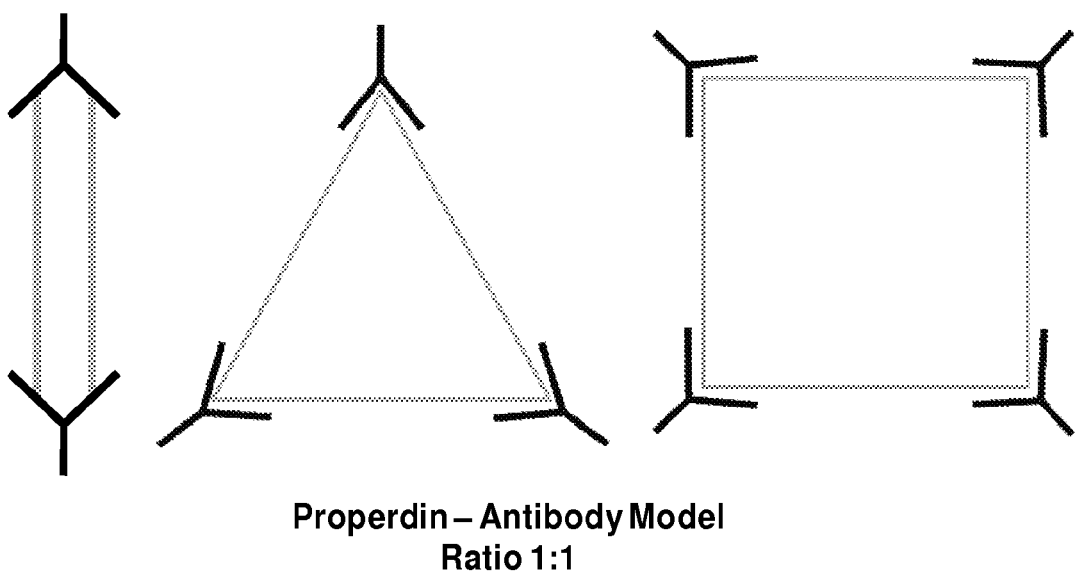
FIG. 3 illustrates a schematic of anti-properdin antibody binding in accordance with an aspect of the invention to properdin oligomers.

Anti-properdin antibodies can be selected based on their ability to inhibit AP dependent hemolysis of rRBC (rabbit erythrocytes) and then screened based on their ability to bind selected protein sequences present in the N-terminus region of properdin. These antibodies can bind to properdin in an about 1:1 stoichiometric ratio. Properdin exist in blood as a dimer, trimer, and tetramer in a ratio of 1:2:1. Therefore, dimers of properdin will bind two anti-properdin antibodies, trimers of properdin will bind three anti-properdin antibodies, and tetramers of properdin will bind four anti-properdin antibodies (FIG. 3).

Figure 4:
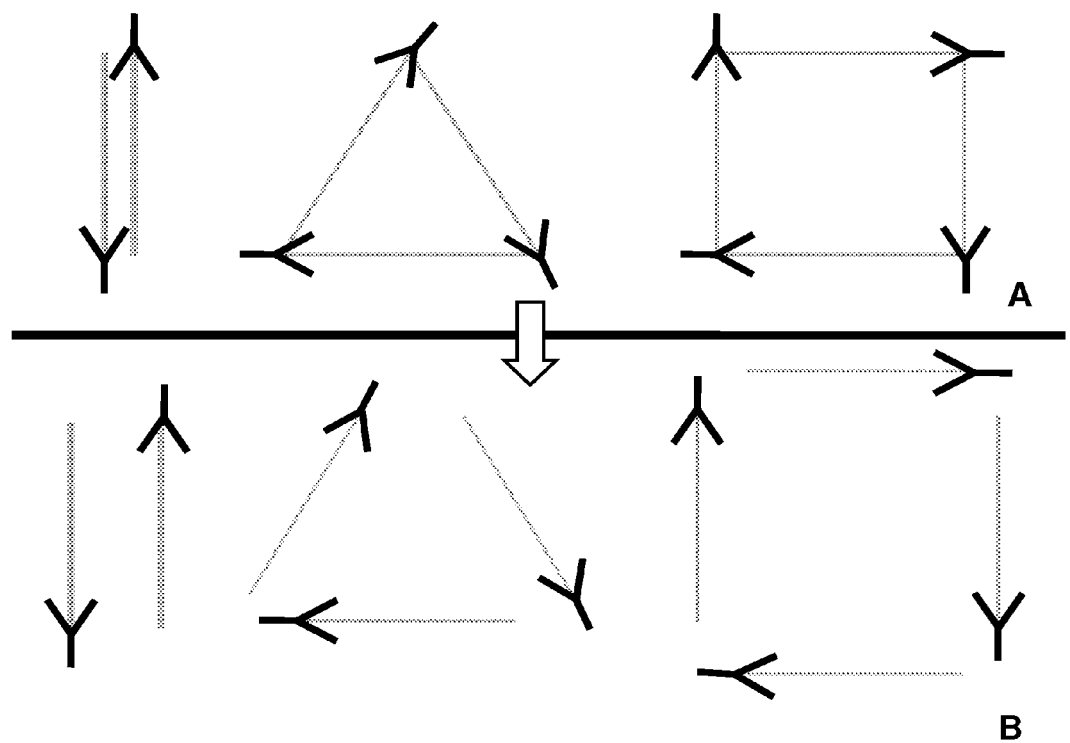
FIG. 4 illustrates a schematic of dissociation of properdin oligomers by anti-properdin antibodies in accordance with an aspect of the invention.

Only oligomeric forms of properdin are considered active. Oligomeric properdin binds C3b and initiates the AP activation. FIG. 4 illustrates that upon binding to the end of a properdin monomer of a properdin oligomer, the anti-properdin antibodies of the present invention will cause dissociation of the properdin oligomers into inactive properdin monomers. Inactive properdin monomers with bound anti-properdin are incapable of polymerizing to form activated properdin oligomers and are incapable of binding in monomer form to C3b or C3bB complex. In other words, dissociation of properdin oligomers into properdin monomers will inactivate the activated properdin. Such inactivation of properdin oligomers by anti-properdin antibodies of the present invention will prevent binding of oligomeric properdin to C3b and inhibit alternative pathway activation in the blood. Inhibition of alternative pathway complement activation will cause reduced levels of C3a, C5a, and C5b-9 and inhibit activation of monocytes, inhibit the formation of monocyte-platelet, and inhibit neutrophil-platelet aggregates.

In another embodiment of the present invention, the anti-properdin antibody specifically binds to an epitope of the N terminus end of properdin and therefore blocks the binding of TSR6 to the N terminus end of properdin (e.g., the N-terminal region and TSR1 region (SEQ ID NO: 3) of properdin (SEQ ID NO: 1)). For example, the anti-properdin antibody can specifically bind to an epitope that comprises at least a portion region of at least one of SEQ ID NO: 2, SEQ ID NO: 3, SEQ ID NO: 4, and/or SEQ ID NO: 5. The antibody can therefore prevent oligomerization of properdin monomers. In some embodiments, the anti-properdin antibody binds to other TSRs of the properdin polypeptide non specifically, e.g., where an epitope is shared between or among TSRs, and where shared epitopes may, but need not, be identical in amino acid sequence.

In other embodiments, the anti-properdin antibody inhibits binding of properdin to C3b. In these embodiments, the anti-properdin antibody affects the binding in an about 0.5:1 molar ratio of antibody to properdin, an about 1:1 molar ratio of antibody to properdin, an about 1.5:1 ratio of antibody to properdin and a maximum of about 10:1 antibody to properdin. In other embodiments, the anti-properdin antibody affects the binding in an about 0.5:1 to about 1.5:1 ratio. Properdin concentration in serum has been estimated to be 20 μg/ml (Chapitis, J. and I. H. Lepow, *Multiple sedimenting species of properdin in human serum and interaction of purified properdin with the third component of complement*. J Exp Med, 1976. 143(2): p. 241-57). Calculated levels in whole blood would be in range of 10 μg/ml considering 50% hematocrit. Based on these assumptions, the blood concentration of properdin is 200 nM. Surprisingly, the antibody of the present invention neutralizes 200 nM properdin with 200 nM monoclonal antibody. Three donors demonstrated consistent results.

The anti-properdin antibody of the present invention can also inhibit the level of functional properdin in a mammalian host. Functional properdin means properdin molecules capable of activating the alternative pathway. Properdin is important to the alternative pathway activation and the level of properdin in blood affects the amount of alternative complement pathway in blood. The antibody of the present invention reduces the level of functional properdin required for AP function. The amount of functional properdin is quantified using a sandwich ELISA in which properdin is sandwiched between the polyclonal and monoclonal antibody. Surprisingly, the NTSR antibody reduces the level of functional properdin in human blood.

The anti-properdin antibody can further reduce the levels of one or more components of the alternative complement pathway and/or one or more factors produced by action of one or more components of the alternative complement pathway. Exemplary, non-limiting examples of components and factors that are reduced include MAC(C5b-9), C3c, and anaphylatoxins, such as C3a and C5a, and the like. The anti-properdin antibody reduces the levels of one or more components of the alternative complement pathway and/or one or more factors produced by action of one or more components of the alternative complement pathway by at least about 20%, at least about 30%, at least about 40%, at least about 50%, at least about 60%, at least about 70%, at least about 80%, at least about 90%, or more, compared to the level of the component or factor in the absence of the subject antibody.

In another aspect of the invention, the anti-properdin antibody can bind properdin with high affinity, inhibit oligomerization of properdin, inhibit factor D mediated cleavage of factor B in a C3bB complex, not inhibit the classical complement pathway, prevent alternative complement pathway activation, inhibit C3a, C5a, and C5b-9 formation, Inhibit neutrophil, monocyte and platelet activation. Inhibit leukocyte platelet conjugate formation.

Figure 11:
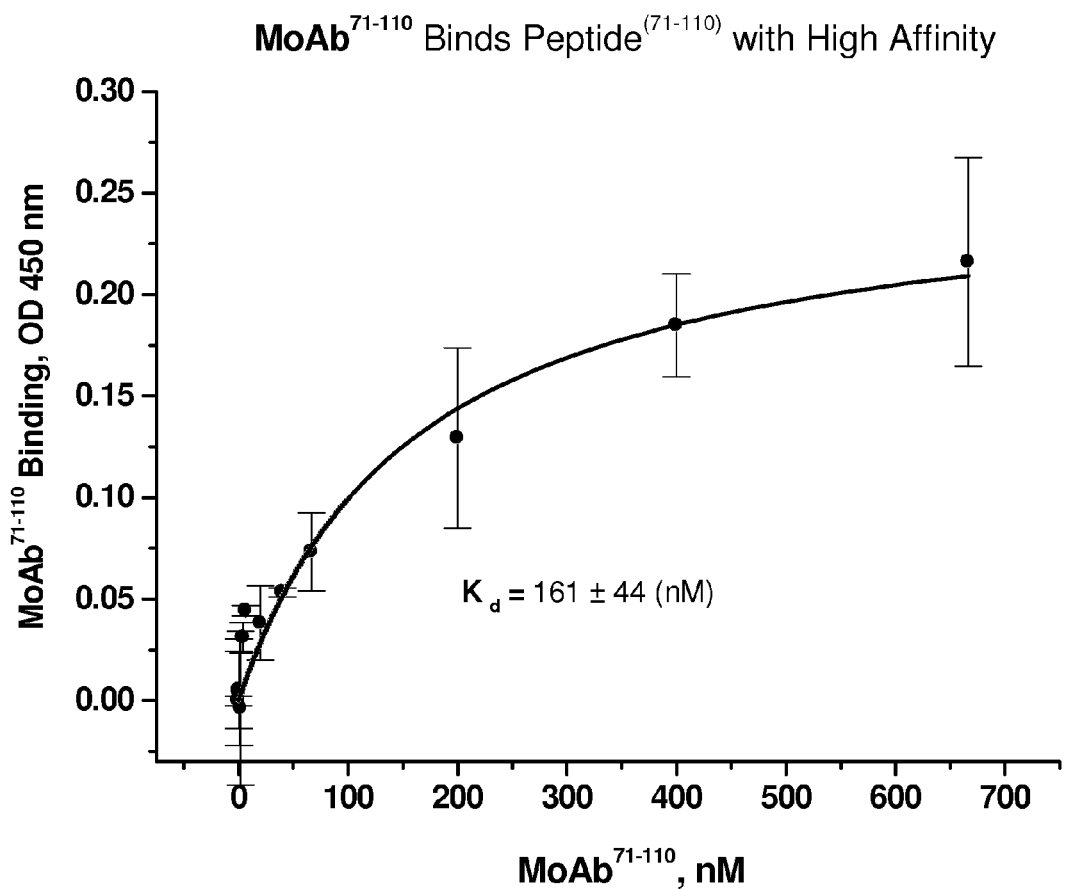
FIG. 11 shows the saturation binding of MoAb$^{71-110}$ to TSR-1 (71-110) (SEQ ID NO: 2). The line marked with filled circles represents the monoclonal antibody MoAb$^{71-110}$ binding to the substrate-bound TSR-1 fragment. The X-axis represents the concentration of the monoclonal antibody and the Y-axis represents the amount of bound monoclonal antibody to the substrate-bound TSR-1 fragment (71-110).

An example of an anti-properdin antibody in accordance with the present invention that specifically binds to SEQ ID NO: 2 was isolated and structurally characterized as described in the Examples. The Examples of the present application disclose an anti-properdin antibody identified as MoAbB$^{71-110}$ that is produced by the hybridoma cell line deposited under ATCC Accession Number PTA-9019. The hybridoma was deposited at the ATCC on Mar. 12, 2008 at ATCC, 10801 University Boulevard, Manassas, Va., under the terms of the Budapest Treaty. MoAb$^{71-110}$ was found to inhibit alternative complement pathway activation. MoAb"$^{71-110}$ inhibits factor D cleavage of C3bB complex. C3b produced by the cleavage of C3 binds factor B to produce the C3bB complex. Properdin binding to the complex C3bB promotes factor D induced cleavage of factor B. Evidence comes from studies using properdin-depleted serum, which has no complement activity suggesting that C3bB complex cannot be formed and cleaved with factor D in the absence of properdin. MoAb$^{71-110}$ prevents factor D cleavage of PC3bB complex. As shown in FIG. 11, the MoAb$^{71-110}$ prevents hemolysis of rRBC (rabbit erythrocytes) in AP buffer.

Additionally, while properdin is a part of the amplification loop, and in theory should have effect on the classical pathway activation surprisingly, MoAb$^{71-110}$ has no effect on classical pathway activation. MoAb$^{71-110}$ is an alternative pathway specific antibody and binds to a region on properdin that is only involved in AP activation. Use of MoAb$^{71-110}$ will keep the classical pathway (CP) intact for host defense, a significant benefit over the anti-properdin antibody discovered by Gupta-Bansal (Mol Immunol, 2000. 37(5): p. 191-201) and described in U.S. Pat. No. 6,338,034. Therefore, the present invention provides a process of inhibiting the alternative complement activation without inhibiting the classical pathway activation in vitro and in vivo in a human or animal subject.

In another embodiment, the heavy chain variable coding regions and the light chain variable coding regions of MoAB$^{71-110}$ were determined The V$_H$ amino acid sequence of MoAb$^{71-110}$ is shown in SEQ ID NO: 7. The V$_L$ amino acid sequence of MoAb$^{71-110}$ is shown in SEQ ID NO: 8. Accordingly, one aspect of the invention relate to an isolated monoclonal antibody, or antigen binding portion thereof comprising: (a) a heavy chain variable region comprising the amino acid sequence of SEQ ID NO: 7; and (b) a light chain variable region comprising the amino acid sequence of SEQ ID NO: 8; wherein the antibody specifically binds to human properdin.

Another aspect of the invention, relates to antibodies that comprise the heavy chain and light chain CDR1s, CDR2s and CDR3s of MoAb$^{71-110}$, or combinations thereof. The amino acid sequences of the V$_H$ CDR 1, 2 and 3 regions are shown in SEQ ID NOs: 9, 10 and 11, respectively. The amino acid sequences of the V$_L$ CDR 1, 2 and 3 regions are shown in SEQ ID NOs: 12, 13 and 14, respectively. Accordingly, in another aspect, the invention provides an isolated monoclonal antibody, or antigen binding portion thereof comprising: (a) a heavy chain variable region comprising CDR1, CDR2, and CDR3 comprising the amino acid sequences of SEQ ID NOs: 9, 10, and 11, respectively; (b) a light chain variable region comprising CDR1, CDR2, and CDR3 comprising the amino acid sequences of SEQ ID NOs: 4, 5, and 6, respectively; wherein the antibody specifically binds human properdin.

In another aspect, the invention relates to antibodies that bind to the same epitope on human properdin as the MoAb$^{71-110}$ (having V$_H$ and V$_L$ sequences as shown in SEQ ID NOs: 7 and 8). Such antibodies can be identified based on their ability to cross-compete with MoAB$^{71-110}$ in standard properdin binding assays. The ability of a test antibody to inhibit the binding of MoAb$^{71-110}$ to human properdin demonstrates that the test antibody can compete with MoAb$^{71-110}$ for binding to human properdin and thus binds to the same epitope on human properdin as MoAb$^{71-110}$. In an aspect of the invention, the antibody that binds to the same epitope on human properdin as MoAb$^{71-110}$ is a human monoclonal antibody. Such human monoclonal antibodies can be prepared and isolated as described in the Examples.

In yet another aspect, an antibody of the invention comprises heavy and light chain variable regions comprising amino acid sequences that are homologous to the amino acid sequences of the preferred antibodies described herein, and wherein the antibodies retain the desired functional properties of the anti-properdin antibodies of the invention. For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to the amino acid sequence of SEQ ID NO: 7; (b) the light chain variable region comprises an amino acid sequence that is at least 80% homologous to the amino acid sequence of SEQ ID NO: 8; and (c) the antibody specifically binds to human properdin.

In various aspects, the antibody can be, for example, a human antibody, a humanized antibody or a chimeric antibody. In other aspects, the V$_H$ and/or V$_L$ amino acid sequences may be 85%, 90%, 95%, 96%, 97%, 98% or 99% homologous to the sequences set forth above. An antibody having V$_H$ and V$_L$ regions having high (i.e., 80% or greater) homology to the V$_H$ and V$_L$ regions of the sequences set forth above, can be obtained by mutagenesis (e.g., site-directed or PCR-mediated mutagenesis) of nucleic acid molecules encoding SEQ ID NOs: 7 or 8, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., MoAb$^{71-110}$), or conservative modifications thereof, and wherein the antibodies retain the desired functional properties of the anti-CD64 antibodies of the invention. Accordingly, the invention provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein: (a) the heavy chain variable region CDR3 sequence comprises the amino acid sequence of SEQ ID NO: 11, or conservative modifications thereof; (b) the light chain variable region CDR3 sequence comprises the amino acid sequence of SEQ ID NO: 14, or conservative modifications thereof; and (c) the antibody specifically binds to human properdin.

In a more specific example, the heavy chain variable region CDR2 sequence comprises the amino acid sequence of SEQ ID NO: 10, or conservative modifications thereof; and the light chain variable region CDR2 sequence comprises the amino acid sequence of SEQ ID NO: 13, or conservative modifications thereof. In a still more specific example, the heavy chain variable region CDR1 sequence comprises the amino acid sequence of SEQ ID NO: 9, or conservative modifications thereof; and the light chain variable region CDR1 sequence comprises the amino acid sequence of SEQ ID NO: 12, or conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Accordingly, another aspect of the invention pertains to an isolated monoclonal antibody, or antigen binding portion thereof, comprising a heavy chain variable region comprising CDR1, CDR2, and CDR3 sequences of SEQ ID NOs: 9, 10, and 11, respectively, and a light chain variable region comprising CDR1, CDR2, and CDR3 sequences comprising an amino acid sequence of SEQ ID NOs: 12, 13, and 14, respectively. Thus, such antibodies contain the $V_H$ and $V_L$ CDR sequences of MoAB[71-110] yet may contain different framework sequences from these antibodies.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the invention provides isolated anti-properdin monoclonal antibodies, or antigen binding portions thereof, comprising a heavy chain variable region comprising: (a) $V_H$ CDR1, CDR2, and CDR3 regions comprising the amino acid sequences of SEQ ID NOs: 9, 10, and 11, respectively, or an amino acid sequence having one, two, three, four or five amino acid substitutions, deletions or additions as compared to SEQ ID NOs: 9, 10, and 11; (b) $V_K$ CDR1, CDR2, and CDR3 regions comprising the amino acid sequences of SEQ ID NOs: 12, 13, and 14, respectively, or an amino acid sequence having one, two, three, four or five amino acid substitutions, deletions or additions as compared to SEQ ID NOs: 12, 13, and 14.

Human Antibodies

An important practical application of such a strategy is the "humanization" of the mouse humoral immune system. Introduction of human immunoglobulin (Ig) loci into mice in which the endogenous IgG genes have been inactivated offers the opportunity to study the mechanisms underlying programmed expression and assembly of antibodies as well as their role in B-cell development. Furthermore, such a strategy could provide an ideal source for production of fully human monoclonal antibodies (MoAbs)—an important milestone towards fulfilling the promise of antibody therapy in human disease. Fully human antibodies are expected to minimize the immunogenic and allergic responses intrinsic to mouse or mouse-derivatized MoAbs and increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal is to engineer mouse strains deficient in mouse antibody production with large fragments of the human IgG loci in anticipation that such mice would produce a large repertoire of human antibodies in the absence of mouse antibodies. Large human IgG fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human MoAbs with the desired specificity could be readily produced and selected.

Human anti-mouse antibody (HAMA) responses: While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against properdin in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art.

Additional Criteria for Antibody Therapeutics

As discussed herein, the function of a subject anti-properdin antibody appears important to at least a portion of its mode of operation. By function, we mean, by way of example, the activity of the anti-properdin antibody in inhibiting the alternative complement pathway, e.g., a subject anti-properdin antibody exhibits one or more of the following properties: (1) inhibits oligomeric properdin binding to C3b (or C3bB); (2) reduces C3bBb formation, (3) inhibits oligomerization of properdin monomers; (4) promotes dissociation of oligomeric properdin into monomers, (5) reduces formation of free properdin, (6) reduces formation of C3b, (7) reduces formation of C3a, C5a and MAC, (8) reduces monocytes CD11b expression, (9) reduces neutrophil CD11b expression, (10) reduces platelet CD62 P expression, (11) reduces leukocyte-platelet conjugate formation, and (12) reduces tumor necrosis factor alpha (TNF).

Design and Generation of Other Therapeutics

Other therapeutic modalities beyond antibody moieties can be facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules. In connection with the generation of advanced antibody therapeutics, where complement fixation is a desirable attribute, it may be possible to sidestep the dependence on complement for cell killing using bispecifics, immunotoxins, or radiolabels, for example.

Bispecific antibodies can be generated that comprise (i) two antibodies one with a specificity to properdin and another to a second molecule that are conjugated together, (ii) a single antibody that has one chain specific to properdin and a second chain specific to a second molecule, or (iii) a single chain antibody that has specificity to properdin and the other molecule. Such bispecific antibodies can be generated using techniques that are well known for example, in connection with (i) and (ii) (Fanger, M. W., R. F. Graziano, and P. M. Guyre, *Production and use of anti-FcR bispecific antibodies*. Immunomethods, 1994. 4(1): p. 72-81) and in connection with (iii) (Traunecker, A., A. Lanzavecchia, and K. Karjalainen, *Janusin: new molecular design for bispecific reagents*. Int J Cancer Suppl, 1992. 7: p. 51-2). In each case, the second specificity can be made to the heavy chain activation receptors, including, without limitation, CD16 or CD64 (Deo, Y. M., et al., *Clinical significance of IgG Fc receptors and Fc gamma R-directed immunotherapies*. Immunol Today, 1997. 18(3): p. 127-35) or CD89 (Valerius, T., et al., *FcalphaRI (CD89) as a novel trigger molecule for bispecific antibody therapy*. Blood, 1997. 90(11): p. 4485-92). Bispecific antibodies prepared in accordance with the foregoing would be likely to kill cells expressing properdin and particularly those cells in which the anti-properdin antibodies of the invention are effective.

In connection with the generation of therapeutic peptides, through the utilization of structural information related to properdin and antibodies thereto, such as the antibodies of the invention (as discussed below in connection with small molecules) or screening of peptide libraries, therapeutic peptides can be generated that are directed against properdin.

Assuming that the properdin molecule (or a form, such as a splice variant or alternate form) is functionally active in a disease process, it will also be possible to design gene and antisense therapeutics thereto through conventional techniques. Such modalities can be utilized for modulating the function of properdin.

Therapeutic Uses

The anti-properdin antibody or fragments thereof can be used in therapeutic methods for the treatment of diseases mediated, directly or indirectly, by a component of the alternative complement pathway, and/or by a factor generated following activation of the alternative complement pathway. The anti-properdin antibody avoids problems associated with rodent antibodies, i.e., adverse reactions in humans, such as hypersensitivity reactions, including urticaria, dyspnea, hypotension, anaphylaxis, and the like.

In one aspect of the invention, the antibodies can be used to inhibit complement activation via the alternative pathway in vivo in subjects, including humans, suffering from an acute or chronic pathological injury such as, but not limited to, atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration. In vivo inhibition of alternative complement pathway activation is accomplished by administering the antibody to the subject.

In one example, the anti-properdin antibodies can be used in an extracorporeal circulation procedure, such as cardiopulmonary bypass (CPB) procedures on a subject. In these procedures, circulating blood can be passed from a blood vessel of the subject, through a conduit and back to a blood vessel of the subject. The conduit can have a luminal surface comprising a material capable of causing at least one of complement activation, platelet activation, leukocyte activation, or platelet-leukocyte adhesion in the subject's blood. An anti-properdin antibody can be introduced into the subject's bloodstream in an amount effective to reduce at least one of complement activation, platelet activation, leukocyte activation, or platelet-leukocyte adhesion resulting from passage of the circulating blood through the conduit. The blood of the subject can be passed through the conduit before and/or during and/or after step introduction of the anti-properdin antibody or fragment thereof. Preferably, the anti-properdin antibody reduces the alternative pathway-dependent conversion of complement component C3 into complement components C3a and C3b, and/or the alternative pathway-dependent formation of C5b-C9, and/or the alternative pathway-dependent leukocyte activation.

Therapeutic Administration and Formulations

It will be appreciated that the therapeutic entities in accordance with the invention will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as LIPFECTIN), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, if the active ingredient in the formulation is not inactivated by the formulation and the formulation is physiologically compatible and tolerable with the route of administration.

Preparation of Antibodies

Antibodies in accordance with the invention are prepared in mouse using standard methods well know in the art. The monoclonal antibody of the present invention will be converted into a humanized version for therapeutic use. The antibody can be made by contract or in house into humanized, fully human, chimeric, recombinant for therapeutic use. The hybridoma cell lines discussed herein are readily generated by those of ordinary skill in the art, given the guidance provided herein. The antibodies produced by the subject cell lines do not generate an adverse response. Adverse response is defined as an unwanted response.

Antibodies in accordance with the present invention can be expressed in cell lines other than hybridoma cell lines. Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive properdin binding properties.

The results of the present invention indicate that antibodies can be made more efficacious than currently available antibodies against properdin and therefore will be efficacious in treating disorders associated with and/or mediated by the alternative complement pathway.

Antibodies of this present invention can also be generated using properdin knockout mice, rodents to generate effective blocking antibodies. Because these rodents do not contain the properdin gene, the rodents would see the injection of properdin as an immunogenic antigen rather than a normal protein present in the system. Because of this recognition of the injected properdin as an antigen, the rodent will generate antibodies against it. The benefit of using a knockout rodent allows for increased probability for the generation of an antibody that is anti-rat, anti-mouse and anti-any other species, depending on the rodent being used, the potential for generating antibodies that are chimeric or human are easier to generate. Several therapeutic antibodies have been generated using xenomouse models to generate antibodies in mice that are chimeric or fully human (Davis, C. G., M. L. Gallo, and J. R. Corvalan, *Transgenic mice as a source of fully human antibodies for the treatment of cancer.* Cancer Metastasis Rev, 1999. 18(4): p. 421-5; Green, L. L., *Antibody engineering via genetic engineering of the mouse: XenoMouse strains are a vehicle for the facile generation of therapeutic human monoclonal antibodies.* J Immunol Methods, 1999. 231(1-2): p. 11-23; Wells, W. A., *Eek, a XenoMouse: Abgenix, Inc.* Chem. Biol, 2000. 7(8): p. R185-6). It is also possible to have double knockout for properdin and immunoglobulin to generate chimeric and fully human anti properdin antibody.

Human antibodies against a variety of antigens can also be produced from non-human transgenic mammals comprising human immunoglobulin loci. Typically these immunoglobulin loci can encode substantially human sequence antibodies, preferably 95% or more identical to human sequences, more preferably 98-99% or more identical, and most preferably 100% identical. The immunoglobulin loci can be rearranged or unrearranged, and can comprise deletions or insertions relative to the natural human immunoglobulin loci. The loci can include genetic elements (e.g., non-coding elements such as enhancers, promoters, and switch sequences, or coding elements such as mu constant region gene segments) from other species, and from non-immunoglobulin loci, that do not contribute substantially to the coding portion of secondary repertoire (non IgM) antibodies. The human immunoglobulin loci contained in these transgenic mammals preferably include unrearranged sequences of natural human heavy and human light chain loci. Usually, the endogenous immunoglobulin locus of such transgenic mammals is functionally inactivated (U.S. Pat. No. 5,589,369, Takeda, S. et al., 1993, *EMBO J.* 12:2329-2366; Jakobovits, A., et al., 1993, *Proc. Natl. Acad. Sci. U.S.A.* 90:2551-2555; Kitamura, D. and Rajewsky, K., 1992, *Nature* 356: 154-156; Gu, H. et al., 1991, *Cell* 65:47-54; Chen, J. et al., *EMBO J.* 12:821-830; Sun, W. et al., 1994, *J. Immunol.* 152:695-704; Chen, J. et al., 1993, *Intl. Immunology* 5:647-656; Zou, X. et al., 1995, *Eur. J. Immunol.* 25:2154-2162; Chen, J. et al., 1993 *Intl. Immunology* 5:647-656; Boudinot, P., et al, 1995, *Eur. J. Immunol.* 25:2499-2505; Chen, J. et al., 1993, *Proc. Natl. Acad. Sci.*

90:4528-4532; Roes, J. and Rajewsky, K., 1991, *Intl. Immunology* 3:1367-1371; Gu, H. et al., 1993, *Cell* 73:1155-1164; Taki, S. et al., 1993, *Science* 262: 1268-71; Kitamura, D. et al., 1991, *Nature* 350:423-6; Lutz, C. et al., 1998, *Nature* 393:797-801; Zou, Y. et al, 1994, *Current Biology* 4: 1099-1103; Chen, J. et al., 1993, *EMBO J.* 12:4635-4645; Serwe, M. and Sablitzky, F., 1993, *EMBO J.* 12:2321-2327; Sanchez, P. et al., 1994, *Intl. Immunology* 6:711-719; Zou, Y. et al., 1993, *EMBO J.* 12:811-820). Inactivation of endogenous immunoglobulin genes preferably can be achieved, e.g., by targeted homologous recombination. The exogenous human immunoglobulin loci can be associated the endogenous mouse chromosomes or can be of (e.g., part of, inserted within or attached to) an introduced transchromosome. Transchromosomes are introduced into a cell as a nonendogenous chromosome or chromosome fragment having a centromere and two telomeres. These transchromosomes commonly comprise telomere and centromere sequences and can comprise deletions relative to the parental intact chromosome. Transchromosomes can also comprise additional inserted sequences. A single transchromosome comprising two or three different immunoglobulin loci provides for genetic linkage of these loci which increases the fraction of transgenic offspring that are useful for making human antibodies. Preferred forms of transchromosomes are those described in detail in Tomizuka, K. et al., 2000, *Proc. Natl. Acad. Sci. U.S.A.* 97:722-727, Tomizuka, K. et al., 1997, *Nature Genetics* 16:133-143, and WO 97/07671, WO 98/37757 and WO 00/10383, each of which is incorporated by reference in its entirety for all purposes. Transchromosomes can also include integrated selectable markers and other sequences not found in the parent intact chromosome. In the event of recombination between a transchromosome and an endogenous mouse chromosome, sequences from the transchromosome are inserted or added to the endogenous mouse chromosome. Transchromosomes can be modified by deletion, translocation, substitution and the like, as described in WO 98/37757, EP 0972445 and WO 00/10383, which are incorporated herein by reference for all purposes. For example, transchromosomes can be fragmented spontaneously in the course of introduction into mouse embryonic stem (ES) cells, fragmented by telomere-directed truncation and/or translocated by Cre/loxP site-specific recombination or similar methods. Such recombination or translocation events can be promoted by specifically inserting recombination sites (e.g., loxP sequences and others; see, e.g., Abuin, A. and Bradley, A., 1996, *Mol. Cell. Biol.* 16: 1851-1856; Mitani, K. et al., 1995, *Somat. Cell. Mol. Genet.* 21:221-231; Li, Z. W. et al., 1996, *Proc. Natl. Acad. Sci. U.S.A.* 93:6158-6162; Smith, A J. et al., 1995, *Nat. Genet.* 9:376-385; Trinh, K R. and Morrison, S. L., 2000, *J. Immunol. Methods* 244:185-193; Sunaga, S. et al., 1997, *Mol. Reprod. Dev.* 46: 109-113; Dymecki, S. M., 1996, *Proc. Natl. Acad. Sci. U.S.A.* 93:6191-6196; Zou, Y R. et al., 1994, *Curr. Biol.* 4: 1099-1103; Rudolph, U. et al., 1993, *Transgenic Res.* 2:345-355; Rickert, R. C. et al., 1997, *Nucleic Acids Res.* 25:1317-1318). In the case of introduced loxP sites, expression of a transgene encoding the cre recombinase will promote recombination between the two loxP sites. Transchromosomes can also be a fusion chromosome consisting of different chromosome fragments as a result of the translocation described above. Transchromosomes can be autonomous. Autonomous transchromosomes are distinct from, are noncontiguous with, and are not inserted into the endogenous mouse chromosomes. These autonomous transchromosomes comprise telomere and centromere sequences that enable autonomous replication. Alternatively, transchromosome sequences can be translocated to mouse chromosomes after introduction into mouse cell nuclei. The endogenous mouse chromosomes include 19 autosomal chromosome pairs and the X and Y chromosomes.

Introduction of exogenous human immunoglobulin loci can be achieved by a variety of methods including, for example, microinjection of half-day embryo pronuclei, transfection of embryonic stem cells, or fusion of embryonic stem cells with yeast spheroplasts or micronuclei comprising transchromosomes. The transgenic mammals resulting from the processes described above are capable of functionally rearranging the introduced exogenous immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO 93/12227 (1993); U.S. Pat. Nos. 5,877,397, 5,874,299, 5,814, 318, 5,789,650, 5,770,429, 5,661,016, 5,633,425, 5,625,126, 5,569,825, 5,545,806, *Nature* 48:1547-1553 (1994), *Nature Biotechnology* 14, 826 (1996), Kucherlapati, WO 91/10741 (1991), WO 94/02602 (1993), WO 96/34096 (1995), WO 96/33735 (1996), WO 98/24893 (1997), U.S. Pat. Nos. 5,939, 598, 6,075,181, 6,114,598, Tomizuka, K. et al., 2000, *Proc. Natl. Acad. Sci. U.S.A.* 97:722-727, Tomizuka, K. et al., 1997, *Nature Genetics* 16:133-143, and Tomizuka, K., WO 97/07671, WO 98/37757, WO 00/10383, and JP 2000-42074 (each of which is incorporated by reference in its entirety for all purposes). Transgenic nonhuman mammals such as rodents are particularly suitable. Monoclonal antibodies can be prepared, e.g., by fusing B-cells from such mammals to suitable immortal cell lines using conventional Kohler-Milstein technology. Monoclonal antibodies can also be accessed directly from individual B cells, isolated from the medium, using PCR amplification of V regions (Schrader et al., 1997, U.S. Pat. No. 5,627,052). Alternatively, FACs sorted, or otherwise enriched B cell preparations can be used as a source of RNA or DNA for PCR amplification of V region sequences. Phage display methods (described below) can also be used to obtain human antibody sequences from immunized transgenic mice comprising human immunoglobulin loci. The human antibody V region sequences obtained by these methods can then be used to generate intact antibodies that retain the binding characteristics of the original parent antibodies. This process is described below.

A further approach for obtaining human antibodies is to screen a cDNA library from cells according to the general protocol outlined by Huse et al., 1989, *Science* 246:1275-1281. Such cells can be obtained from a human immunized with the desired antigen, fragments, longer polypeptides containing the antigen or fragments or anti-idiotypic antibodies. The cells can also be obtained from transgenic non-human animals expressing human immunoglobulin sequences. The transgenic non-human animals can be immunized with an antigen or collection of antigens. The animals can also be unimmunized. The V region encoding segments of the cDNA sequences are then cloned into a DNA vector that directs expression of the antibody V regions. Typically, the V region sequences are specifically amplified by PCR prior to cloning. Also typically, the V region sequences are cloned into a site within the DNA vector that is constructed so that the V region is expressed as a fusion protein. The collection of cloned V region sequences is then used to generate an expression library of antibody V regions. To generate an expression library, the DNA vector comprising the cloned V region sequences is used to transform eukaryotic or prokaryotic host cells. In addition to V regions, the vector can optionally encode all or part of a viral genome, and can comprise viral packaging sequences. In some cases, the vector does not comprise an entire virus genome, and the vector is then used together with a helper virus or helper virus DNA sequences. The expressed antibody V regions are found in, or on the surface of, transformed cells or virus particles from the transformed cells. This expression library, comprising the cells or virus particles, is then used to identify V region sequences that encode antibodies, or antibody fragments reactive with predetermined antigens. To identify these V region sequences, the expression library is screened or selected for reactivity of the expressed V regions with the predetermined antigens. The cells or virus particles comprising the cloned V region sequences, and having the expressed V regions, are screened or selected by a method that identifies or enriches for cells or virus particles that have V regions reactive (e.g., binding association or catalytic activity) with a predetermined antigen. For example, radioactive or fluorescent labeled antigen that then binds to expressed V regions can be detected and used to identify or sort cells or virus particles. Antigen bound to a solid matrix or bead can also be used to select cells or virus particles having reactive V regions on the surface. The V region sequences thus identified from the expression library can then be used to direct expression, in a transformed host cell, of an antibody or fragment thereof, having reactivity with the predetermined antigen. The protocol described by Huse is rendered more efficient in combination with phage-display technology. See, e.g., Dower et al., WO 91/17271 and McCafferty et al., WO 92/01047, U.S. Pat. Nos. 5,871,907, 5,858,657, 5,837,242, 5,733,743, and 5,565,332, (each of which is incorporated by reference in its entirety for all purposes). In these methods, libraries of phage are produced in which members (display packages) display different antibodies on their outer surfaces. Antibodies are usually displayed as Fv or Fab fragments. Phage displaying antibodies with a desired specificity can be selected by affinity enrichment to the antigen or fragment thereof. Phage display combined with immunized transgenic non-human animals expressing human immunoglobulin genes can be used to obtain antigen specific antibodies even when the immune response to the antigen is weak.

In a variation of the phage-display method, human antibodies having the binding specificity of a selected murine antibody can be produced. See, for example, Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for the selected are selected. Artificial antibodies that are similar to human antibodies can be obtained from phage display libraries that incorporate random or synthetic sequences, for example, in CDR regions.

The heavy and light chain variable regions of chimeric, humanized, or human antibodies can be linked to at least a portion of a human constant region by various well-known methods (see, e.g., Queen et al., 1989, *Proc. Natl. Acad. Sci. U.S.A.* 86:10029-10033 and WO 90/07861; these references and references cited therein are herein incorporated by reference for all purposes). The choice of constant region depends, in part, whether antibody-dependent complement and/or cellular mediated toxicity is desired. For example, isotypes $IgG_1$ and $IgG_3$ usually have greater complement binding activity than isotypes $IgG_2$ or $IgG_4$. Choice of isotype can also affect passage of antibody into the brain. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

For some applications, non IgG antibodies can be useful. For example, where multivalent antibody complexes are desired, IgM and IgA antibodies can be used.

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, FROM GENES TO CLONES, (VCH Publishers, NY, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., 1986, *Immunol. Rev.* 89:49), and necessary processing information sites, such as ribosome binding sites, RNA splice sites, polyadenylation sites, and transcriptional terminator sequences.

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

One example of a method of preparing a recombinant polyclonal antibody is by making polyclonal antibody libraries (PCAL), for instance as disclosed in U.S. Pat. No. 5,789,208 (to J. Sharon) which is hereby incorporated by reference in its entirety.

More specifically, the polyclonal antibody included in the pharmaceutical composition may be prepared by immunizing an animal, preferably a mammal, with an antigen of choice followed by the isolation of antibody-producing B-lymphocytes from blood, bone marrow, lymph nodes, or spleen. Alternatively, antibody-producing cells may be isolated from an animal and exposed to an antigen in vitro against which antibodies are to be raised. The antibody-producing cells may then be cultured to obtain a population of antibody-producing cells, optionally after fusion to an immortalized cell line such as a myeloma.

A combinatorial library may be prepared from immunized B lymphocytes by associating $V_L$ and $V_H$ randomly in a cloning vector. Thus, the recombinant polyclonal antibody is generated under such conditions that the immunoglobulin heavy chain variable region and light chain variable region gene segments are linked together randomly in order to allow for the bulk transfer of variable region light chain and heavy chain gene pairs from one vector to another, while allowing stable pairing of specific immunoglobulin variable region light chain and heavy chain gene segments as they are present upon selection from a parental library of immunoglobulin variable region light chain and heavy chain gene segment pairs encoding antibody molecules capable of reacting with or binding to an allergen.

Single cell PCR may be used in an attempt to retain the native pairing of $V_L$ and $V_H$ in the single cell. In this case antibody-producing B-lymphocytes which have been isolated from animals or humans may be fixed with a fixative solution or a solution containing a chemical such as formaldehyde, glutaraldehyde or the like. The cells are then permeabilized with a permeabilization solution comprising for example a detergent such as Brij, Tween, polysorbate, Triton X-100, or the like. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ mRNA into the corresponding cDNA sequences.

Upon reverse transcription, the resulting cDNA sequences may be amplified by PCR using primers specific for immunoglobulin genes and, in particular, for the terminal regions of the $V_H$ and $V_L$ nucleic acids. PCR procedures may be followed as disclosed in, e.g., U.S. Pat. No. 4,683,195. Preferably, the cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The amplified sequences are linked by hybridization of complementary terminal sequences. After linking, sequences may be recovered from cells. For example, after linking, cells can be washed in a solution of sodium dodecyl sulfate (SDS). The SDS precipitates out of the cells after incubation on ice and the supernatant can be electrophoresed into an agarose or acrylamide gel. Alternatively, or in combination with the SDS process, using a reagent such as digoxigenin-linked nucleotides, DNA products synthesized will remain within the cell and be amplified. The linked product is recovered upon electrophoresis of the supernatant.

After electrophoresis of the supernatant, the gel slice corresponding to the appropriate molecular weight of the linked product is removed and the DNA isolated on, for example, silica beads. The recovered DNA can be PCR amplified using terminal primers, if necessary, and cloned into vectors which may be plasmids, phages, cosmids, phagamids, viral vectors or combinations thereof. Convenient restriction enzyme sites may be incorporated into the hybridized sequences to facilitate cloning. These vectors may also be saved as a library of linked variable regions for later use.

The linked $V_H$ and $V_L$ region genes may be PCR amplified a second time using terminal nested primers, yielding a population of DNA fragments, which encode the linked $V_H$ and $V_L$ genetic regions. The grouping of $V_H$ and $V_L$ combinations is an advantage of this process and allows for the in mass or batch transfer of all clones and all DNA fragments during this and all cloning procedures.

The recombinant polyclonal antibody may be generated under such conditions that the immunoglobulin heavy chain variable region and light chain variable region gene segments are linked together in a head-to head orientation, in order to allow for the bulk transfer of variable region light chain and heavy chain pairs from one vector to another, including from phage to vector, and including from the cell of origin to phage or vector, resulting in a stable pairing of specific immunoglobulin variable region light chain and heavy chains gene segments as they are found in the original polyclonal immune response of the animal or human individual.

It may sometimes be desirable to treat the variable region gene sequences with a mutating agent. Mutating agents create point mutations, gaps, deletions or additions in the genetic sequence which may be general or specific, or random or site directed. Useful mutating agents include ultraviolet light, gamma irradiation, chemicals such as ethidium bromide, psoralen and nucleic acid analogs, or DNA modifying enzymes such as restriction enzymes, transferases, ligases and specific and nonspecific nucleases and polymerases. Moreover, it may be feasible to use mutator strains. In particular, random mutations may be introduced in the CDRs of the $V_H$ and $V_L$ region genes by oligonucleotide directed mutagenesis. Mutations introduced into the gene sequence will ultimately increase library complexity and diversity as well as affinity for antigen which may further increase the library's usefulness in treatment. Furthermore, such mutagenesis may be used on a single $V_H$ and $V_L$ pair or on a defined group of such pairs to generate a library de novo.

Vectors are transformed into suitable host cells and the cultures amplified to expand the different populations of vectors that comprise the library. Host cells for prokaryotic vectors may be a culture of bacteria such as *Escherichia coli*. Host cells for eukaryotic vectors may be a culture of eukaryotic cells such as any mammalian, insect or yeast cell lines adapted to tissue culture. Bacterial cells are transformed with vectors by calcium chloride-heat shock or electroporation, although many other transformation procedures would also be acceptable. Eukaryotic cells are transfected with calcium phosphate precipitation or electroporation, although many other transformation procedures would also be acceptable. The DNA fragments may be cloned into prokaryotic or eukaryotic expression vectors, chimeric vectors or dual vectors. The expression vector may be a plasmid, cosmid, phage, viral vector, phagemid and combinations thereof, but is preferably a phage display vector wherein the recombinant product is expressed on the phage surface to facilitate screening and selection. Useful transcriptional and translational sites may be placed on the expression vector including RNA polymerase recognition regions such as a TATA box site, a CAT site, an enhancer, appropriate splicing sites, if necessary, a AT rich terminal region and a transcription initiation site. Useful sites to facilitate translation include translational start and stop sites and ribosome binding sites. Typically, some of the more useful sites for efficient eukaryotic expression, such as the SV40, CMV, HSV or baculovirus promoter/enhancer region, are derived from viruses. The resulting recombinant antibody may be of the murine class $IgG_1$, $IgG_{2a}$, $IgG_{2b}$, IgM, IgA, IgD or IgE, the human classes $IgG_1$, $IgG_2$, $IgG_3$, $IgG_4$, IgM, $IgA_1$, $IgA_2$, IgD or IgE, or combinations or fragments thereof. Preferably, the chimeric antibody library is composed of primarily IgG antibodies or Fab antibody fragments.

Treatment Methods

The methods generally involve administering to a mammalian subject in need thereof an effective amount or therapeutically effective amount of a subject antibody for including methods of reducing the level of a polypeptide generated following activation of the alternative complement pathway; methods of reducing the level of membrane attack complex (MAC); methods of reducing the level of an anaphylatoxin; methods of reducing the level of C3b; and methods of treating a disease or disorder mediated by the alternative complement pathway.

An "effective amount" or "therapeutically effective" of a subject antibody is an amount that is effective to reduce the production and/or level of a polypeptide generated following activation of the alternative complement pathway by at least about 20%, at least about 30%, at least about 40%, at least about 50%, at least about 60%, at least about 70%, at least about 80%, at least about 90%, or more.

The anti-properdin antibody administered to an individual in a formulation with a pharmaceutically acceptable excipient(s). A wide variety of pharmaceutically acceptable excipients are known in the art and need not be discussed in detail herein.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, a subject antibody may be administered to the host using any convenient means capable of resulting in the desired therapeutic effect. Thus, the antibody can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of a subject antibody can be achieved in various ways, including oral, buccal, rectal, parenteral, intraperitoneal, intradermal, subcutaneous, intramuscular, transdermal, intranasal, pulmonary, intratracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject antibody calculated in an amount sufficient to produce the desired effect in association with a pharmaceutically acceptable diluent, carrier or vehicle.

A subject antibody is administered to an individual at a frequency and for a period of time so as to achieve the desired therapeutic effect. For example, a subject antibody is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

Combination Therapy

The anti-properdin antibody will in some embodiments be administered in an effective amount in combination therapy with a second therapeutic agent. Suitable second therapeutic agents include, but are not limited to, anti-inflammatory agents; agents used for the treatment of cardiovascular disorders; steroidal anti-inflammatory agents; and the like.

Suitable anti-inflammatory agents include, but are not limited to, non-steroidal anti-inflammatory drugs (NSAIDs) acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing. Other suitable anti-inflammatory agents include methotrexate.

Suitable steroidal anti-inflammatory agents include, but are not limited to, hydrocortisone, prednisone, prednisolone, methylprednisolone, dexamethasone, betamethasone, and triamcinolone.

Examples agents for cardiovascular indications include GP IIb-IIIa inhibitors such as INTEGRILIN (eptifibatide); aprotinin; REOPRO (abciximab); and the like.

Suitable second therapeutic agents include beta adrenergics which include bronchodilators including albuterol, isoproterenol sulfate, metaproterenol sulfate, terbutaline sulfate, pirbuterol acetate and salmeterol formotorol; steroids including beclomethasone dipropionate, flunisolide, fluticasone, budesonide and triamcinolone acetonide. Anti-inflammatory drugs used in connection with the treatment of respiratory diseases include steroids such as beclomethasone dipropionate, triamcinolone acetonide, flunisolide and fluticasone. Other examples of anti-inflammatory drugs include cromoglycates such as cromolyn sodium. Other respiratory drugs, which would qualify as bronchodilators, include anticholenergics including ipratropium bromide. Antihistamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin), claratyne (Claritin), claratyne D (Claritin D), telfast (Allegra), zyrtec, and beconase.

In some embodiments, the anti-properidin antibody is administered concurrently with a second therapeutic agent. As used herein, the term "concurrently" indicates that the subject antibody and the second therapeutic agent are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, the anti-properidin antibody is administered during the entire course of treatment with the second therapeutic agent. In other embodiments, a subject antibody is administered for a period of time that is overlapping with that of the treatment with the second therapeutic agent, e.g., the antibody treatment can begin before the treatment with the second therapeutic agent begins and end before the treatment with the second therapeutic agent ends; the antibody treatment can begin after the treatment with the second therapeutic agent begins and end after the antibody treatment ends; the antibody treatment can begin after the treatment with the second therapeutic agent begins and end before the treatment with the second therapeutic agent ends; or antibody treatment can begin before the treatment with the second therapeutic agent begins and end after the treatment with the second therapeutic agent ends.

Subjects for Treatment

Subjects that can be treated with a subject method include individuals suffering from one or more of the following disorders: atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

In an a particular aspect of the invention, subjects that can be treated with a subject method include individuals suffering from one or more of the following disorders: post-cardiopulmonary bypass inflammation, myocardial infarction, stroke, acute respiratory distress syndrome (ARDS), septic shock, transplant rejection, burn injury, multiple sclerosis, myasthenia gravis, cardiovascular disorders, and rheumatoid arthritis. Subjects suitable for treatment with a subject method also include individuals suffering from any inflammatory disorder, including, but not limited to, systemic lupus erythematosus, membranous nephritis, pemphigoid, dermatomyositis, and anti-phospholipid syndrome. Subjects suitable for treatment also include subjects undergoing renal dialysis.

Incorporation by Reference

All references cited herein, including patents, patent applications, papers, textbooks, and the like, and the references cited therein, to the extent that they are not already, are hereby incorporated herein by reference in their entirety. In addition, the following references are also incorporated by reference herein in their entirety, including the references cited in such references:

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

Unless stated otherwise all reagents were ultrapure. Small peptides, TSR5 peptides, and TSR6 peptides were synthesized by the core facility of Cleveland Clinic Foundation. All complement reagents were either from Advanced Research Technologies, San Diego, Calif., now Complementech, Tylar Tex. or from Quidel Corporation, San Diego, Calif. GVB for classical pathway, Phosphate buffered saline was purchased from Sigma-Aldrich, St Louise Mo., GVB for alternative complement pathway was purchased from Complementech, Tylar, Tex., All flow cytometry antibodies were from BD Biosciences, San Jose, Calif., TMB substrate was from Kirkegaard & Perry Limited, Gaithersberg, Md., rRBC and sheep erythrocytes (antibody sensitized) were from Complementech, Tylar, Tex., All secondary antibodies were from American Qualex, San Clemente, Calif., BSA and other reagents were all from Sigma-Aldrich, St Louise, Mo. Normal Human serum was freshly isolated using BD Biosciences Clotting tubes.

ELISA plate readers (SpectraMax 190 and 250) were from Molecular Devices, and Flow Cytometer was FACSCalibur. Varity 3D program was used for data analyses, Curve fittings were done using MicroCal Origin program. Hemolysis kinetic assay was run using SectraMax, Molecular Devices., ELISA plates were from Corning Costar, Lowell, Mass.

F(ab)2 was used for the extra corporeal circulation model. MoAb($^{71-110}$) was digested with Ficin to produce F(ab)2 using methods well known in the art.

Example 1

Properdin Peptide CRSPRWSLWS (SEQ ID NO: 4) Inhibits Alternative Pathway Activation The peptide CRSPRWSLWS (SEQ ID NO: 4) is located within the N terminal segment of properdin that connects the N terminal to TSR1 (SEQ ID NO: 1). Due to the small size of the peptide, it will not have the conformation of the native molecule and therefore is expected to have the poorer affinity compared to the native properdin. Properdin does not bind C3, it only binds C3b. C3 contains C3a and C3b not just C3b alone and might function differently than C3b. In this experiment, we tested inhibition of properdin binding to C3b by the peptide. We also determined if the peptide would also inhibit MAC(C5b-9) formation because formation of MAC demonstrates completion of the cascade.

C5b-9 Formation Assay: Microtiter wells were coated with LPS (2 µg/50 µl per well) in PBS overnight at 4° C. Uncoated wells served as background controls. After aspirating the LPS solution, wells were treated with 1% BSA in phosphate buffered saline, pH 7.4 (PBS) for 2-hours. Following a 2 hour incubation, wells were rinsed with PBS and incubated with various concentrations of the peptides in AP buffer containing 10% Normal Human Serum (NHS). Following a 2-hour incubation at 37° C. to allow AP activation to occur, deposited MAC(C5b-9) was detected with 1:2000 diluted mouse anti-human soluble neo-05b-9 monoclonal antibody. All dilutions of the monoclonal antibody were made in blocking solution and all antibody incubations were done for 1 hour at room temperature. The primary antibody was detected with goat anti mouse monoclonal (A2304, Sigma Chemical). Following each incubation the plate was rinsed five times with PBS. The plate was developed with TMB and the blue color reaction was quenched with 1M phosphoric acid.

Properdin-C3b Binding Assay: Polystyrene microtiter plates were coated with C3b protein (1.0 µg/50 µl per well) in PBS (Phosphate Buffered Saline) overnight at 4° C. After aspirating the C3b protein, the wells were blocked with 1% BSA in PBS for 2 hours at room temperature. Wells without C3b coating served as background controls. C3b coated wells were incubated with 5 nM properdin containing various concentrations of the synthetic peptide CRSPRWSLWS (SEQ ID NO: 4) (Advanced Research Technology, San Diego, Calif.) in blocking solution. The samples were added to the wells. Following a 2 hour incubation at room temperature, the wells were rinsed five with PBS. C3b bound properdin was measured by adding anti-human properdin monoclonal antibody P#2 at 1:2000 dilution in blocking solution. The plate was allowed to incubate for 1 hour at room temperature. After washing the plates with PBS, a peroxidase-conjugated goat anti-mouse antibody (1:2000 dilution in blocking solution) was added and allowed to incubate for 1 hour. The plate was again rinsed thoroughly with PBS, and 100 µl of TMB substrate was added. The blue color reaction of TMB was quenched by the addition of 100 µl of phosphoric acid, and the plate was read at 450 nm in a microplate reader.

Figure 5:
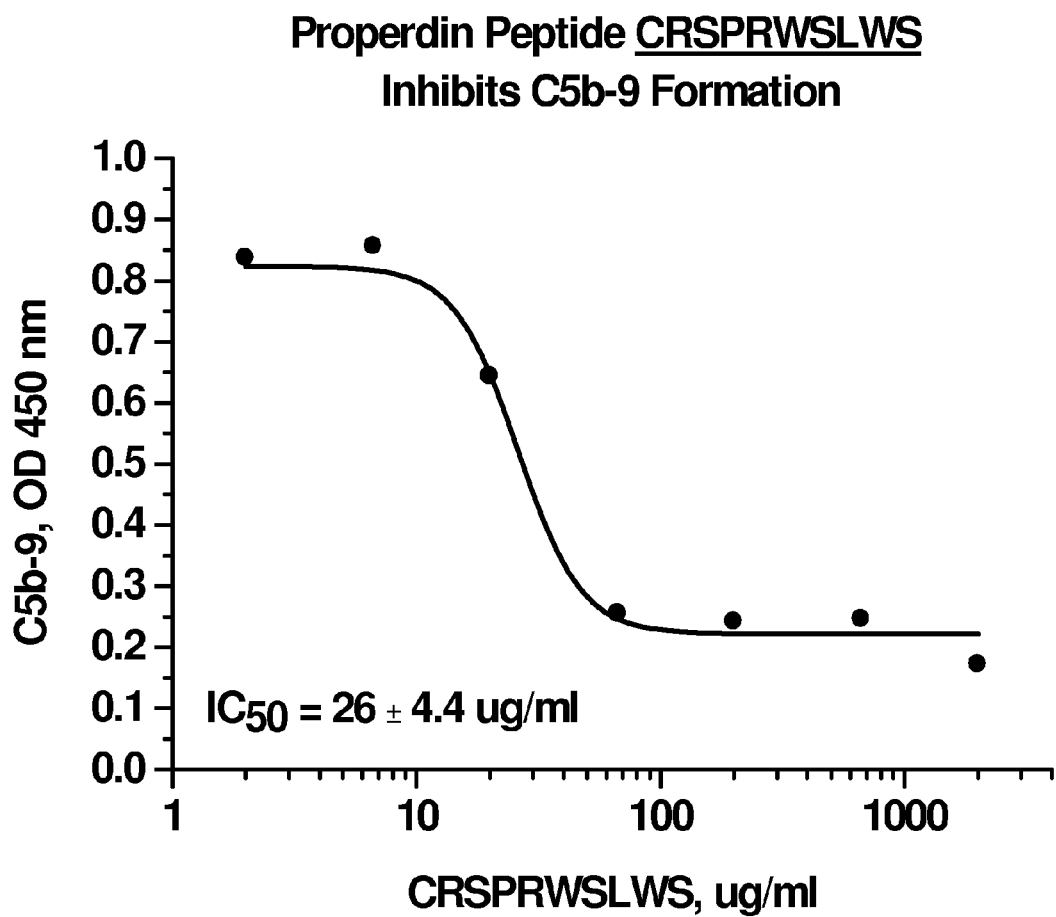
FIG. 5 shows the inhibition of C5b-9 formation by the CRSPRWSLWS (75-84) (SEQ ID NO: 4). The line marked with filled circles represents the peptide inhibition of C5b-9 formation. The X-axis represents concentration of the peptide in µg/ml concentration.
Figure 6:
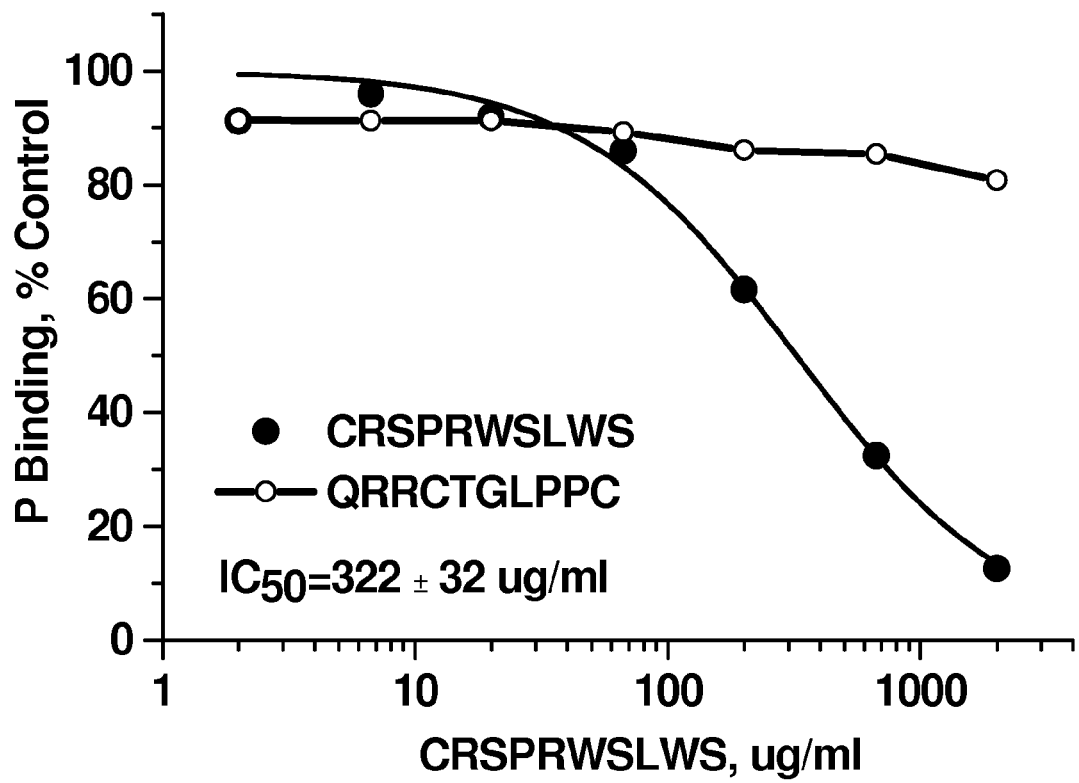
FIG. 6 shows the inhibition of properdin binding to C3b by CRSPRWSLWS (75-84) (SEQ ID NO: 4) but not by QRRCT-GLPPC peptide (245-254) (SEQ ID NO: 6) from the TSR region. This TSR 3 peptide was shown by the previous publications to be inhibitory.
Figure 7:
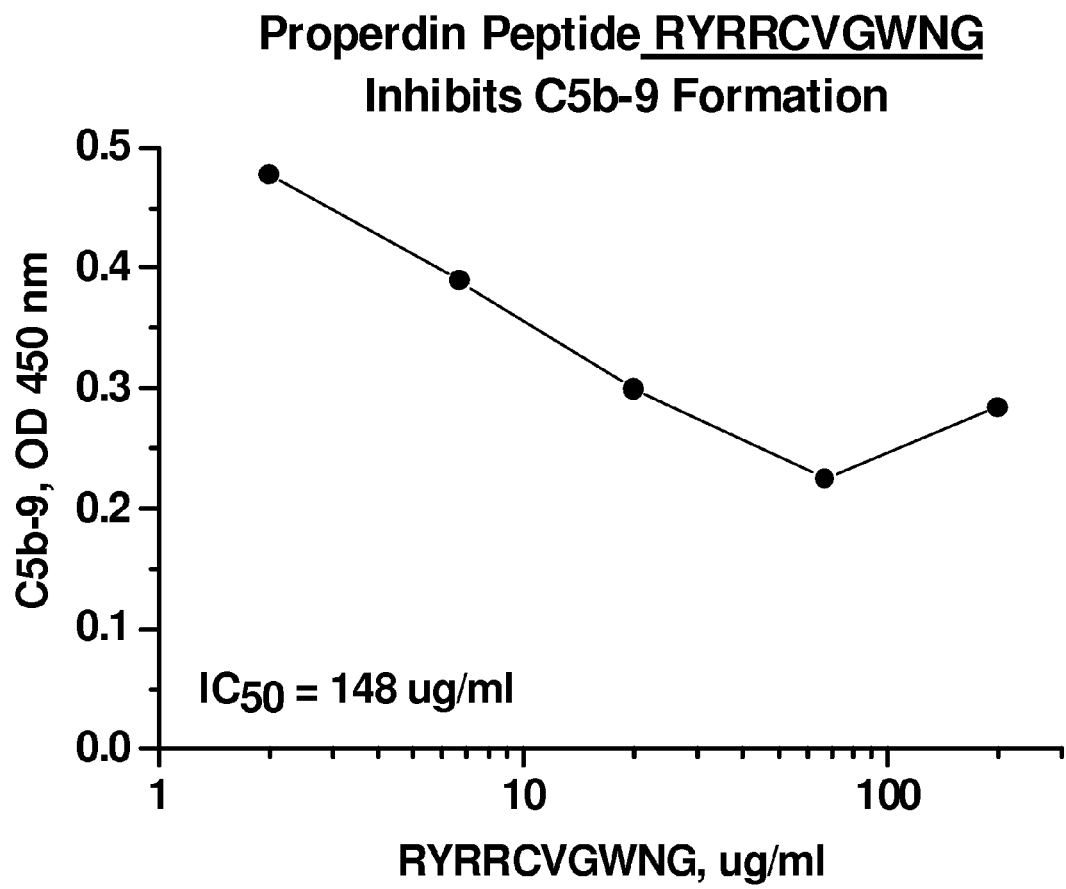
FIG. 7 shows the inhibition of C5b-9 formation by the peptide RYRRCVGWNG (99-108) (SEQ ID NO: 5) of the TSR-1 domain of properdin. The line marked with filled circles represents the peptide inhibition of C5b-9 formation. The X-axis represents the peptide (99-108 region) (SEQ ID NO: 5) concentration in µg/ml.

FIG. 5 shows that CRSPRWSLWS (SEQ ID NO: 4) peptide inhibits MAC formation in a dose dependent fashion with near complete inhibition being achieved at 60-100 µg/ml of the peptide. FIG. 6 shows that the same peptide is also effective at inhibiting properdin binding to C3b. The rationale for the large concentration of peptide necessary to inhibit is the fact that these peptides are very small in length and do not possess the native conformation of the original protein thus excess peptide is required to observe inhibitory effects. Another peptide taken from a region of properdin sequence does not inhibit properdin binding to C3b (FIG. 7). We have shown that Properdin binding to C3b cannot be competed with native C3 (unpublished observation). These same two peptides were shown to inhibit properdin binding to C3 which contains both the C3a domain and C3b domain. The observed difference in these and the previous studies may be the C3 being used as opposed to C3b used in these experiments.

Example 2

Properdin Peptide RYRRCVGWNG (SEQ ID NO: 5) Inhibits Alternative Pathway Activation The peptide RYRRCVGWNG (SEQ ID NO: 5) is located within the N terminal segment of TSR1, this is the same segment that was previously shown to have no inhibitory activity in AP activation assay. We have shown that properdin binding to C3b is independent on ions and can occur in EDTA. The present experiments were conducted in blocking solution that does not contain Mg or Ni. We also tested all five peptides previously shown as inhibitory in P—C3 binding assay. Out of five, only two peptides were specific to properdin-C3b binding. The other three had no effect on properdin binding to C3b or AP activation. The peptide CRSPRWSLWS (SEQ ID NO: 4) has been discussed in Example 1 and the second peptide RYRRCVGWNG (SEQ ID NO: 5) is being discussed here in the Example 2. This peptide RYRRCVGWNG (SEQ ID NO: 5) represents the segment of properdin that connects the N terminal region to TSR1. Due to the small size of the peptide, it will not have the conformation of the native molecule and therefore is expected to have the poorer affinity compared to the native properdin. Properdin does not bind C3, it only binds C3b. C3 contains C3a and C3b not just C3b alone and might function differently than C3b. In this experiment, we tested inhibition of properdin binding to C3b by the peptide. We also determined if the peptide would also inhibit MAC(C5b-9) formation because formation of MAC demonstrates completion of the cascade.

C5b-9 Formation Assay: Microtiter wells were coated with LPS (2 µg/50 upper well) in PBS overnight at 4° C. Uncoated wells served as background controls. After aspirating the LPS solution, wells were treated with 1% BSA in phosphate buffered saline, pH 7.4 (PBS) for 2-hours. Following a 2 hour incubation, wells were rinsed with PBS and incubated with various concentrations of the peptides in AP buffer containing 10% Normal Human Serum (NHS). Following a 2-hour incubation at 37° C. to allow AP activation to occur, deposited MAC(C5b-9) was detected with 1:2000 diluted mouse anti-human soluble neo-05b-9 monoclonal antibody. All dilutions of the monoclonal antibody were made in blocking solution and all antibody incubations were done for 1 hour at room temperature. The primary antibody was detected with goat anti mouse monoclonal. Following each incubation the plate was rinsed five times with PBS. The plate was developed with TMB and the blue color reaction was quenched with 1M phosphoric acid.

Properdin-C3b Binding Assay: Polystyrene microtiter plates (Corning, Cat.) were coated with C3b protein (1.0 µg/50 µl per well) in PBS (Phosphate Buffered Saline) overnight at 4° C. After aspirating the C3b protein, the wells were blocked with 1% BSA in PBS (Sigma-Aldrich, St. Louis, Mo.) for 2 hours at room temperature. Wells without C3b coating served as background controls. C3b coated wells were incubated with 5 nM properdin containing various concentrations of the synthetic peptide CRSPRWSLWS in blocking solution. The samples were added to the wells. Following a 2 hour incubation at room temperature, the wells were rinsed five with PBS. C3b bound properdin was measured by adding anti-human properdin monoclonal antibody P#2 at 1:2000 dilution in blocking solution. The plate was allowed to incubate for 1 hour at room temperature. After washing the plates with PBS, a peroxidase-conjugated goat anti-mouse antibody (1:2000 dilution in blocking solution) was added and allowed to incubate for 1 hour. The plate was again rinsed thoroughly with PBS, and 100 µl of TMB substrate was added. The blue color reaction of TMB was quenched by the addition of 100 µl of phosphoric acid, and the plate was read at 450 nm in a microplate reader.

Figure 8:
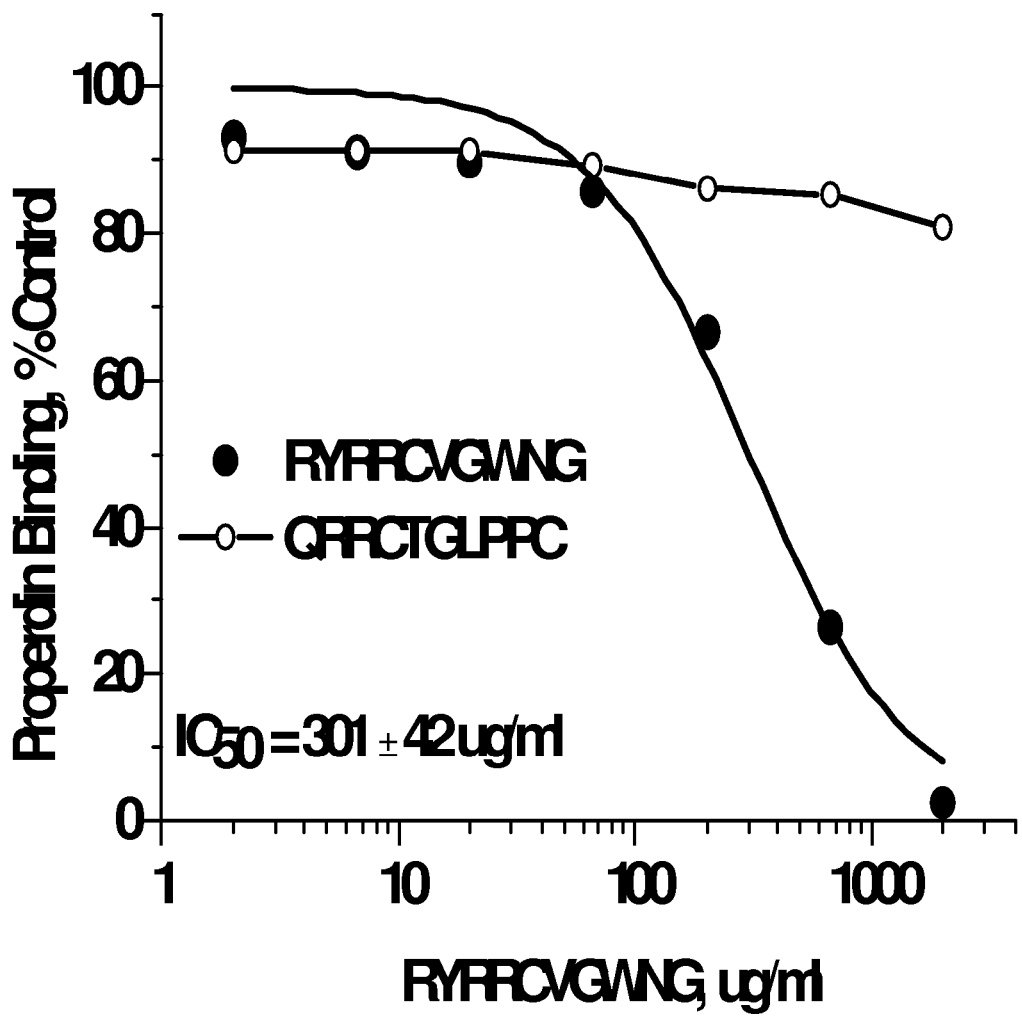
FIG. 8 shows the inhibition of properdin binding to C3b by RYRRCVGWNG (99-108) (SEQ ID NO: 5) but not by QRRCTGLPPC peptide (245-254) (SEQ ID NO: 6) from the TSR region. This TSR 3 peptide was shown by the previous publications to be inhibitory. The line marked with filled circles represents the RYRRCVGWNG (SEQ ID NO: 5) and the open circles show the QRRCTGLPPC (SEQ ID NO: 6). The Y-axis represents the reactivity of the peptide with C3b expressed as optical density (OD) at 450 nm and the X-axis represents the concentration of the peptide.

FIG. 7 shows that RYRRCVGWNG (SEQ ID NO: 5) peptide inhibits MAC formation in a dose dependent fashion with an IC50 of nearly 50 µg/ml, higher concentrations were not tested. FIG. 8 shows that the same peptide is also effective at inhibiting properdin binding to C3b. The rationale for the large concentration of peptide necessary to inhibit is the fact that these peptides are very small in length and do not possess the native conformation of the original protein thus excess peptide is required to observe inhibitory effects. Another peptide taken from a region of properdin sequence does not inhibit properdin binding to C3b. Taken together, Example 1 and Example 2 show that only two peptides specifically inhibit properdin binding to C3b in a dose dependent manner and clearly suggest that it is the segment $^{71\text{-}110}$ that may be involved in AP activation.

Example 3

Properdin Peptide (LCQPCRSPRWSLWSTWAPCSVTCSEGSQLR-YRRCVGWNGQ) (SEQ ID NO: 2) Inhibits Alternative Pathway Activation in Rabbit Erythrocyte Hemolysis A peptide ($^{71\text{-}110}$) was assembled that contains both small peptides shown in Examples 1 and 2. The rationale for synthesizing the peptide was the results obtained on the two peptides. We postulated that the synthetic peptide Peptide ($^{71\text{-}110}$) would inhibit AP activation of properdin binding to C3b. We also synthesized additional peptides corresponding to TSR5 and TSR6. All three peptides were evaluated in an alternative pathway dependent C5b-9 assay and properdin binding to C3b assay. In these assays we used a cell based C5b-9 assays instead of LPS based AP activation assay purely due to convenience.

Erythrocytes initiate the alternative complement cascade in human serum, and the resulting formation of MAC causes lysis of these cells. If properdin is essential to alternative pathway activity, then addition of the L-G blocking peptide to rabbit erythrocytes bathed in human serum should prevent cellular lysis. This can be assayed by examining the light scattering caused by intact red blood cells; lysed cells do not diffract light, and there is a consequent reduction in scattered light. It is well established that rabbit erythrocytes specifically activate the complement alternative pathway, with a resulting lysis of the cells by the C5b-9 complex. TSR-1 peptide at various concentrations in Gelatin Veronal buffer (Complement Technology) with 10 mM MgCl$_2$ and 10 mM EGTA, was incubated with 37° C. with a fixed number of rabbit erythrocytes (Covance) and with 10% normal human serum. A progressive decrease in light scatter (due to lysis of intact cells) was measured at 700 nm as a function of time in a temperature-controlled ELISA plate reader. The data were recorded and analyzed with a SpectraMax 190 plate reader and SoftMax Pro software and the results were plotted with MicroCal Origin Software.

Properdin-C3b Binding Assay: Polystyrene microtiter plates (Corning, Cat.) were coated with C3b protein (1.0 µg/50 µl per well) in PBS (Phosphate Buffered Saline) overnight at 4° C. After aspirating the C3b protein, the wells were blocked with 1% BSA in PBS for 2 hours at room temperature. Wells without C3b coating served as background controls. C3b coated wells were incubated with 5 nM properdin containing various concentrations of the synthetic peptide LCQPCRSPRWSLWSTWAPCSVTCSEGSQLRYRRCVG-WNGQ (SEQ ID NO: 2) in blocking solution. The samples were added to the wells. Following a 2 hour incubation at room temperature, the wells were rinsed five with PBS. C3b bound properdin was measured by adding anti-human properdin monoclonal antibody P#2 at 1:2000 dilution in blocking solution. The plate was allowed to incubate for 1 hour at room temperature. After washing the plates with PBS, a peroxidase-conjugated goat anti-mouse antibody (1:2000 dilution in blocking solution) was added and allowed to incubate for 1 hour. The plate was again rinsed thoroughly with PBS, and 100 µl of TMB substrate was added. The blue color reaction of TMB was quenched by the addition of 100 µl of phosphoric acid, and the plate was read at 450 nm in a microplate reader.

FIG. 9 shows that the combined sequence inhibits C5b-9 formation (AP activation) in an rRBC assay. The absence of full inhibition by the peptide in large part may be because of concentration of the peptide and peptide not being in a correct conformation. The fact that the large peptide inhibited hemolysis of rRBC in a dose dependent fashion clearly suggests that it is this segment of the peptide that is responsible for much of the binding. Peptides TSR5 and TSR6 demonstrated no inhibition of C5b-9 formation.

Figure 10:
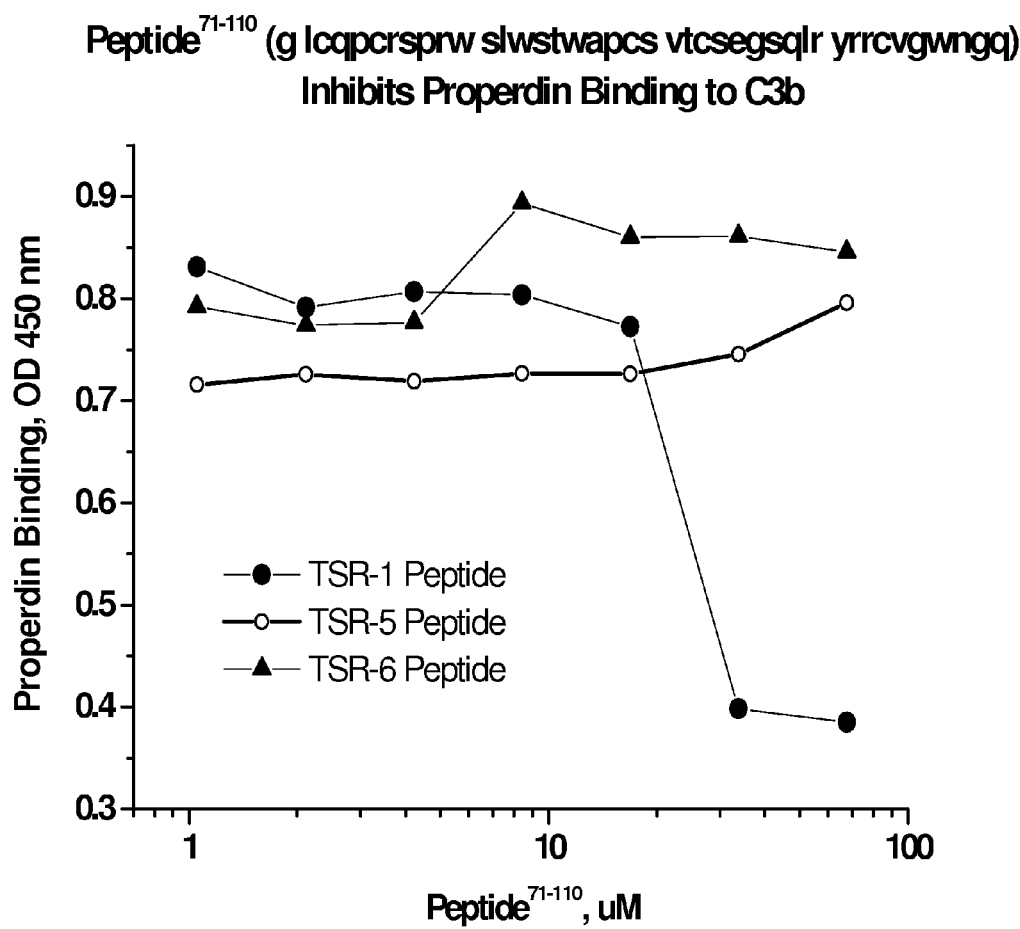
FIG. 10 shows the binding of peptide (71-110) (SEQ ID NO: 2) to substrate-bound C3b with TSR1 peptide (69-110) (SEQ ID NO: 2), TSR5 and TSR6 segments of properdin. The Y-axis represents the inhibition of binding.

FIG. 10 shows that the peptide inhibits properdin binding to C3b. These data are in perfect agreement with those presented in FIG. 7. It is thus clear that the mechanism of AP activation by properdin resides in various domains of the native properdin molecule. The domain we discovered appears to be unique for developing agents that would inhibit properdin function.

Example 4

Identification of MoAb that Binds Peptide $^{71\text{-}110}$LCQPCRSPRWSLWS TWAPCSVTCSEGSQLRYRRCVGWNGQ (SEQ ID NO: 2) Peptide Identified in Example 2

As noted throughout this patent application that several anti properdin monoclonal antibodies can be made that block AP activation via different mechanisms. Anti properdin monoclonal antibodies were generated using methods well known in the art. Antibody clones that specifically bind the peptide$^{71\text{-}110}$ were selected using the ELISA assay.

Screening Assay: Microtiter plates were coated with peptide$^{71\text{-}110}$. (2.0 µg/50 µl per well), TSR5 and TSR6 peptides in phosphate buffered saline (PBS) overnight at 4° C. After aspirating the peptide solutions, the wells were blocked with PBS containing 1% bovine serum albumin (BSA) for 2 hours at room temperature. Wells without peptide coating served as background controls. Aliquots of anti properdin monoclonal antibodies in blocking solution were added and plates were allowed to incubate for 1 hour to the peptide coated wells to allow antibody binding to the peptide. The plate was rinsed with PBS and the binding of the anti-properdin antibodies was detected 1:2000 dilution of HRPO labeled goat anti-mouse secondary at 1:2000 dilution in 1% BSA solution. The plate was incubated at room temperature for 1-hour. The plate developed using standard ELISA methods described above.

FIG. 11 shows that an anti properdin antibody clone binds the peptide$^{71-110}$ but not TSR5 and TSR6. The selected antibody clone MoAb$^{71-110}$ was grown in bulk and anti-properdin antibodies that bind the L-G were purified. The monoclonal antibodies that bind the region are the antibodies of this invention. These monoclonal antibodies do not bind the TSR5 and TSR6 used in these experiments.

Example 5

MoAb$^{71-110}$ Binds Human Properdin with High Affinity

The affinity of MoAb$^{71-110}$ to the peptide$^{71-110}$ peptide is a moderate binding affinity. A reasonable explanation of such binding is that the peptide may not be correctly folded. We then tested the binding affinity of the clone MoAb$^{71-110}$ to native protein properdin.

Polystyrene microtiter plates were coated with human (2.0 µg/50 µl per well) properdin in phosphate buffered saline (PBS) overnight at 4° C. After aspirating the properdin solution, the wells were blocked with PBS containing 1% bovine serum albumin (BSA) (Sigma-Aldrich, St. Louis, Mo.) for 2 hours at room temperature. Wells without peptide or properdin coating served as background controls. Aliquots of monoclonal anti properdin antibody clone MoAb$^{71-110}$ in blocking solution were added to the properdin coated wells and allowed to incubate for 1 hour to allow binding to occur. Following a 1 hour incubation at room temperature, the plate was rinsed with PBS five times and incubated with 1:2000 diluted anti-properdin polyclonal antibody.

Figure 12:
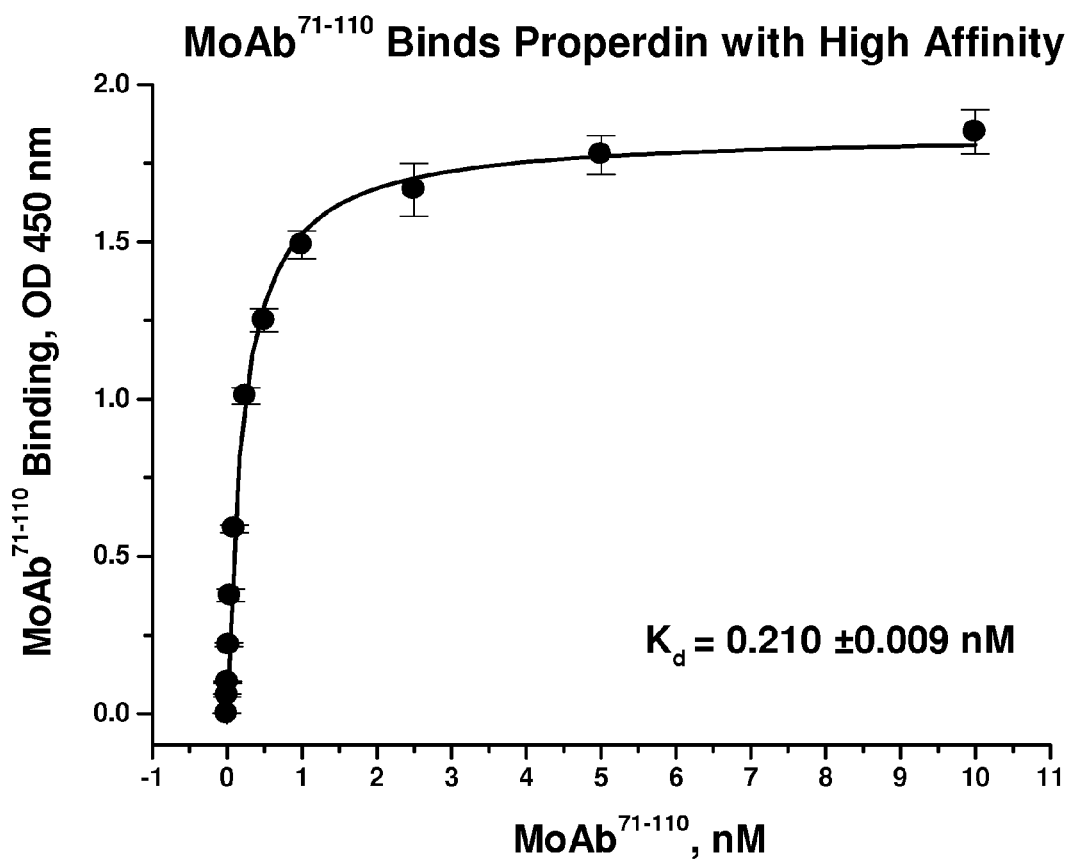
FIG. 12 shows the saturation binding of MoAb$^{71-110}$ to properdin. The binding of the monoclonal antibody is represented by the filled circles. The X-axis represents only the concentration of the monoclonal antibody MoAb$^{71-110}$.

As shown in FIG. 12, MoAb$^{71-110}$ binds properdin with high affinity. These affinity values are higher than those observed for the peptide $^{71-110}$ probably because the peptide is small and may not be folded properly like the native properdin. It is known that peptides may not adopt the original conformation.

Example 6

MoAb$^{71-110}$ does not Inhibit the Classical Pathway Activation

Monoclonal antibody of the present invention are different than those previously discovered. These monoclonals do not inhibit the classical pathway which is important for host defense. Antibody sensitized sheep erythrocytes is incubated with Normal Human Serum in GVB, CP buffer The antigen-Antibody complex on the surface of the sheep cells activates the classical complement pathway. As a result erythrocyte lysis occurs. Classical pathway activation occurs in low concentration of serum. We tested 1% and 10% normal human serum. The higher concentration of serum were used because we wanted to preserve the amplification loop.

In a typical assay, erythrocytes are incubated in 1% normal human serum in CP buffer to allow complement activation to occur. As a result of CP activation, C5b-9 is formed on the surface of erythrocytes causing cellular lysis. The progressive decrease in light scattering is measured at 700 nm as a function of time.

Figure 13:
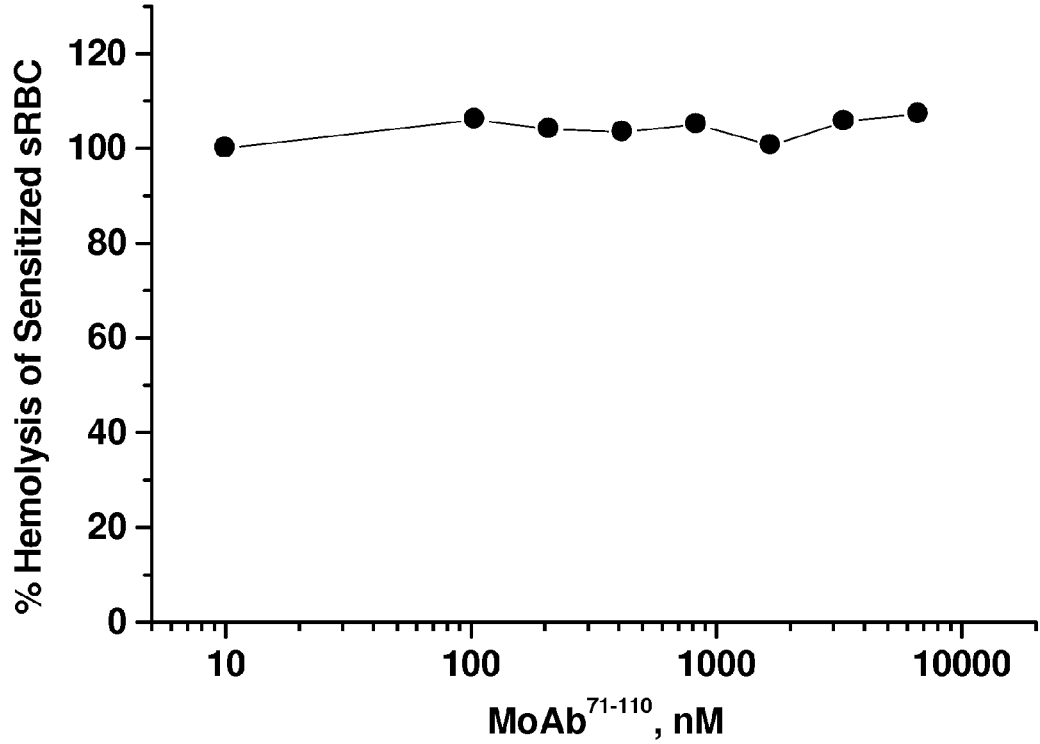
FIG. 13 shows that MoAb$^{71-110}$ does not inhibit the classical pathway dependent activation by antibody sensitized sheep cells in normal human serum. Antibody sensitized sheep cells activate the classical pathway in buffer containing Ca++/Mg++. Six different concentrations were evaluated in the hemolysis assay. MoAb$^{71-110}$ does not inhibit the classical complement pathway in normal human serum. Concentrations as high as 13.33 nM was tested in 1% serum which did not cause inhibition of CP mediated lysis.

As shown in FIG. 13, the MoAb$^{71-110}$ does not inhibit the classical complement pathway activation. These surprising results further suggest that antibodies can be made that inhibit the specifically prevent the AP activation without affecting the classical pathway. Previously discovered monoclonal antibodies to properdin are unknown to inhibit the both pathways of activation. Development of monoclonal antibodies of this invention will leave the classical pathway intact for host defense against infection.

Example 7

MoAb$^{71-110}$ Inhibits Alternative Pathway Rabbit Erythrocyte Lysis

This cellular assay is based on the formation of terminal complement complex on the surface of the rRBC. As a result, the rRBC are lysed. The evidence of lysed cells is reflected in progressive decrease in light scatter at 700 nm. rRBC are incubated in normal human serum in AP buffer. The surface of rRBC triggers the activation of AP in normal human serum. AP cascade begins and leads to the formation of C5b-9 complex on the surface of the rRBC. Agents that inhibit the activation are expected to inhibit cellular lysis.

To evaluate the effect of MoAb$^{71-110}$ on AP activation, various concentrations of MoAb$^{71-110}$ in AP buffer was incubated with normal human serum (10% NHS) at 37° C. with a fixed number of rabbit erythrocytes (Covance) in a temperature controlled ELISA plate reader capable of reading at 700 nm A progressive decrease in light scatter (due to lysis of intact cells) was measured at 700 nm as a function of time. The data were recorded and analyzed with a SpectraMax 190 plate reader and SoftMax Pro software. For calculation total inhibition was calculated at each concentration of the MoAb$^{71-110}$ and the results were expressed as a % of unlysed controls. Data at each concentration was plotted in a sigmoidal plot with MicroCal Origin Software.

Figure 14:
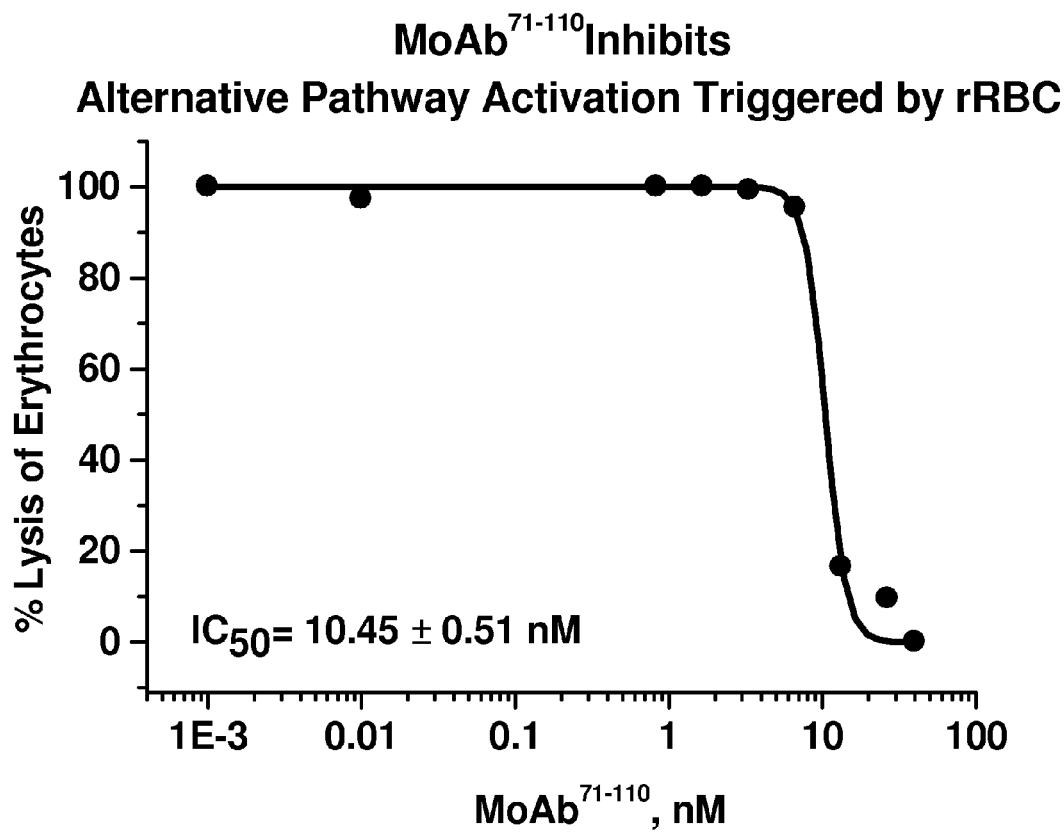
FIG. 14 shows the inhibition of alternative pathway dependent hemolysis of rabbit erythrocytes by MoAb$^{71-110}$ in normal human serum. Nine concentrations of the monoclonal antibody were tested as shown. No plasma and untreated plasma served as controls. Rabbit erythrocytes activate the alternative pathway in buffer containing Mg/EGTA. The monoclonal antibody inhibits the erythrocyte lysis with an IC$_{50}$ of 10 nM.
Figure 15:
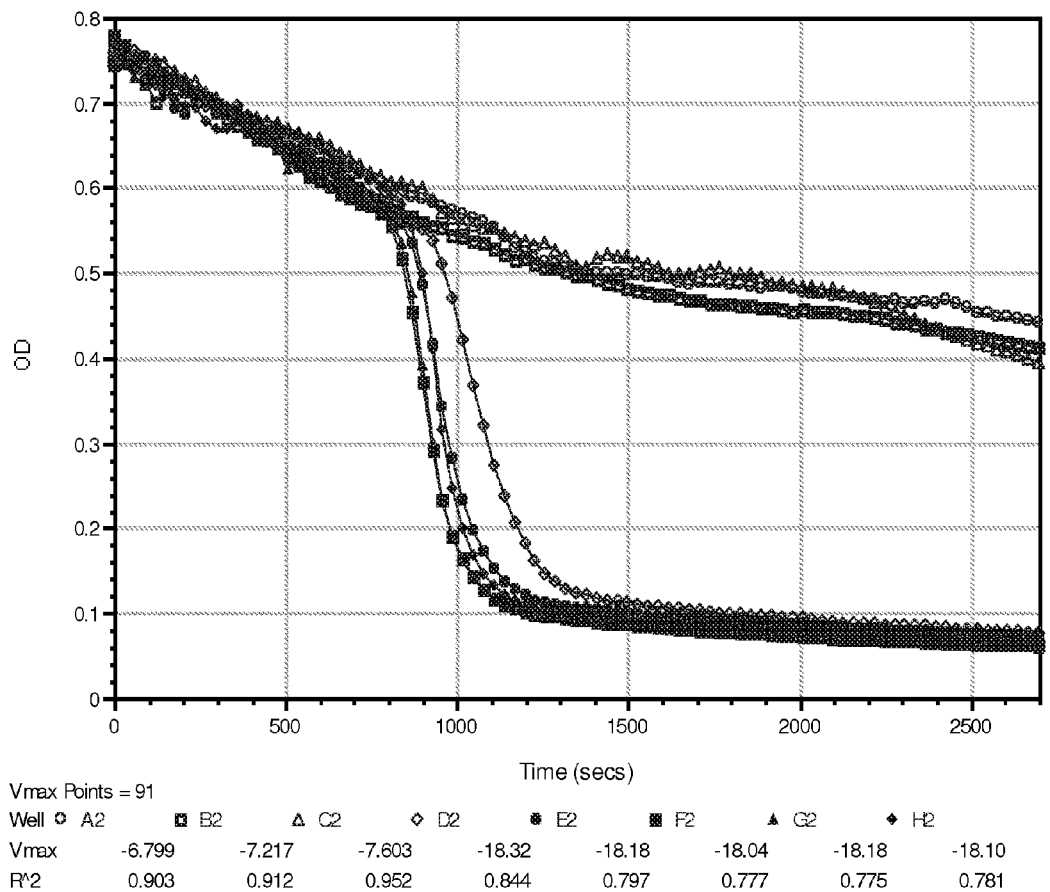
FIG. 15 shows the tracings for the data plotted in FIG. 14. These data show the dose curve analysis of kinetic measurements conducted on AP dependent rRBC hemolysis.

FIG. 14 demonstrates the potent activity of MoAb$^{71-110}$ in inhibiting erythrocyte lysis. The antibody is able to inhibit lysis with an IC50 of about 10 nM. As shown in FIG. 15, the original tracings from the spectramax show that the antibody inhibits lysis in a dose dependent manner. Data from each graph at the end point was taken and calculated the % inhibition of hemolysis. These data minor the data generated using in vitro graphs shown in Examples (2 to 6).

Example 8

MoAb$^{77-110}$ Inhibits AP Activation at a Ratio of Antibody to Properdin 1:1

This experiment was designed to determine the amount of antibody needed to inhibit the AP activation. Three donor serum samples were evaluated to gain statistically significant data. For each donor serum, assumptions were made on the concentration of properdin present in serum. Whole blood contains 200 nM properdin. Based on hematocrit of approximately 50%, the serum should contain 400 nM properdin. Thus, serum samples used contain 400 nM properdin for each of the three donors. The hemolysis was conducted in a final serum concentration of 100 nM, 50 nM, 40 nM, and 30 nM properdin. Correspondingly at each concentration of serum, various concentrations of MoAb$^{71-110}$ was tested for inhibition of AP activation using rRBC lysis assay. At each serum concentration, dose curve was generated with the blocking antibody. The IC$_{50}$ of inhibition was calculated and plotted against serum concentration. The data was fitted using a liner analyses.

Figure 16:
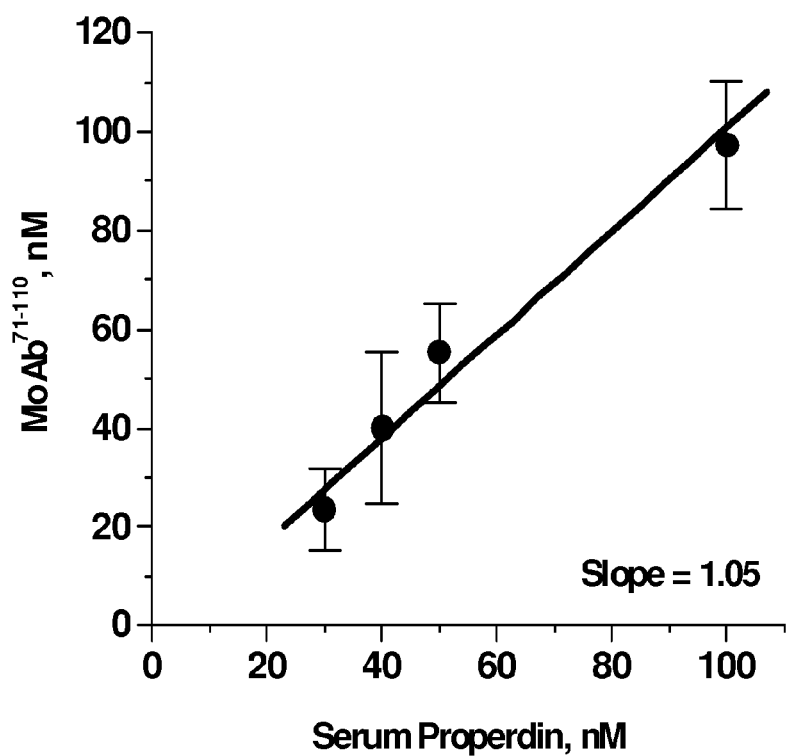
FIG. 16 shows that Monoclonal antibody to properdin ratio in plasma is 1:1. Molar equivalent concentrations were able to inhibit properdin function by 100%. Properdin in serum was based on literature value of 200 nM properdin whole blood. In Plasma, the concentration will be 400 nM because of near 50% average hematocrit. Normal human serum was diluted to 50%, 25%, 20%, and 15%. At each concentration antibody dose curves were generated. The IC$_{50}$ values were calculated as a % of serum. The values of nM antibody giving 50% inhibition were calculated. And plotted against properdin concentration. The same results were obtained for all three donors. The data was averaged and standard errors were calculated.

FIG. 16 demonstrates a linear relationship of the amount antibody and the concentration of properdin present in the serum. The linear fit analysis demonstrates that the slope of the line is about 1.00, indicating that the relationship of antibody to properdin binding is a 0.5:1, 1:1, 1.5:1 ratio.

Example 9

Factor B Preferentially Binds Properdin Bound C3b

It is known that Factor B binds C3b. It is also known that properdin binds C3b and that C3 convertase (PC3bBb) is stabilized in the presence of properdin. It has been debated whether properdin binds first or it only comes after the C3bBb convertase is already formed. We evaluated B binding to C3b and properdin bound C3b using ELISA based binding assays. It is known that if AP activation does not proceed, C3b begins to degrade by the action of factors H and I into iC3b, C3c, and C3dg. The conversion of C3b into smaller fragments is indicative of degradation route of C3b. It is assumed that in a given system at a given time, there would be some degraded C3b components could exist. We evaluated whether B would bind C3b and PC3b with different affinities. We also evaluated iC3b, C3c, and C3dg for factor B binding in the presence and absence of properdin.

Polystyrene microtiter plates were coated with human C3b, iC3b, C3c, or C3dg (1.0 µg/50 µl per well) in phosphate buffered saline (PBS) overnight at 4° C. After aspirating the protein, the wells were blocked with PBS containing 1% bovine serum albumin (BSA) for 2 hours at room temperature. Wells without coating served as background controls. In the plates without properdin, aliquots of factor B at varying concentration in AP buffer were added and plates were allowed to incubate for 2 hours. Factor B binding to the C3b and its fragments was measured by adding detection antibody (Quidel, San Diego, Calif., anti-human factor Bb antibody) at 1:2000 dilution in blocking solution. The plate was allowed to incubate for 1 hour at room temperature. After washing the plates with PBS, a peroxidase-conjugated goat anti-mouse antibody (1:2000 dilution in blocking solution) was added and allowed to incubate for 1 hour. The plate was again rinsed thoroughly with PBS, and 100 µl of 3,3',5,5'-tetramethyl benzidine (TMB) substrate was added. After incubation for 30 minutes at 25° C., the reaction of TMB was quenched by the addition of 100 µl of phosphoric acid, and the plate was read at 450 nm in a microplate reader.

In a separate experiment to evaluate the effect of the presence of properdin, an aliquot of properdin 5 nM was incubated for 1 hour in blocking solution on C3b coated plates. Following washing with PBS five times, various concentrations of factor B were added as above and the rest of the assay was performed as described above.

Figure 17:
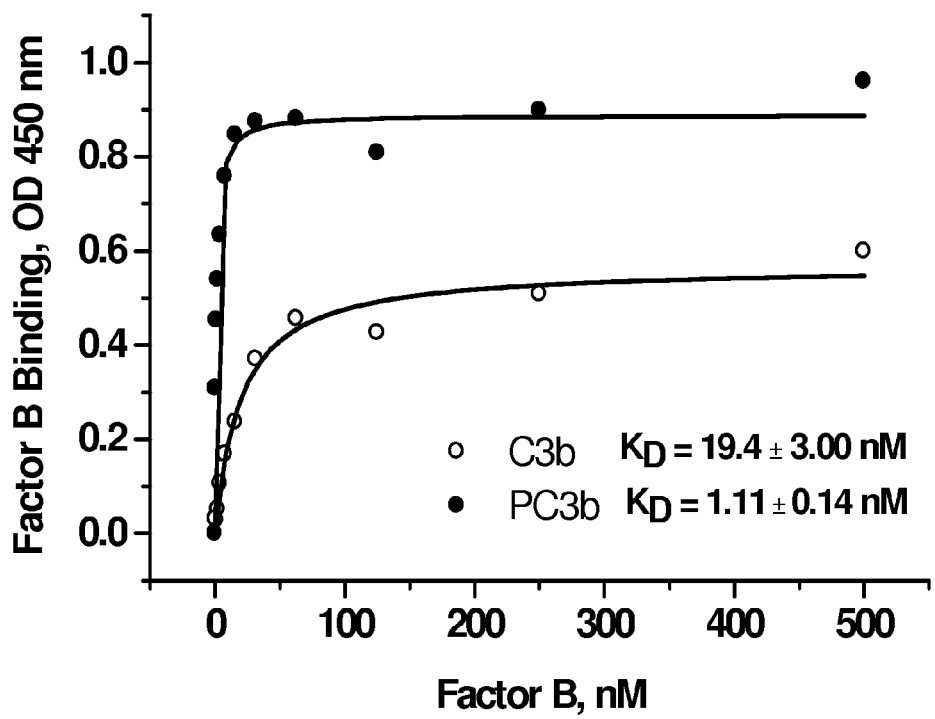
FIG. 17 shows that factor B binding to properdin bound C3b is high affinity compared to its binding to C3b. The difference in affinity is nearly 20-30 fold.
Figure 18:
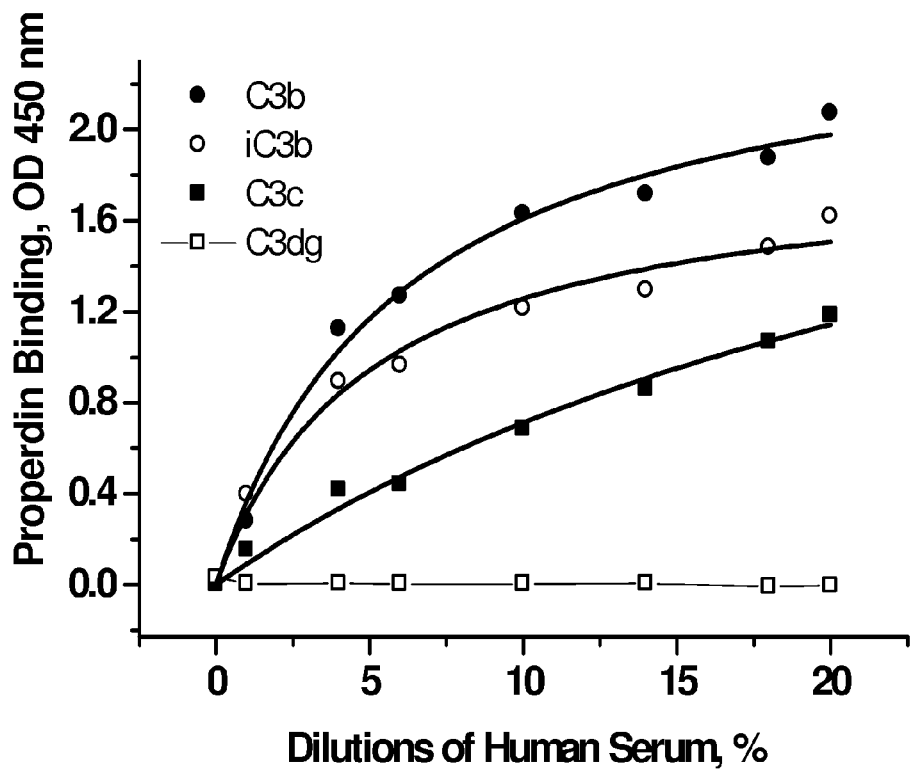
FIG. 18 shows that endogenous properdin does not bind C3dg fragment. Properdin binds C3b with high affinity compared to its binding to iC3b, and C3c.
Figure 19:
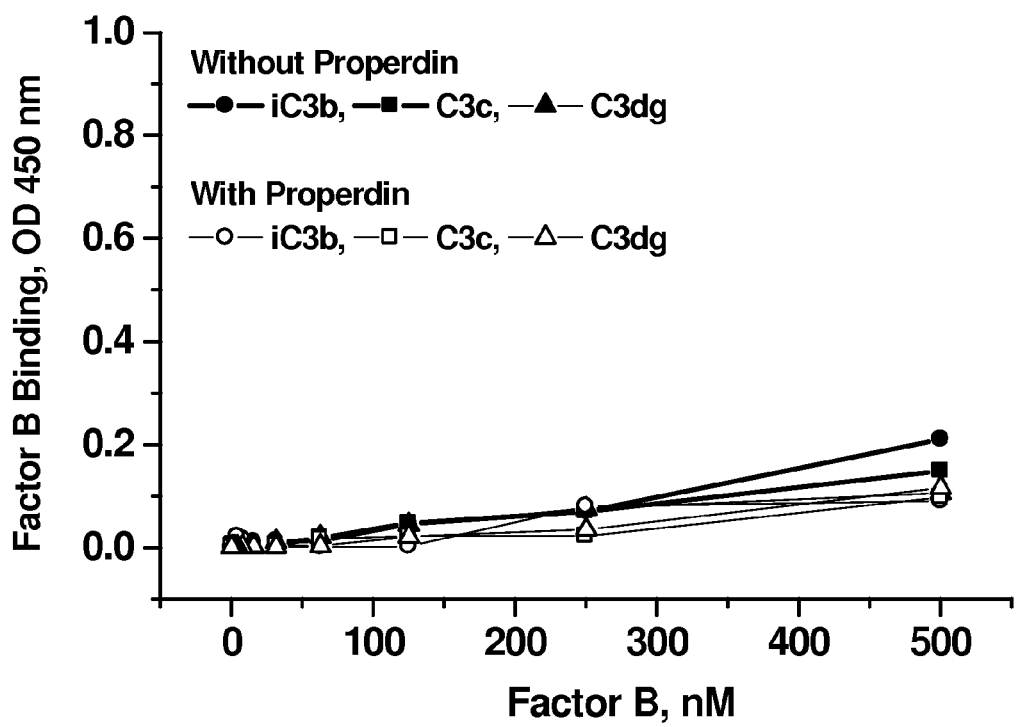
FIG. 19 shows that Factor B does not bind iC3b, C3c, and C3dg.

FIG. 17 demonstrates that factor B binds properdin bound C3b with high affinity compared to C3b that has no properdin binding. The difference in affinity were noted to be 20 fold higher properdin bound C3b. the affinity of properdin to C3b is 1.11 nM. The affinity of factor B to C3b is around 20-30 nM. The affinity of factor B is enhanced when factor P is present. We also evaluated if factor B bound properdin directly. It is clear from the direct binding experiments that factor B does not bind properdin. The lack of binding is in contrast to the findings of Farries et al. These experiments utilized Gel electrophoresis and an artificial synthetic linker to determine the binding, which could generate some artifacts. We evaluated the ability of MoAb$^{71-110}$ to inhibit the binding of properdin to C3bB complex. Factor B preferentially binds C3b and properdin bound C3b and demonstrates absolutely little or no binding to C3b degradation products. Thus, MoAb$^{71-110}$ would preferentially inhibit the binding of properdin bound C3bB complex. Properdin binds C3b, iC3b, C3c but does not bind C3dg as shown in FIG. 18. In contrary, Factor B only binds C3b but shows no binding to C3b, iC3b, C3c, C3dg as shown in FIG. 19. Lack of factor B binding to all these C3b fragments along with Properdin affinity being high for C3b+B complex explains the preferential binding and activation of the C3-convertase by the trimolecular high affinity complex (PC3bB). MoAb$^{71-110}$ inhibition of properdin binding to the C3bB complex is important instead of C3b alone.

Example 10

MoAb$^{71-110}$ Inhibits P Binding to C3b and C3bB

This assay demonstrates that the antibody of this invention is able to inhibit exogenous properdin binding to C3b and the C3bB complex.

Polystyrene microtiter plates were coated with human C3b (1.0 µg/50 µl per well) in phosphate buffered saline (PBS) overnight at 4° C. After aspirating the protein, the wells were blocked with PBS containing 1% bovine serum albumin (BSA) (Sigma-Aldrich, St. Louis, Mo., Cat. No. A7888) for 2 hours at room temperature. Wells without peptide or properdin coating served as background controls. Aliquots of the antibody at varying concentration in AP buffer containing 50 nM properdin were added and plates were allowed to incubate for 1 hour. Properdin bound to the C3b was measured by adding detection antibody goat anti-human properdin polyclonal antibody at 1:2000 dilutions in blocking solution. The plate was allowed to incubate for 1 hour at room temperature. After washing the plates with PBS, a peroxidase-conjugated rabbit anti-goat antibody (1:2000 dilution in blocking solution) was added and allowed to incubate for 1 hour. The plate was again rinsed thoroughly with PBS, and 100 µl of 3,3',5,5'-tetramethyl benzidine (TMB) substrate was added. After incubation for 30 minutes at 25° C., the reaction of TMB was quenched by the addition of 100 µl of phosphoric acid, and the plate was read at 450 nm in a microplate reader.

Factor B competition assay: Polystyrene microtiter plates were coated with human C3b (1.0 µg/50 µl per well) in phosphate buffered saline (PBS) overnight at 4° C. After aspirating the protein, the wells were blocked with PBS containing 1% bovine serum albumin (BSA) for 2 hours at room temperature. Wells without coating served as background control. Aliquots of the factor B at varying concentration of C3b in AP buffer containing 100 nM factor B were added and plates were allowed to incubate for 2 hours. Factor B bound to the C3b was measured by adding detection goat anti-human factor B polyclonal antibody) at 1:2000 dilution in blocking solution. The plate was allowed to incubate for 1 hour at room temperature. After washing the plates with PBS, a peroxidase-conjugated rabbit anti-goat:antibody (1:2000 dilution in blocking solution) was added and allowed to incubate for 1 hour. The plate was again rinsed thoroughly with PBS, and 100 µl of 3,3',5,5'-tetramethyl benzidine (TMB) substrate was added. After incubation for 30 minutes at 25° C., the reaction of TMB was quenched by the addition of 100 μl of phosphoric acid, and the plate was read at 450 nm in a microplate.

The inhibition of properdin binding to C3bB was performed as described above, with the only difference being that the plate was incubated with 100 nM of factor B in AP buffer for 1-hour prior to incubation of the antibody and properdin. The reason for this was to generate the C3bB complex on the plate before adding properdin to the plate.

Figure 20:
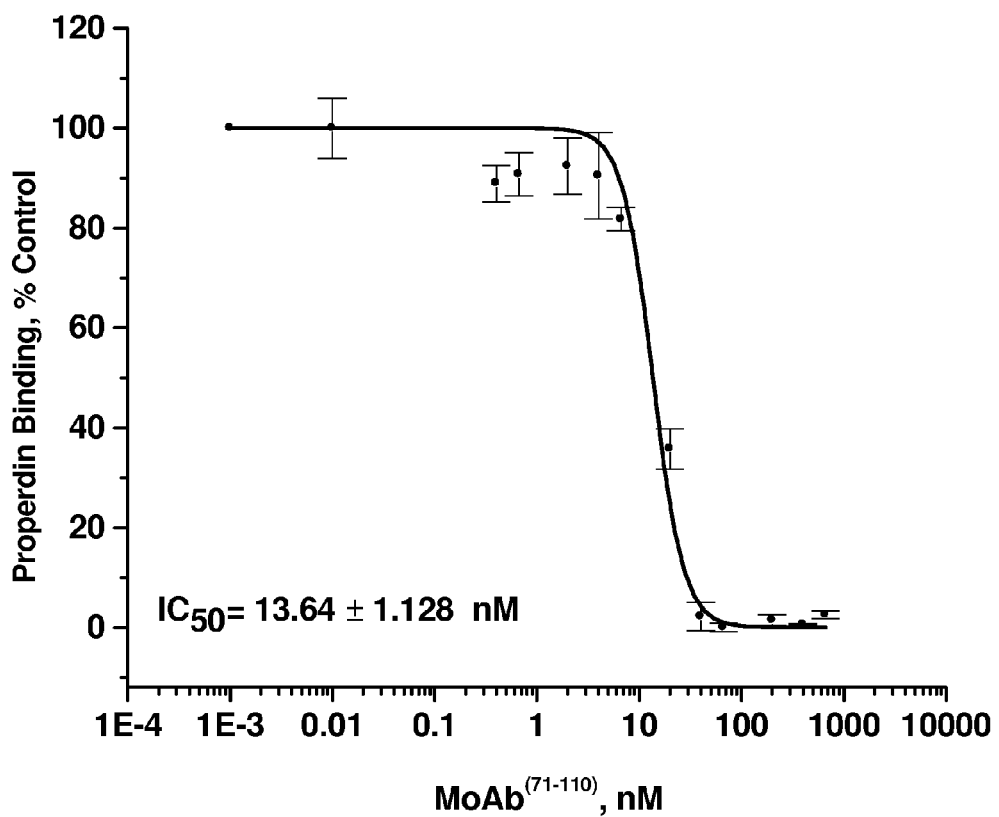
FIG. 20 illustrates inhibition of properdin binding to C3b by MoAb$^{71-110}$. The line marked with filled circles represents the inhibition curve of properdin to C3b binding. The inhibition curve is plotted based on the binding/inhibition of properdin to C3b. the X-axis represents the concentration of the monoclonal antibody MoAb$^{71-110}$.
Figure 21:
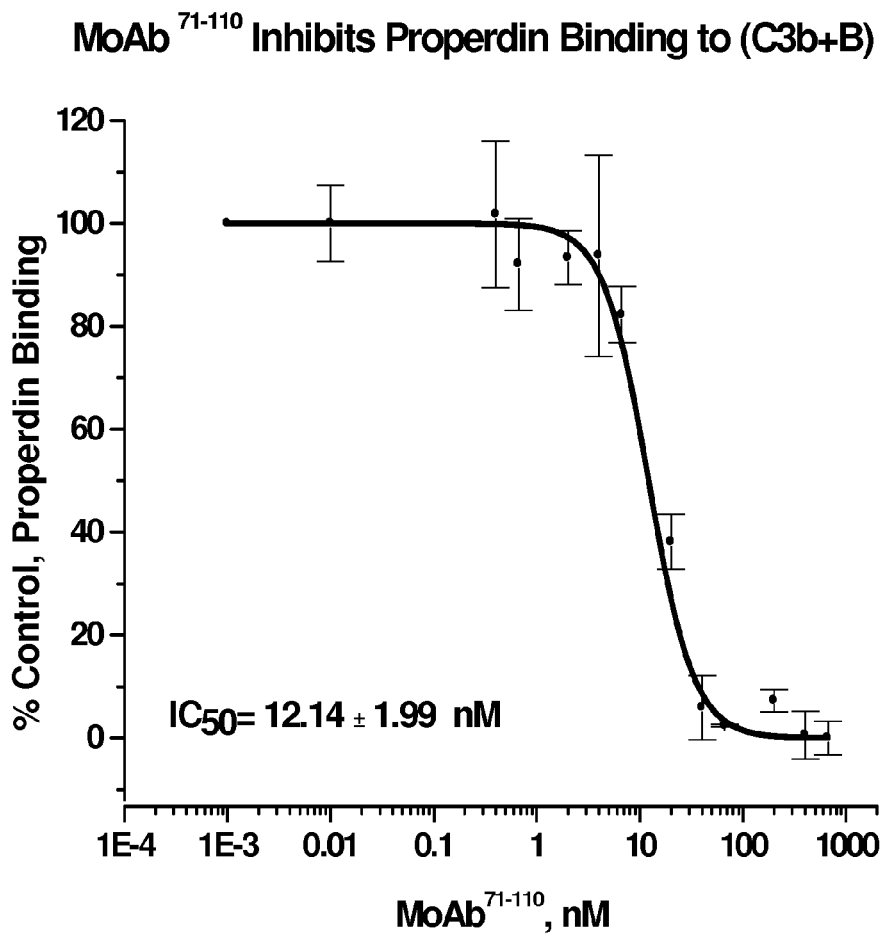
FIG. 21 illustrates inhibition of properdin binding to C3b+B complex by MoAb$^{71-110}$. The line marked with filled circles represents the inhibition curve of properdin to C3b+B binding. The inhibition curve is plotted based on the binding/inhibition of properdin to C3b. the X-axis represents the concentration of the monoclonal antibody MoAb$^{71-110}$.
Figure 22:
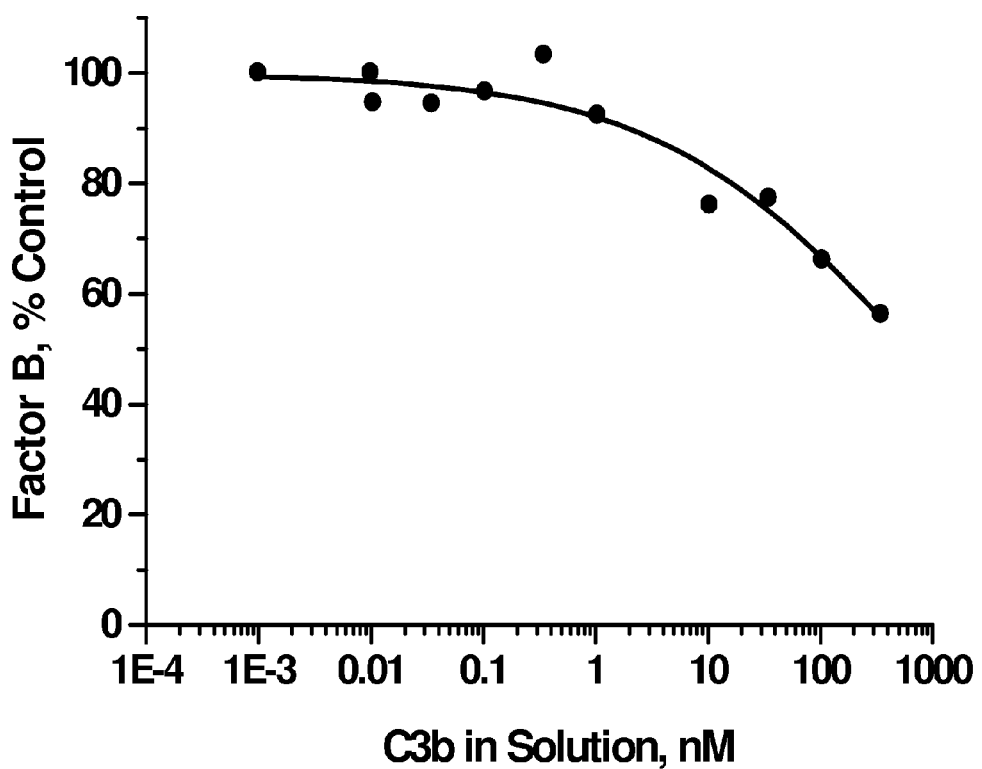
FIG. 22 illustrates inhibition of factor B Binding to C3b by solution phase C3b. These data suggests preferential binding of factor B to substrate-bound C3b.

As shown in FIG. 20, MoAb$^{71-110}$ inhibits the binding of properdin to C3b and FIG. 21 shows the inhibition of properdin binding to C3bB complex with similar affinities. As we showed in previous examples, factor B binding to properdin C3b complex is higher than C3b alone. As shown in FIG. 22, factor B preferentially binds substrate-bound C3b compared to soluble phase C3b. These data suggest that Factor B binding to C3b that would lead to C3-convertase activation is favored.

Example 11

Properdin Binds C3b with High Affinity, iC3b, C3c with Moderate Affinity and does not Bind C3 and C3dg Native C3 exists in solution at a very high concentration (1.3 mg/ml) in plasma and is the most abundant protein found in plasma. As a result of Tick over, a small fraction of C3 is converted into C3b. Properdin binds C3b with high affinity. Factor B also binds C3b with high affinity. Factor B does not bind solution phase C3b. Properdin binding to C3b is high affinity (2 nM), poor affinity was noted with iC3b, C3c and no binding was observed with C3dg. Based on the ratio of 1:1 with MoAb inhibition in plasma, it is easy to predict that all of the properdin binding is a productive binding. Because of high affinity of properdin to C3b compared to iC3b and C3c, it is concluded that inhibition of properdin association to C3bB is critical to inhibition of AP.

Polystyrene microtiter plates were coated with human C3b, iC3b, C3c, or C3d (1.0 μg/50 μl per well) in phosphate buffered saline (PBS) overnight at 4° C. After aspirating the protein, the wells were blocked with PBS containing 1% bovine serum albumin (BSA) for 2 hours at room temperature. Wells without coating served as background controls. Aliquots of human serum at varying concentration in AP buffer were added and plates were allowed to incubate for 2 hours. Properdin bound to the substrate coated C3b fragments was measured by adding detection antibody anti-human properdin monoclonal antibody at 1:1000 dilution in blocking solution. The plate was allowed to incubate for 1 hour at room temperature. After washing the plates with PBS, a peroxidase-conjugated goat anti-mouse antibody (1:1000 dilution in blocking solution) (Sigma Chemical Company) was added and allowed to incubate for 1 hour. The plate was again rinsed thoroughly with PBS, and 100 μl of 3,3',5,5'-tetramethyl benzidine (TMB) was added. After incubation for 30 minutes at 25° C., the reaction of TMB was quenched by the addition of 100 μl of phosphoric acid, and the plate was read at 450 nm in a microplate reader.

FIG. 18 demonstrates that properdin binds to C3b is the highest affinity compared to poor affinity to other C3b fragments. These data were generated using human serum and not free properdin. There appears to be no binds of properdin to C3dg. Since properdin binds C3b with high affinity and the complex drives the productive factor B binding to occur. Regardless of binding interactions, MoAb$^{71-110}$ binds and neutralizes properdin function.

Example 12

MoAb$^{71-110}$ Inhibits Factor D Activity as Shown by Inhibition of AP C3-Convertase Production The most important step in AP activation is the cleavage of Factor B by factor D. MoAb$^{71-110}$ prevents Factor D mediated cleavage of factor B. We have shown that AP activation does not occur in properdin depleted serum. Thus, properdin plays an important role in factor D mediated cleavage of factor B. In the absence of properdin factor D does not cut factor B to form C3 convertase. Direct binding experiments show that properdin binding to factor D is dose dependent (data not shown). It is likely that factor P functions as a cofactor for D. We set up an experiment in which Normal human serum in AP buffer is activated by LPS. As a result, AP is activated. AP activation proceeds via the formation of AP C3 convertase. We evaluated whether the MoAb$^{71-110}$ inhibits APC3 convertase. The total C3 convertase was detected with antibodies to properdin, C3b, and Bb. If all three are found deposited that means AP activation has occurred.

In a typical assay, wells of polystyrene microtiter plates were coated with LPS (Lipopolysaccharide from *Salmonella Typhosa*) 2 μg/50 μl in PBS overnight. The wells were incubated with 1% BSA in PBS to block the unoccupied sites on the plate. Following a 2-hour incubation at room temperature, the plate was rinsed once with PBS. Normal human serum (13.5%) in AP buffer was mixed with varying concentrations of the antibody and incubated with LPS coated wells. The plate was incubated for 2 hours 37° C. to allow complement AP activation to occur. Following incubation, the plates were extensively with PBS, and components of the C3 convertase were detected appropriately with antibodies. We detected C3b with rabbit anti-human C3c at 1:2000 in blocking solution, goat anti-human P at 1:2000 in blocking solution and Peroxidase labeled mouse anti-human Bb conjugate in blocking solution. The plates were incubated with their respective antibodies for 1-hour at room temperature. Following the incubation, the plates were rinsed with PBS and detected with peroxidase labeled goat anti-rabbit at 1:2000 for C3b and peroxidase labeled Rabbit anti-goat at 1:2000 in blocking solution for P detection. All plates were developed with TMB following extensive washing with PBS. The blue color was quenched with 1 M orthophosphoric acid. All three C3b, P and Bb together are indicative of AP C3 convertase formation.

In a separate experiment, C5b-9 was detected with goat anti-mouse neo sC5b-9 conjugate. These data are indicative of C5b-9 formation.

Figure 23:
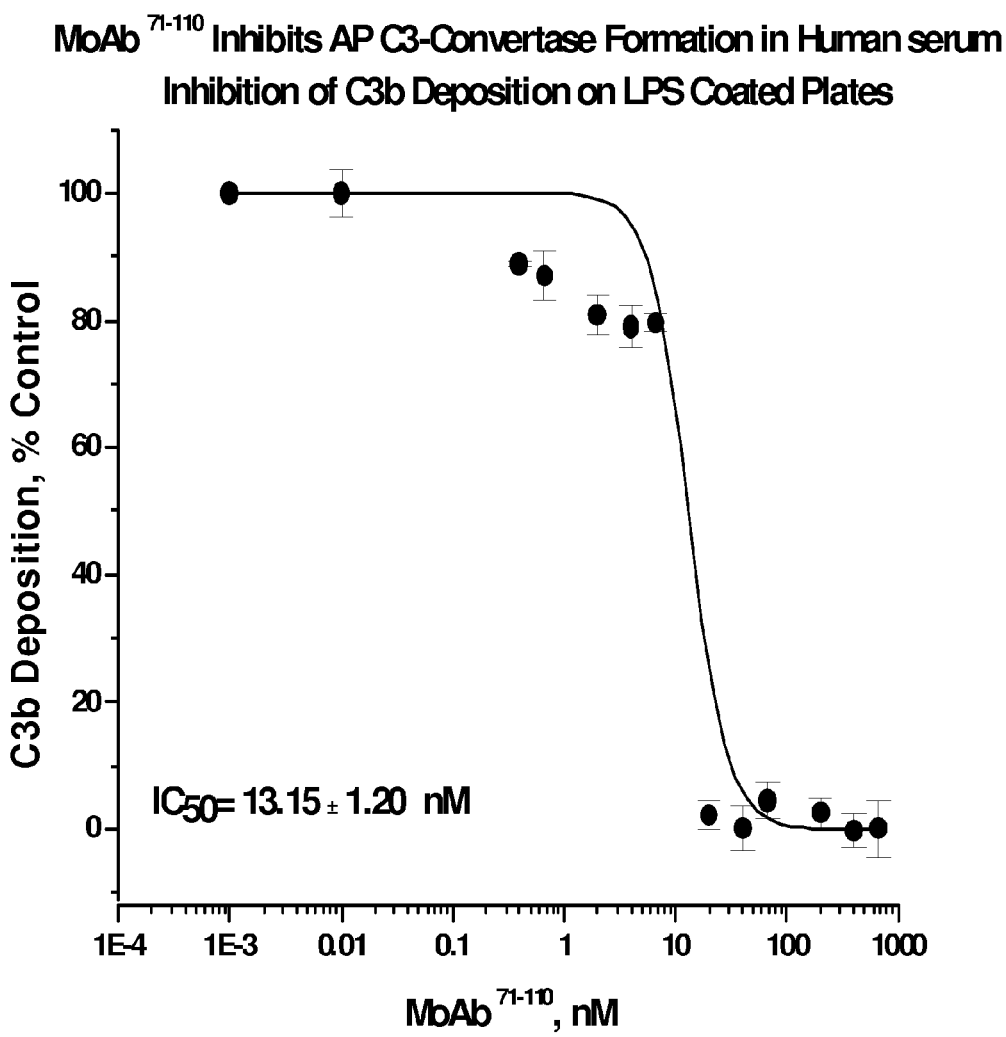
FIG. 23 illustrates inhibition of AP dependent C3 convertase in Normal human serum activated by the LPS coated plates. The MoAb$^{71-110}$ inhibits C3b formation as indicated by the lack of C3b deposition.
Figure 24:
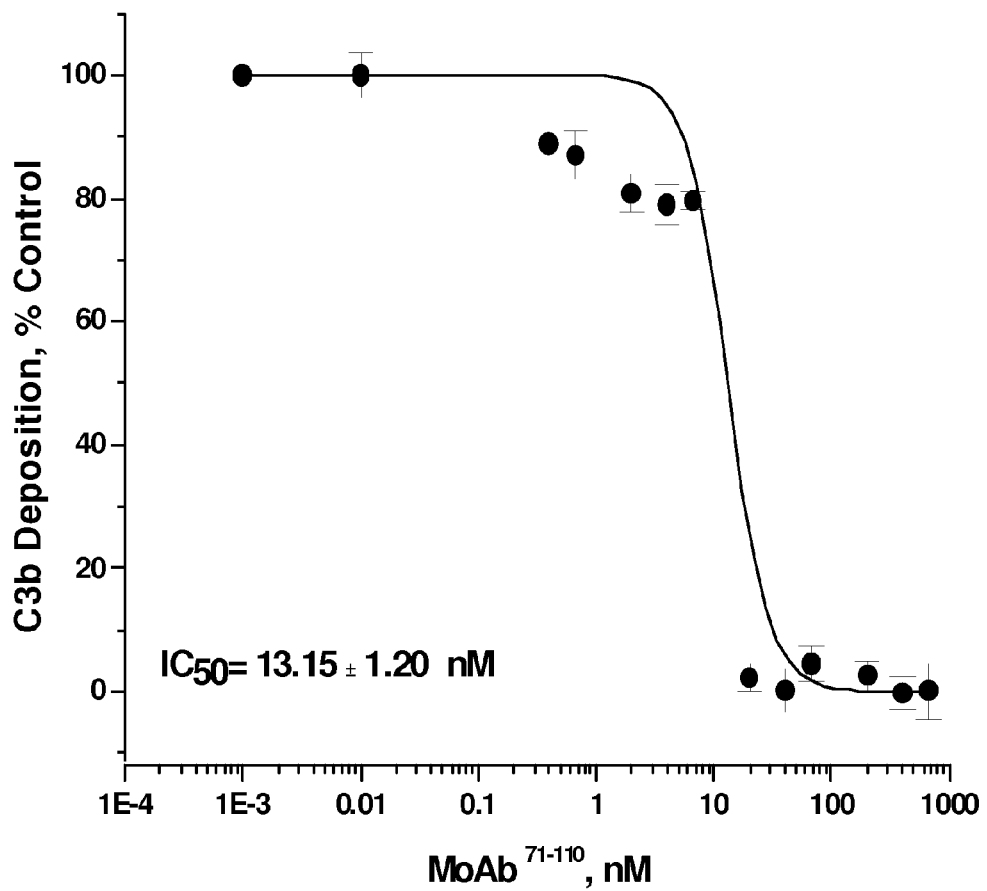
FIG. 24 inhibition of AP dependent C3 convertase in normal human serum activated by the LPS coated plates. The MoAb$^{71-110}$ inhibits properdin deposition.
Figure 25:
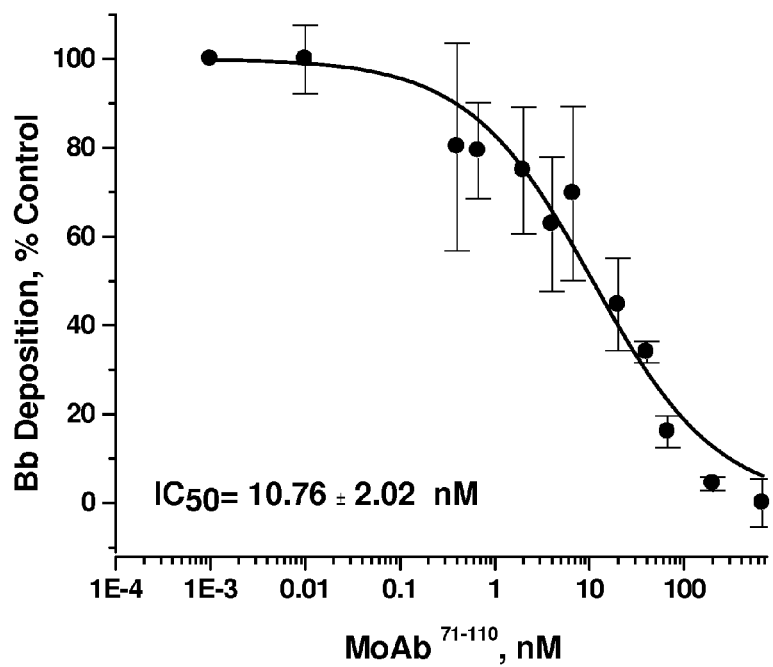
FIG. 25 illustrates inhibition of AP dependent C3 convertase in normal human serum activated by the LPS coated plates. The MoAb$^{71-110}$ inhibits Bb formation as indicated by the lack of Bb deposition.
Figure 26:
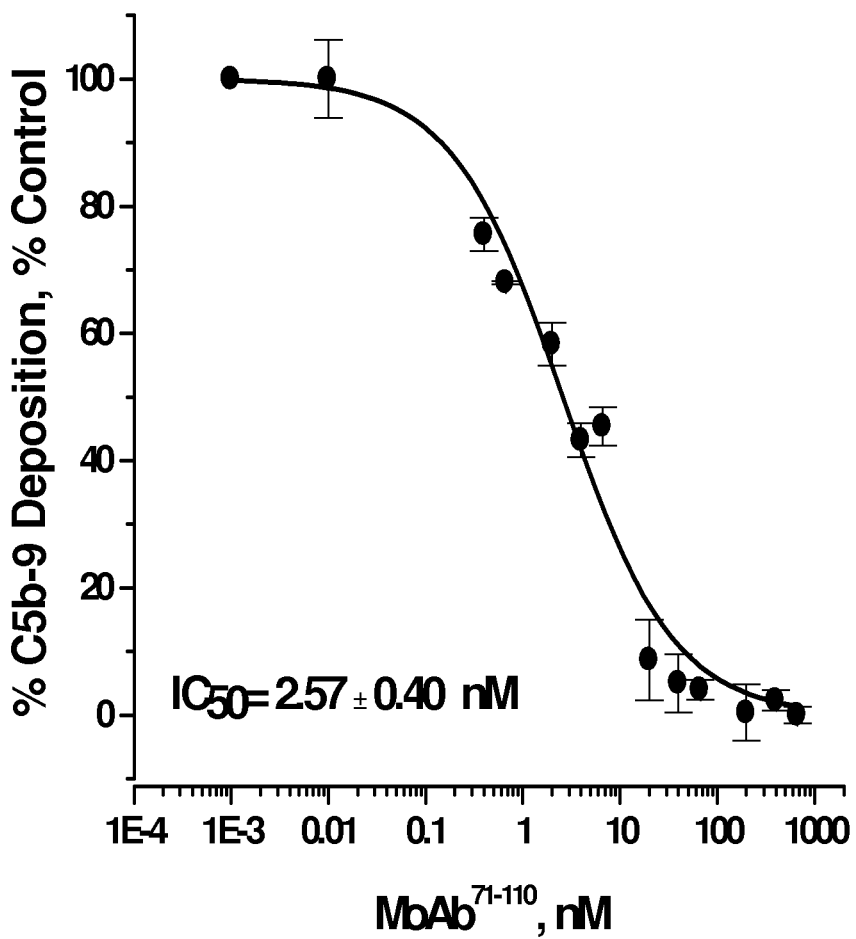
FIG. 26 illustrates inhibition of C5b-9 formation by MoAb$^{71-110}$. The line marked with filled circle represents the inhibition of C5b-9 deposition onto LPS coated surface. MoAb$^{71-110}$ inhibits the LPS mediated activation of C5b-9 deposition. The X-axis refers to the concentration of the MoAb$^{71-110}$ that causes inhibition of C5b-9 formation.

FIG. 23 demonstrates a dose dependent inhibition of C3b formation with highest inhibition being seen at highest concentration of the MoAb$^{71-110}$. FIG. 24 demonstrates the dose dependent inhibition of properdin deposition. These data suggest that lack of C3b formation means no properdin deposition. FIG. 25 demonstrates that Bb is not deposited in a dose dependent manner and that the highest concentration of MoAb$^{71-110}$ causes maximum inhibition of Bb deposition. These data provide direct evidence that MoAb$^{71-110}$ halted the production of C3 convertase. FIG. 26 shows that MoAb71-110 inhibits C5b-9 formation by inhibiting the C3 convertase formation. These data indirectly support the idea of MoAb$^{71-110}$ inhibiting factor D activity on factor B.

Example 13

MoAb71-110 Inhibits Complement Activation in Whole Blood Model of Cardiopulmonary Bypass The tubing loop model is a representative model to demonstrate alternative complement pathway mediated activation. The present model would evaluate AP activation in situations where blood comes in contact with the artificial surfaces. This model closely mimics the complement activation that is observed during extracorporeal circulation. The tubing loop experiment was performed by collecting fresh blood from a healthy donor using IRB approved guidelines. The blood was collected into 50 mL polypropylene conical tubes containing 5 units/ml of heparin (porcine mucosa) as an anticoagulant. The blood was added to the tubes preloaded with plasmalyte 148 containing various concentrations of MoAb$^{71-110}$. A 1.8 ml of this diluted blood containing the appropriate concentrations of the MoAb$^{71-110}$ were added to poly vinyl chloride (PVC) tubings (PE 330; I.D., 2.92 mm; O.D., 3.73 mm; Clay Adams, N.J.). The tubings were closed into a loop and subjected to a vertical rotation for at least 2-3 hours at 37° C. After incubation, blood samples were transferred into 2.0 ml tubes. Blood aliquots for flow cytometry were acquired. The remaining blood samples were centrifuged (4000.times.g for 5 minutes at 4° C.) and the plasma were collected. The plasma samples were evaluated for complement activity utilizing C3a & C5b-9 kits (Quidel), C5a kits (BD-Pharmingen), and the rabbit erythrocyte lysis assay. The rabbit erythrocyte lysis was performed as described in previous examples with the only major difference being that tubing loop plasma samples were dilute 1:1 and then added to rabbit erythrocytes.

Figure 27:
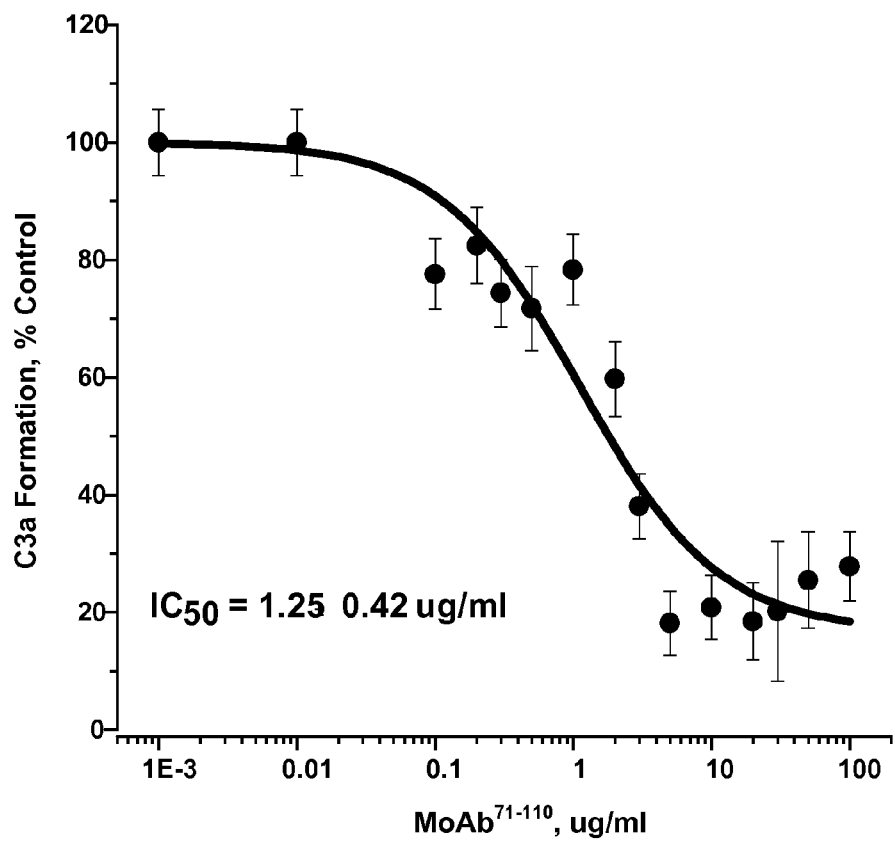
FIG. 27 illustrates MoAb$^{71-110}$ inhibits C3a formation during extracorporeal circulation of whole human blood. As described in example 13, MoAb$^{71-110}$ at various doses was evaluated for inhibition of C3a formation in a tubing loop model of cardiopulmonary bypass.

As a result of AP activation, C3-convertase forms, which cleaves C3 into C3a and C3b. C3a is a potent anaphylatoxin activates neutrophils, monocytes, and lymphocytes. During the tubing loop process, the alternative pathway is activated and results in the formation of C3 convertase, which causes the formation of C3a. FIG. 27 demonstrates that inhibition of the alternative pathway results in a dose dependent inhibition of C3a formation with complete inhibition observed at about 10 ug/ml.

Figure 28:
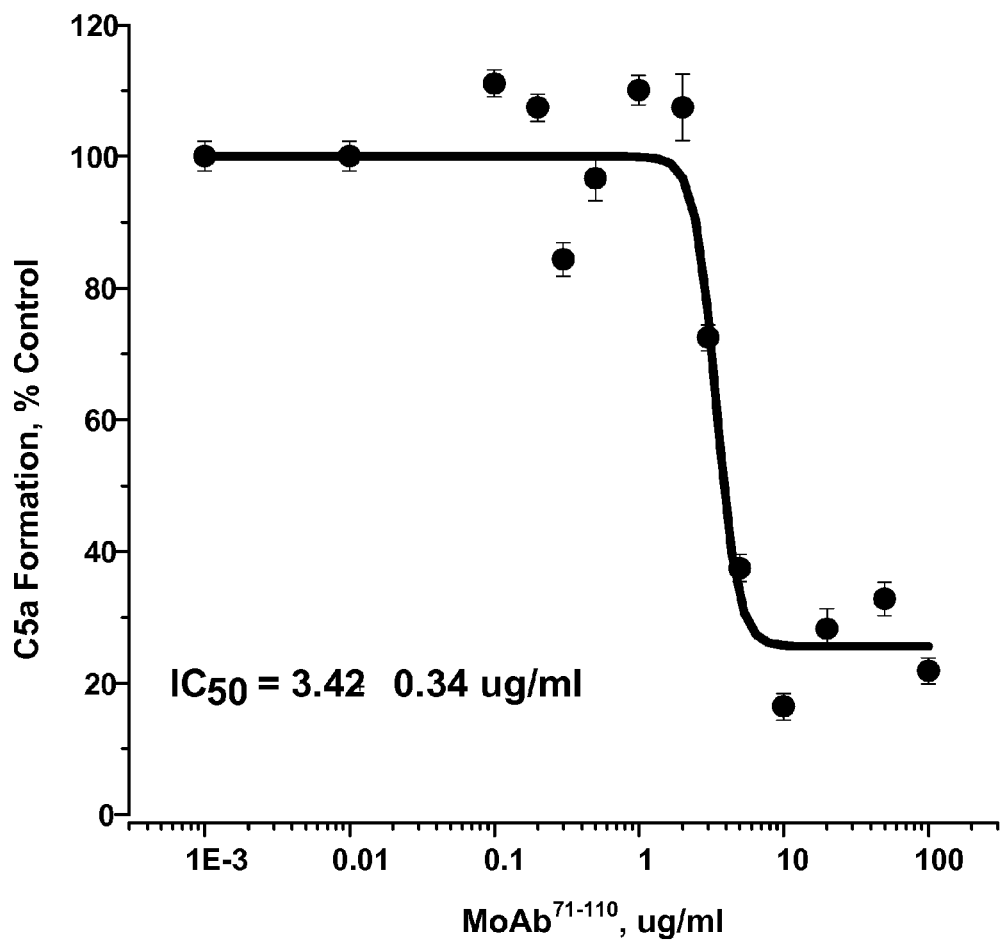
FIG. 28 illustrates MoAb$^{71-110}$ inhibits C5a Formation during Extracorporeal Circulation of Whole Human Blood. Plasma from the tubing loop method was also evaluated for C5a formation as describe in example 13.

C5a is another potent anaphylatoxin that is responsible for activating many inflammatory cells. C5a is produced by C3-convertase cleavage of C5 into C5a and C5a. As demonstrated by FIG. 28, MoAb$^{71-110}$ dose dependently inhibits C5a generation with complete inhibition at about 10 ug/ml. This number corresponds with the C3a results with complete inhibition at about 10 μg/ml which indicates that MoAb$^{71-110}$ is able effectively inhibit C3 convertase function.

Figure 29:
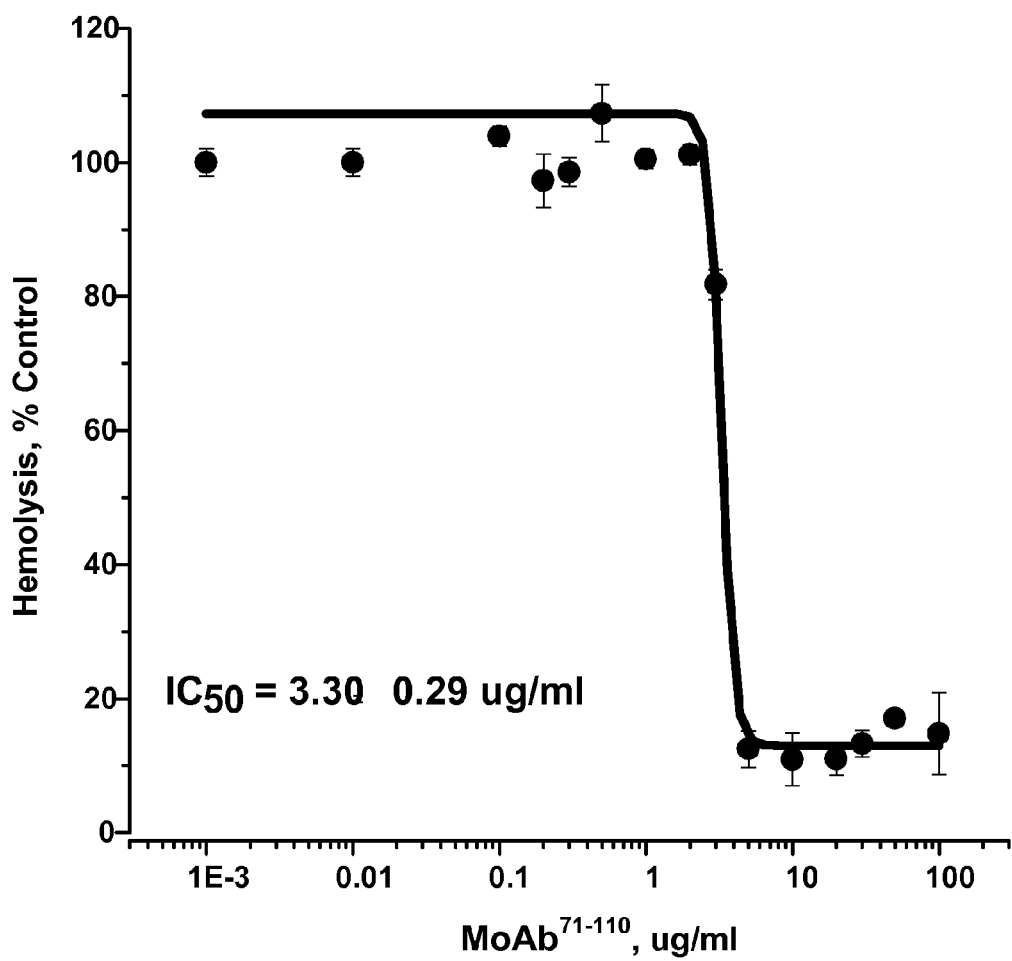
FIG. 29 illustrates MoAb$^{71-110}$ inhibits C5b-9 formation during extracorporeal circulation of whole blood as evidenced by the Hemolysis Assay. C5b-9 is the terminal component of the complement cascade and is known as the membrane attack complex. According to the FIG. 29, treatment of MoAb$^{71-110}$ dose dependently inhibits C5b-9 formation with complete inhibition observed ~10 μg/ml.

C5b-9 is terminal component of the complement cascade and functions as a lytic pore-forming complex that deposits onto membranes and causes their lysis. The hemolysis assay makes use of this concept and the formation of C5b-9 deposits onto these cells and causes their lysis. MoAb$^{71-110}$ inhibits alternative pathway activity and thus prevents C5b-9 formation as demonstrated by FIG. 29. In this figure, MoAb$^{71-110}$ is able to inhibit dose dependently C5b-9 formation with complete inhibit observed at ~5-10 ug/ml. These numbers correspond with the values obtained from the C3a and C5a results.

Example 14

MoAb$^{71-110}$ Inhibits Cellular Activation in Whole Blood Model of Cardiopulmonary Bypass We have shown that MoAb$^{71-110}$ inhibits inflammatory mediators C3a and C5a. These molecules are potent activators of neutrophils, monocytes, and platelets. Receptors for C3a and C5a are known to be present on each of these cell types. In a tubing loop model of cardiopulmonary bypass we evaluated the ability of MoAb$^{71-110}$ to inhibit cellular activation. Using the tubing loop method as described in the example above, we evaluated the effect of MoAb$^{71-110}$ at various concentrations (0.5-100 ug/ml) on the effect of cellular activation. After the tubing loop process, an aliquot blood from the tubing loops was taken for flow cytometry analysis.

Aliquots of blood were stained with FITC-CD14 and PE-CD11b for monocytes, FITC-CD15 and PE-CD11b for neutrophils, and FITC-CD61 and PE-CD62P for platelets. Only 50 μl blood samples were labeled. Following a 20 min incubation at room temperature, 2 ml of FACS Lysing solution was added and the samples were incubated at room temperature for 20 min Samples were centrifuged for 5 min to pellet the cells. The supernatant is removed and the cells re-suspended in wash buffer (0.1% BSA in PBS/azide). The samples were re-centrifuged, the supernatant removed, and the cells re-suspended in 0.5 ml of 0.5% paraformaldehyde.

Figure 30:
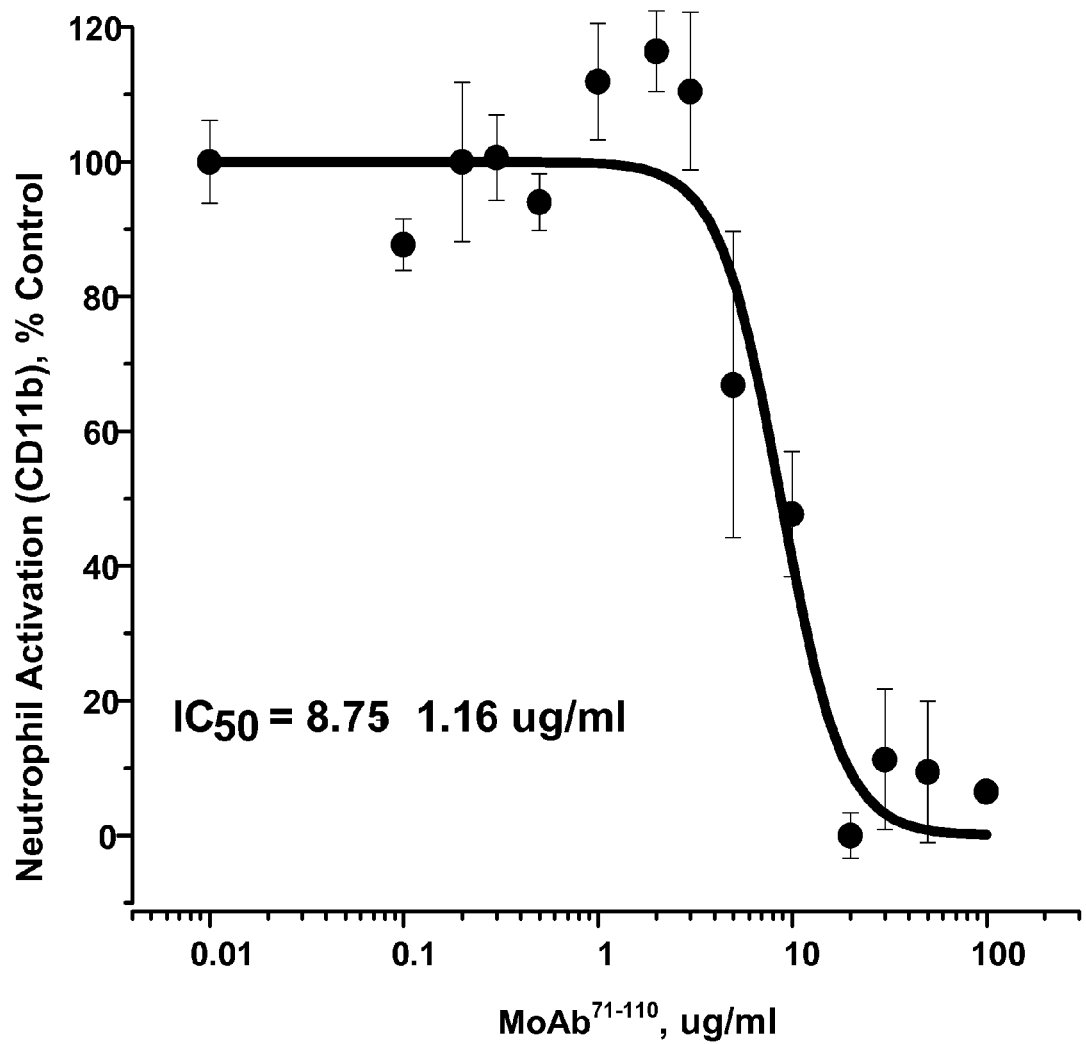
FIG. 30 illustrates MoAb$^{71-110}$ inhibits neutrophil activation during extracorporeal circulation of whole human blood. Aliquots of blood from the tubing loop method were evaluated using flow cytometry and the appropriate cellular activation markers. Neutrophils were evaluated using CD15-FITC and CD11b-PE antibodies. MoAb$^{71-110}$ effects on cellular activation were evaluated. This figure demonstrates dose dependent inhibition of MoAb$^{71-110}$ on neutrophil activation measure via CD11b expression. According to the figure, MoAb$^{71-110}$ demonstrates complete inhibition at ~10-20 μg/ml. These results coincide with the C3a and C5a results should be the case because C3a and C5a are potent activations of neutrophils.

Neutrophils are potent inflammatory cells capable of releasing several deleterious components that mediate the inflammatory response. As described above, MoAb$^{71-110}$ inhibits C3a and C5a formation during tubing loop. This anaphylatoxins are responsible for activation of neutrophils, monocytes, and platelets. Treatment with MoAb$^{71-110}$ demonstrates dose dependent inhibition of neutrophil activation as measured via CD11b expression with complete inhibition observed at about 10-20 μg/ml (FIG. 30). This corresponds very closely with the results obtained for inhibition of C3a and C5a formation as.

Figure 31:
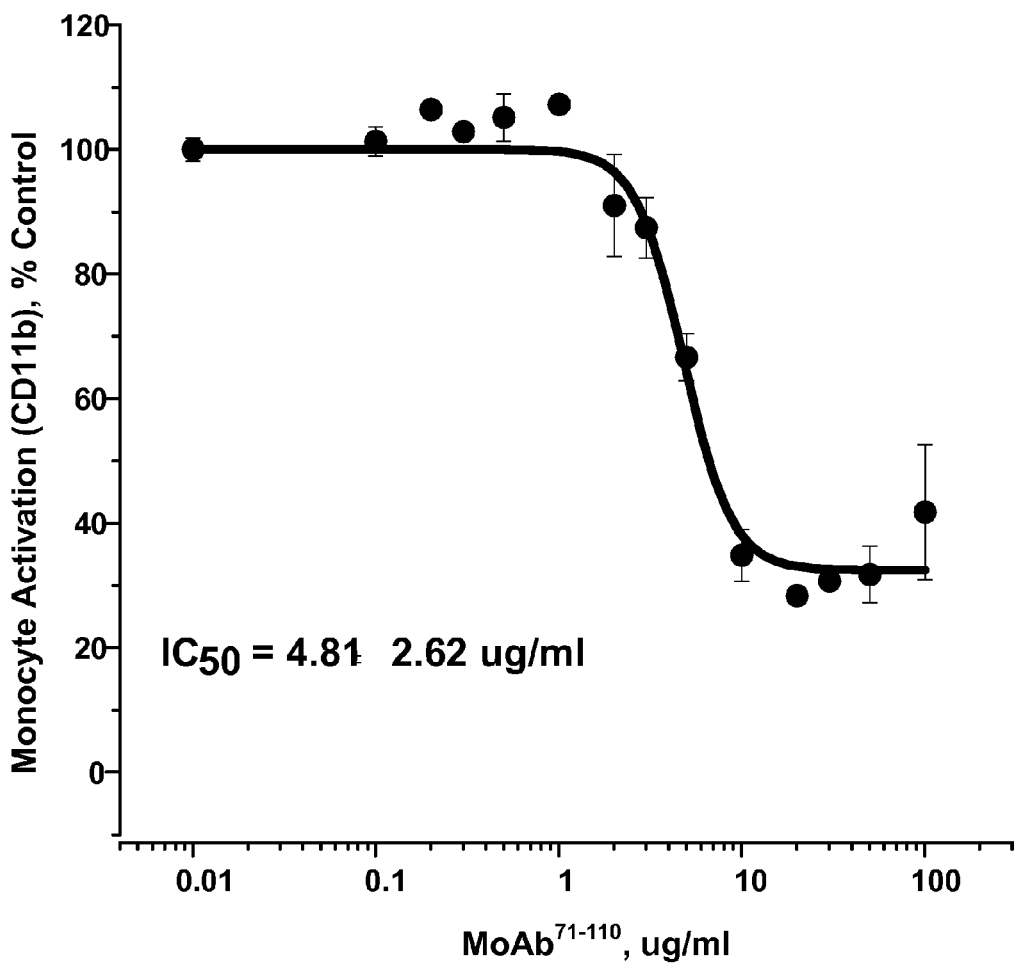
FIG. 31 illustrates MoAb$^{71-110}$ inhibits monocyte activation during extracorporeal circulation of whole human blood. Using the same principles as neutrophils, monocyte were stained with CD14-FITC and CD11b-PE. Monocyte activation was evaluated via CD11b expression. Treatment of MoAb$^{71-110}$ demonstrates dose dependent inhibition with complete inhibition observed at ~10 μg/ml.

Monocytes are another important inflammatory cell that is responsible for the mediating the inflammatory response. They are most notably known for the production of TNF-alpha, one of the most potent inflammatory cytokines. Monocytes are activated via binding of C3a and C5a to their respective receptors. Monocytes were evaluated with flow cytometry as described earlier in this example. Treatment with MoAb$^{71-110}$ demonstrates dose dependent inhibition of monocyte activation as measured via CD11b expression with complete inhibition observed at about 10 μg/ml (FIG. 31). This corresponds very closely with the results obtained for inhibition of C3a and C5a formation as well as the results from neutrophil inhibition.

Figure 32:
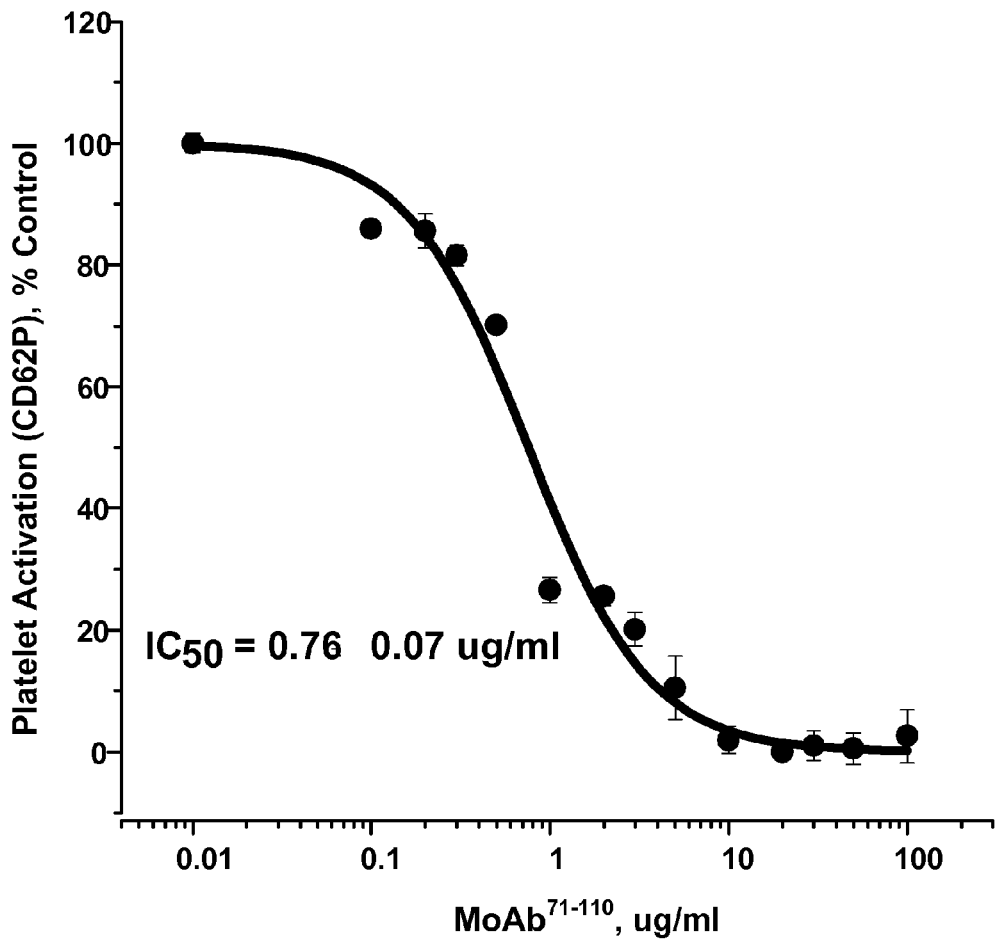
FIG. 32 illustrates MoAb$^{71-110}$ inhibits platelet activation during extracorporeal circulation of whole human blood. Using the same principles in FIGS. 27 and 28, platelet was measured using staining antibodies against platelet CD61-FITC and CD62P-PE. Platelet activation was evaluated by the level of CD62P expression. Treatment with MoAb$^{71-110}$ produced results similar those obtained for neutrophils and monocytes. The figure demonstrates dose dependent inhibition of Platelet activation by MoAb$^{71-110}$ with complete inhibition observed at ~10 μg/ml.

Platelets are activated via mechanisms similar to monocyte and neutrophil activation. However, platelets are not responsible for the inflammatory responses but are more important in regulating hemostasis. In cardiopulmonary bypass, platelet dysfunction leads to severe and complex bleeding complications. Prevention of platelet dysfunction is a critical aspect of developing therapeutics for cardiopulmonary bypass. Platelets were evaluated using flow cytometry described above using tubing loop samples. FIG. 32 demonstrates dose dependent inhibition of platelet activation measured via platelet activation marker CD62P. Complete inhibition is observed at about 10 μg/ml. These numbers are consistent with all other experiments.

Example 15

MoAb$^{71-110}$ Inhibits of Platelet-Leukocyte Aggregates in Whole Blood Model of Cardiopulmonary Bypass Aggregates have been found associated with several diseases. Activated platelets can form neutrophil-platelet and monocyte-platelet aggregates. Such aggregates have been implicated in cardiac related diseases. More specifically, monocyte-platelet conjugates have been shown to indicate a possibility of heart attack. Using flow cytometry approaches, we were able to measure the presence of platelet-leukocyte conjugates in blood that has undergone extracorporeal circulation. This method functions by evaluating the presence of platelets in the populations of neutrophil monocyte.

Neutrophil-Platelet aggregates were labeled with (FITC labeled CD61 (platelet body marker), and PE labeled CD15 (neutrophil body marker): A 50 µl aliquot of blood from the tubing loop (both control and treated) is immediately incubated with 20 µl of FITC-CD61 antibody and 20 µl of PE-CD15 antibody. Following 20 min incubation, 2 ml of FACS-Lying solution is added and the treated sample, which is then incubated at RT for 20 min FACS Lyse causes red blood cell lysis and at the same time, fixes the labeled leukocytes. Samples were centrifuged at 300 g for 5 min The supernatant is removed and the cells were re-suspended in wash buffer (0.1% BSA in PBS/azide). The samples were re-centrifuged, the supernatant removed, and the cells re-suspended in 0.5 ml of 0.5% para-formaldehyde overnight prior to analysis using a BD-LSR flow cytometer. The conjugates were detected by measuring the dual staining CD61 and CD15 in the neutrophil zone. The shift in FITC labeling indicates if more platelets have migrated in the neutrophil region. Monocyte-Platelet Aggregates (FITC labeled CD61, and PE labeled CD14): For monocyte labeling, the staining procedure and sample processing is the same as that developed for neutrophils except that the cell identification marker is the selective monocytes marker, FITC labeled CD61. Methods for the CD14 marker are the same. The method for evaluating the conjugates is the same as described above.

Figure 33:
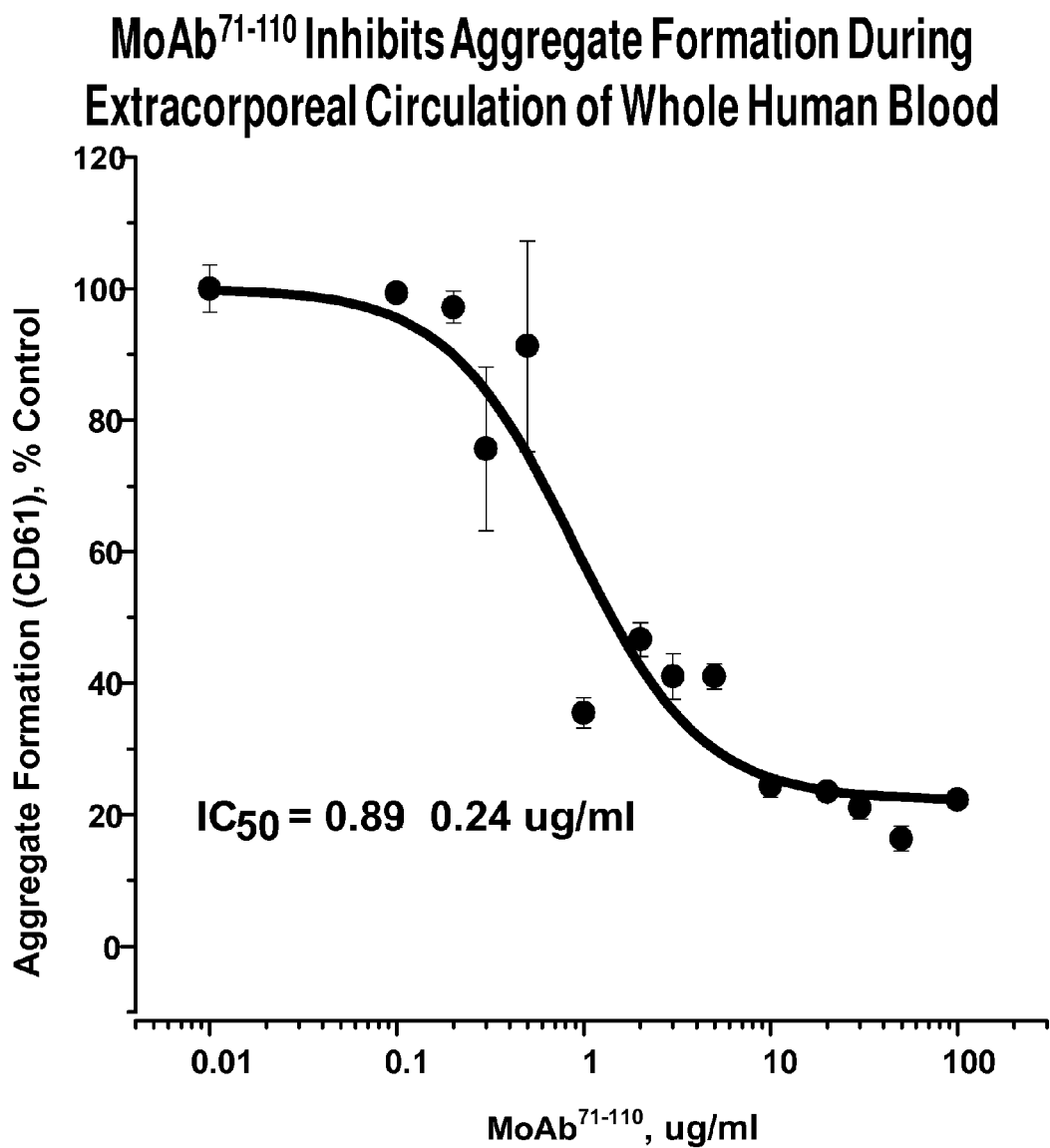
FIG. 33 illustrates MoAb$^{71-110}$ inhibits aggregate formation during extracorporeal circulation of whole human blood. Because of platelet activation, platelets bind to other platelets and leukocytes to form cellular aggregates. The presence of aggregates has been demonstrated to lead to an increased likelihood of heart attack. During the extracorporeal circulation, inhibition aggregate formation was measured by evaluating the presence of platelets in the leukocyte populations as described in example 14. Treatment with MoAb$^{71-110}$ completely inhibits aggregate dose dependently with complete inhibition observed at ~10 μg/ml.

FIG. 33 demonstrates the inhibition of aggregate formation with the treatment of MoAb$^{71-110}$ (0.5-100 ug/ml). MoAb$^{71-110}$ completely inhibits aggregate formation at ~10 ug/ml, which is consistent with previous results.

Example 16

Inhibition of TNF-Alpha Formation by MoAb$^{71-110}$ Following Extracorporeal Circulation TNF-Alpha is a potent inflammatory cytokine that has been implicated in several disease pathologies. TNF-alpha is pro-inflammatory cytokine that recruits other inflammatory mediators to exacerbate the inflammatory response. TNF-alpha inhibition is a key marker for inhibition of inflammatory responses. Using the tubing loop methods described in the previous examples, the MoAb$^{71-110}$ treated blood samples were spun down for plasma and evaluated with a TNF ELISA (BD-Biosciences).

In brief, polystyrene microtiter plates were coated with 50 µl of 1:100 diluted capture antibody overnight at 4° C. The wells were aspirated and blocked with 1% BSA/PBS solution for 1-hour. The wells were aspirated and incubated with 100 µl of tubing loop plasma. The plasma was incubated at room temperature for 1-hour. The wells were aspirated and washed with PBS 5 times. 100 µl of biotin labeled detection antibody diluted 1:200 in 1% BSA/PBS was added to each well and incubated for 1 hour at room temperature. The wells were aspirated and incubated with 100 µl Streptavidin-HRPO conjugate for 1-hour at room temperature. The wells were aspirated and washed with PBS 5 times and developed with TMB. The reaction was stopped with 100 µl of 1M phosphoric acid and the plate read at 450 nm with a microplate reader.

Figure 34:
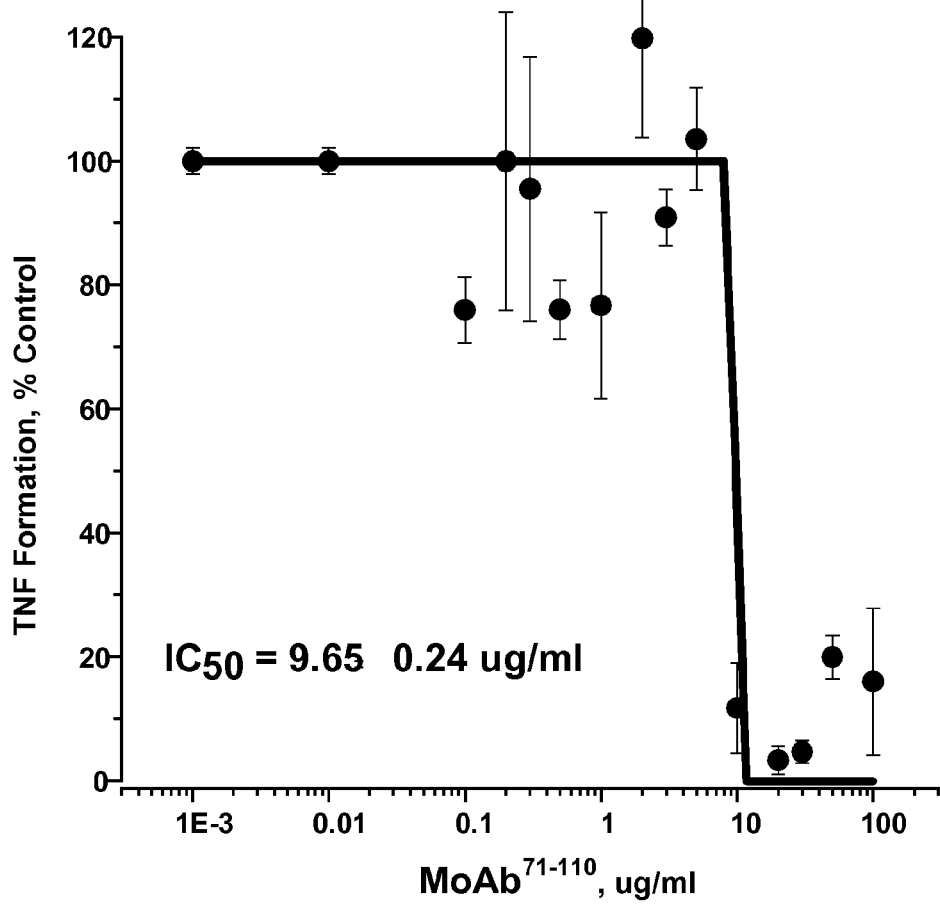
FIG. 34 illustrates MoAb$^{71-110}$ inhibits TNF-alpha formation during extracorporeal circulation of whole human blood. TNF-Alpha release is considered a marker of monocyte activation. Monocytes are activated by the anaphylatoxins C3a and C5a. To measure the effect of MoAb$^{71-110}$ on TNF-alpha formation, tubing loop plasma samples were evaluated in a sandwich ELISA assay. As shown, MoAb$^{71-110}$ dose dependently inhibited TNF-alpha formation with complete inhibition observed at ~10 μg/ml.

As demonstrated by FIG. 8, treatment of tubing loop samples with MoAb$^{71-110}$ (0.5-100 ug/ml) demonstrates dose dependent inhibition with complete inhibition observed at about 10 ug/ml. This number coincides with the results of the other assays as well as the dose for complete monocyte inhibition seen in FIG. 34.

Example 17

Reduction of Free Properdin Levels by MoAb$^{71-110}$

Anti-properdin monoclonal antibody of the present invention is capable of lowering the levels of free properdin in plasma treated with the monoclonal antibody of the invention. Following the tubing loop model, plasma samples were evaluated for the presence of free properdin. The rotated controls show high levels of properdin levels. The amount of free properdin in solution is reduced upon treatment with the monoclonal antibody of the invention.

ELISA plates were coated with a purified polyclonal antibody at a dilution ratio of 2 µg/50 µl/well. Following an overnight incubation at 4° C., the plate was treated with blocking solution (1% BSA in PBS). After removing the blocking solution, the plate was incubated with the plasma samples from the tubing loop model. And samples were incubated for 1 hour at room temperature. Following a thorough rise with PBS, wells were incubated with biotin labeled MoAb$^{71-110}$ (1:1000 dilution in blocking solution). The bound labeled antibody was detected with peroxidase conjugated neutravidin (pierce) for 1 hour. The color was developed with TMB substrate.

Figure 35:
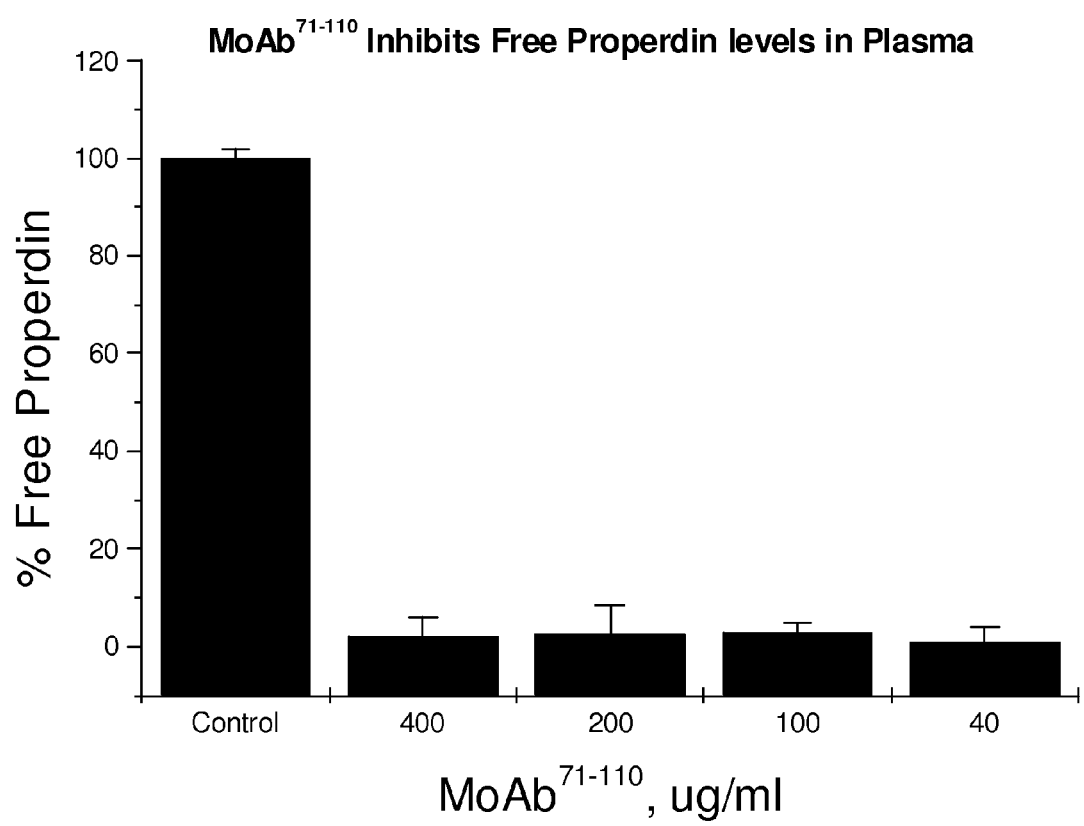
FIG. 35 illustrates MoAb$^{71-110}$ reduces levels of free properdin in plasma. ELISA wells were coated with a polyclonal antibody at 2 μg/50 μl per well. The serum containing various concentrations of anti-properdin monoclonal antibody$^{71-110}$ were added. The plate was incubated with biotinylated MoAb$^{71-110}$. The results show that MoAb$^{71-110}$ treatment reduced the levels of free properdin in plasma.

As shown in FIG. 35, the monoclonal antibody of the invention reduces the levels of free properdin.

Example 18

MoAb $^{71-110}$ Inhibits Release of Neutrophil Elastase During Whole Blood Extracorporeal Circulation Neutrophil elastase is a potent mediator of the inflammatory response that is released when neutrophils are activated, either via complement-mediated mechanisms of non-complement mediated mechanisms. Regardless of the mechanism of activation, neutrophil elastase is released and results in many deleterious effects.

We demonstrate that MoAb$^{71-110}$ can down-regulate release of neutrophil elastase by inhibiting complement-mediated activation of neutrophils. We used the tubing-loop model as described above to cause complement activation in blood and demonstrate inhibition by the antibody. In order to demonstrate inhibition of neutrophil elastase, a polystyrene microtiter plate (Corning) was coated with 50 µl of a 1:500 dilution of neutrophil elastase capture antibody (The Binding Site) overnight at 4° C. The following day, the wells were aspirated and blocked with 1% BSA/PBS solution for 2-hours. After blocking, the wells were incubated with 100 µl of tubing loop plasma samples diluted to 1:25 in AP buffer. Following 2-hour incubation at room temperature, the wells were aspirated and washed with 200 µl PBS five times. The wells were then incubated with 100 µl of Sheep Anti-Human Alpha-1Trypsin peroxidase conjugated antibody (The Binding Site) for 1-hour at room temperature. The wells were aspirated and washed with 200 µl PBS five times. The plate was developed and analyzed using standard ELISA methods described above.

Figure 36:
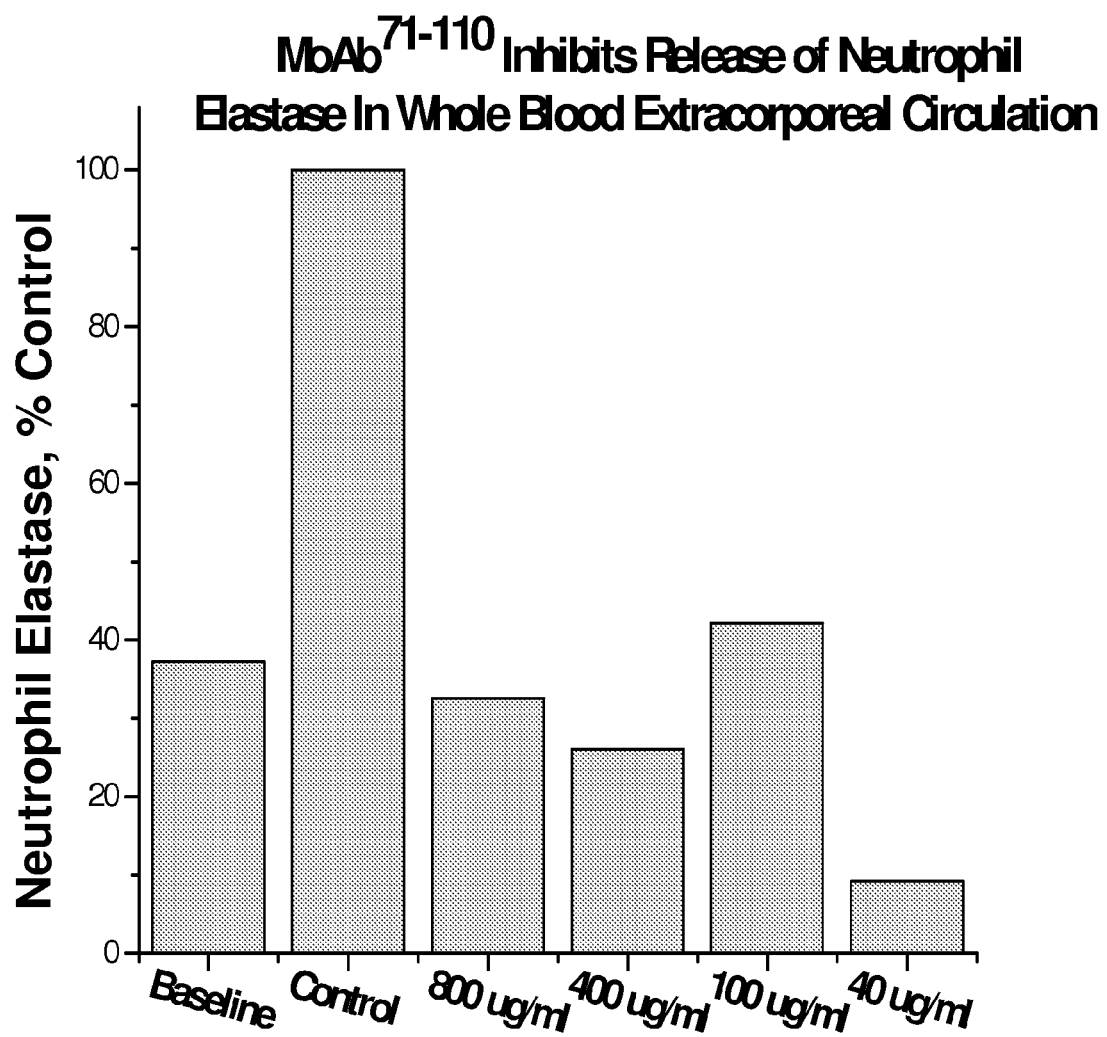
FIG. 36 illustrates MoAb$^{71-110}$ inhibits release of neutrophil elastase in whole blood extracorporeal circulation. Neutrophil elastase is a deleterious inflammatory component that is released during activation of complement. Tubing loop samples treated with MoAb$^{71-110}$ were measured using an in-house Elastase assay. The figure demonstrates that complement inhibition with MoAb$^{71-110}$ inhibits neutrophil activation and thus neutrophil elastase.

FIG. 36 demonstrates inhibition of Neutrophil Elastase release at various concentration of the antibody. Inhibition is observed at low concentrations of the antibody.

Example 19

MoAb $^{71-110}$ Inhibits Release of TNF-Alpha During Whole Blood Extracorporeal Circulation TNF-Alpha is a key inflammatory cytokine involved in inflammation. It is potent cytokine that is responsible for generating several downstream inflammatory components that exacerbate the inflammatory response.

MoAb$^{71-110}$ effectively down-regulates the generation and release of TNF-Alpha that is resultant of complement activation. MoAb $^{71-110}$ inhibits the alternative pathway upstream and inhibits anaphylatoxin-mediated activation of monocytes, the cells mainly responsible for generating TNF-alpha. We used tubing loop samples that have undergone complement activation to demonstrate that MoAb$^{71-110}$ inhibits the production of TNF-alpha. Polystyrene microtiter plates were coated with 100-µl TNF capture antibody (BD Biosciences) at 1:100 dilution in PBS. The plate was incubated overnight at 4° C. The following day the wells were aspirated and blocked for 2-hours with 1% BSA/PBS solution. Following blocking, the wells were incubated with undiluted tubing loop plasma samples. Following 2-hour incubation at room temperature, the wells were aspirated and washed 5 times with 200 µl PBS. The captured TNF-alpha was detected using a biotinylated TNF-alpha detection antibody (BD Biosciences) at 1:1000 dilution in 1% BSA/PBS. The plate was incubated for 1-hour at room temperature and processed following standard ELISA methods described above.

Figure 37:
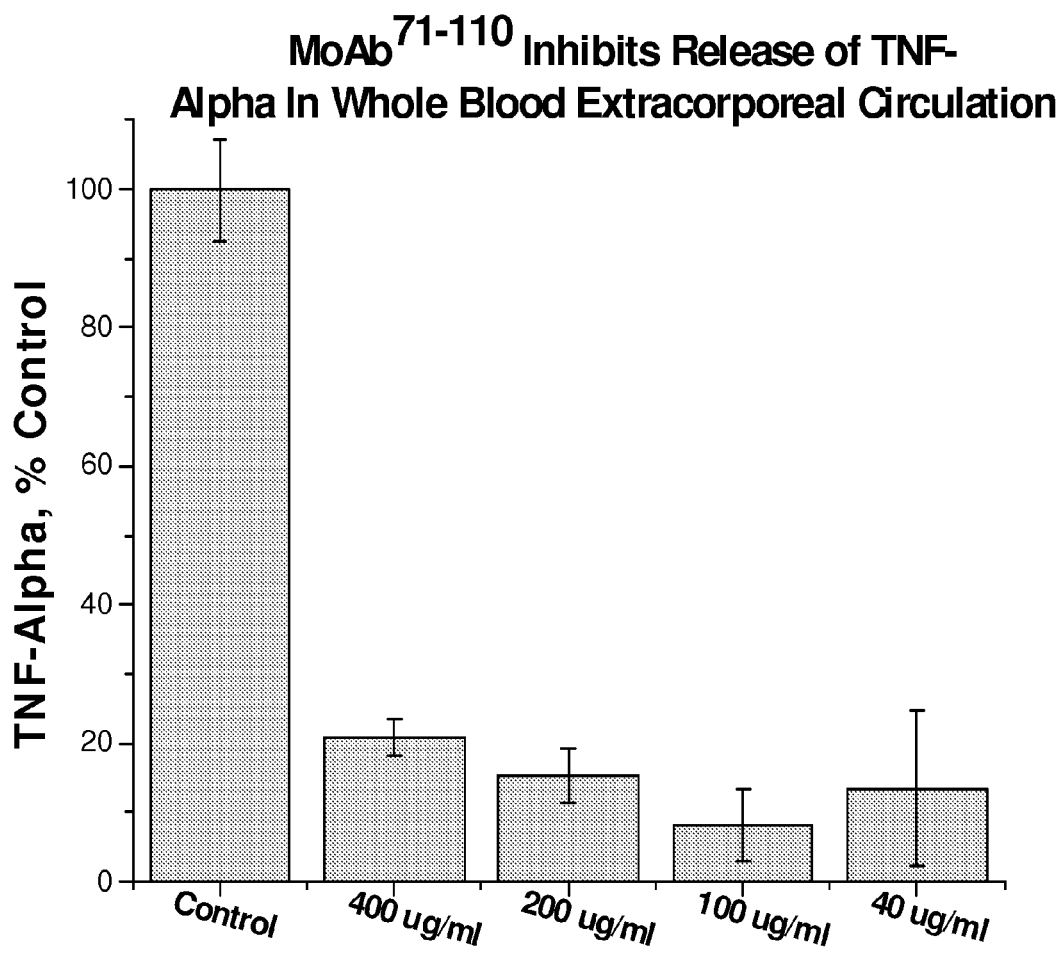
FIG. 37 illustrates MoAb$^{71-110}$ inhibits release of TNF-alpha in whole blood extracorporeal circulation. TNF-alpha is the most potent inflammatory cytokine released during an inflammatory response. It is implicated in several disease indications and is primarily response for exacerbating an inflammatory response. TNF-alpha is released when monocytes are activated. We evaluated the generation of TNF-alpha during extracorporeal circulation and whether MoAb$^{71-110}$ can inhibit that generation. The figure demonstrates that complement inhibition with MoAb$^{71-110}$ inhibits monocyte activation and thus TNF-alpha.

FIG. 37 demonstrates significant inhibition of TNF-alpha by MoAb$^{71-110}$ compared to untreated controls. This inhibition is observed at all tested concentrations. FIG. 35 also demonstrates inhibition of TNF alpha production by monocytes in the extra corporeal model of circulation.

Example 20

MoAb)$^{71-110}$ and IgG, F(ab)2, and F(ab) Inhibits C5b-9 Formation in Erythrocyte Hemolysis Assay Following Whole Blood Extracorporeal Circulation The effect of IgG, F(ab)2, and Fab was evaluated in an alternative pathway dependent hemolysis assay using rabbit erythrocytes and normal human serum. Erythrocyte surface activates alternative complement pathway in normal human serum. As a result, C5b-9 is formed on the surface of the erythrocytes, causing cellular lysis. The assay measures inhibition of erythrocyte lysis as a function of time.

Methods for lysis assay is described in examples above. In this experiment the final concentration of the monoclonal antibody would be 40 µg/ml. We compared IgG, F(ab)2, and Fab to determine the inhibitory ability of the intact antibody and its fragments.

It was found that all three are equally potent in inhibiting the alternative pathway dependent hemolysis.

Example 21

Therapeutic Claim Evaluation of Complement Activity in Rabbits Administered with Various Doses of MoAb$^{71-110}$ White New Zealand Rabbits were dosed intravenously with MoAb$^{71-110}$ at 5.04 mg/Kg, 1.41 mg/kg, 0.54 mg/kg, and 0.05 mg/kg in saline solution. Following the i.v. dosing, blood samples were drawn via central artery in the ear. After 10-minute incubation at room temperature, the samples were centrifuged to remove the clot. The sera were frozen at −80° C. until used. Rabbit serum taken at various time points over a course of 105 hours were subjected to a typical AP dependent rRBC hemolysis using standard methods. Kinetic runs were generated at each rabbit serum concentration. The endpoint kinetic readings were plotted versus time to generate the FIG. 38. Correspondingly, samples were also evaluated in a C3b-properdin assay to determine the effect of MoAb$^{71-110}$ in preventing properdin association with C3b as shown in FIG. 39. The results in FIG. 39 parallel the results shown in FIG. 38.

Figure 38:
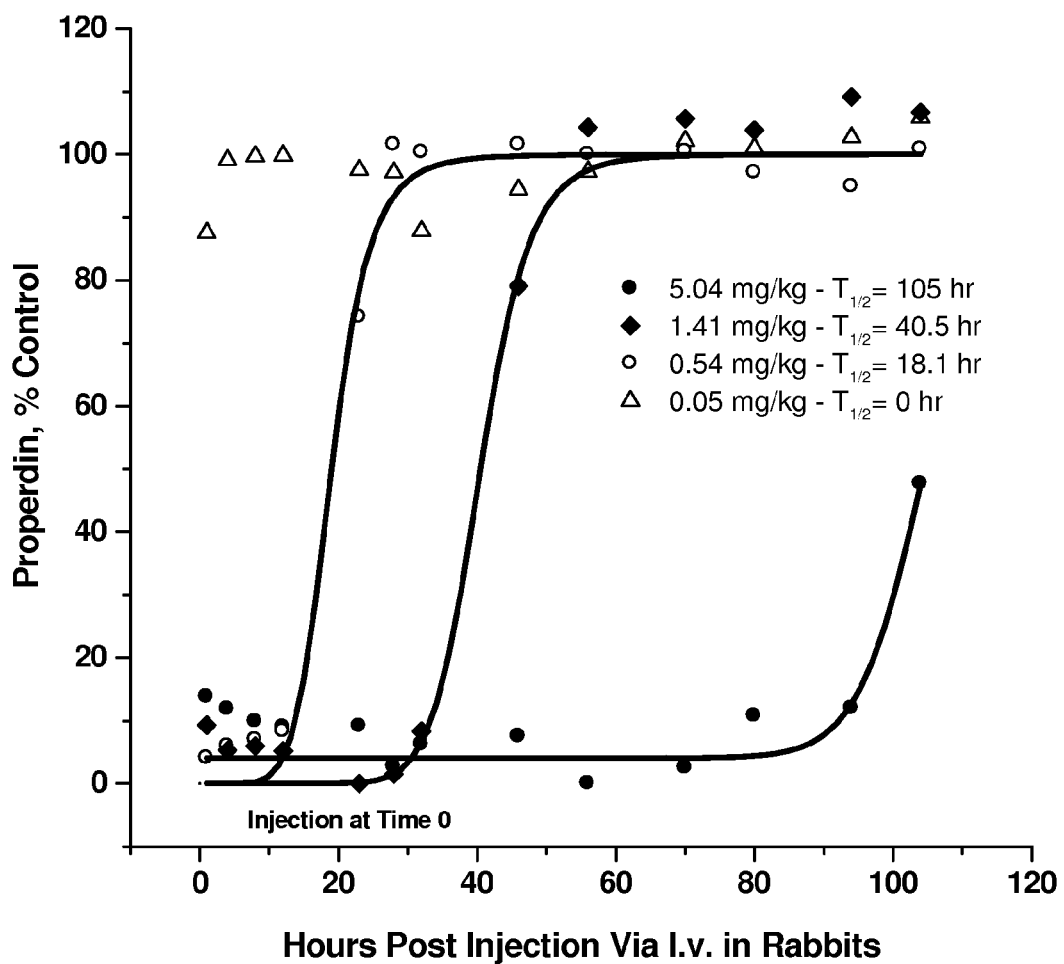
FIG. 38 illustrates a plot of the pharmacodynamics of MoAb$^{71-110}$ in rabbits evaluation of AP activity in serum.
Figure 39:
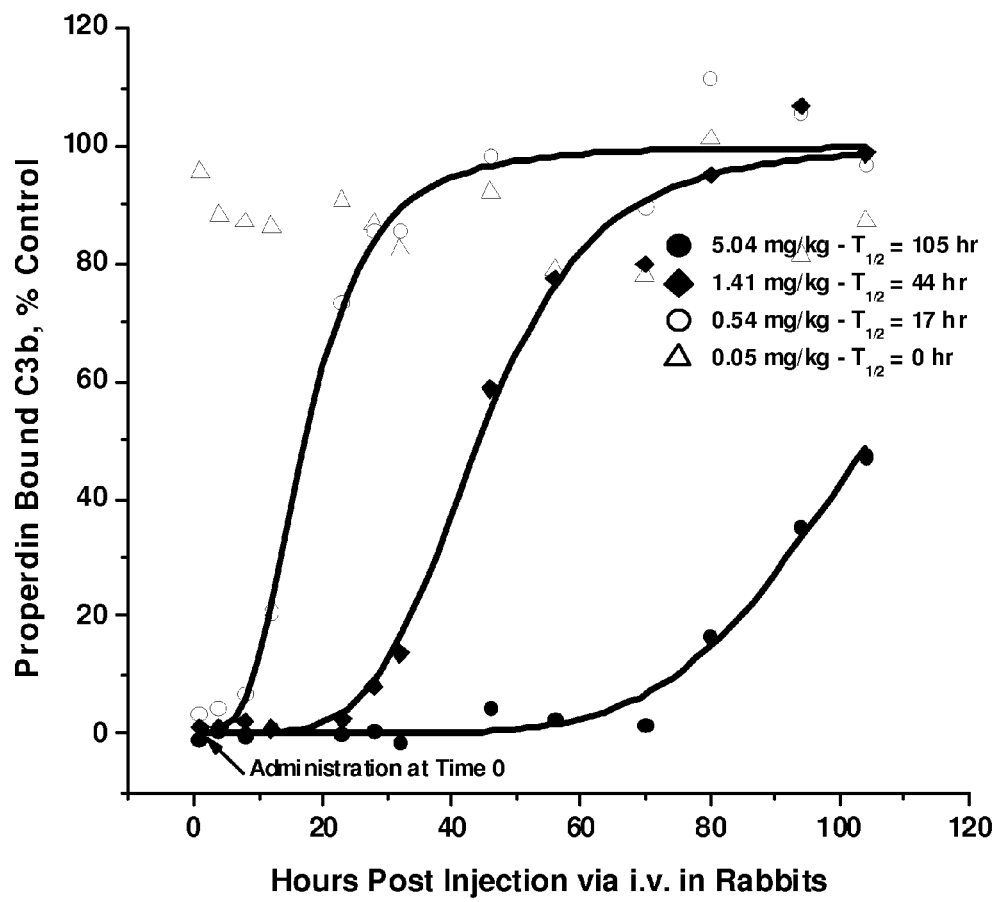
FIG. 39 illustrates a plot of the pharmacodynamics of MoAb$^{71-110}$ in rabbits evaluation of free properdin in serum rate of properdin synthesis.
Figure 40:
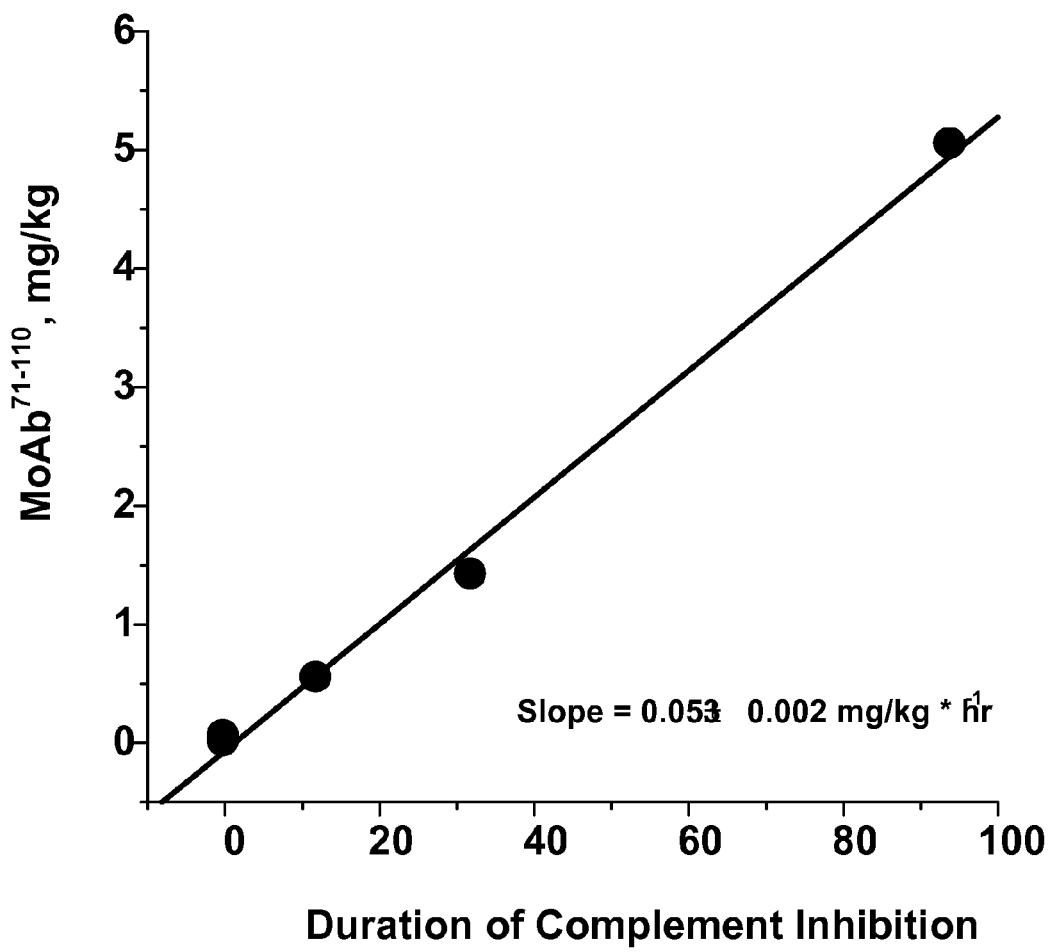
FIG. 40 illustrates a plot of the duration of complement activity is linearly proportional to the concentration of MoAb$^{71-110}$.

Results from FIGS. 38 and 39 were used in evaluating the effect of MoAb$^{71-110}$ on the duration of complement activity. The inhibition of complement activity in rabbits is linearly proportional to the dose of MoAb$^{71-110}$. FIG. 40 shows the therapeutic effect of MoAb$^{71-110}$ on complement activity in rabbits. Complement activity is inhibited at a rate of 0.05 mg/kg per hour. As shown 1 mg/kg dose is effective for a 20-hour period. Thus therapeutic efficacy is determined based on the dose and thus can be easily monitored for a given use. The dose of MoAb$^{71-110}$ can be easily predicted based on the graph shown in FIG. 40.

Figure 41:
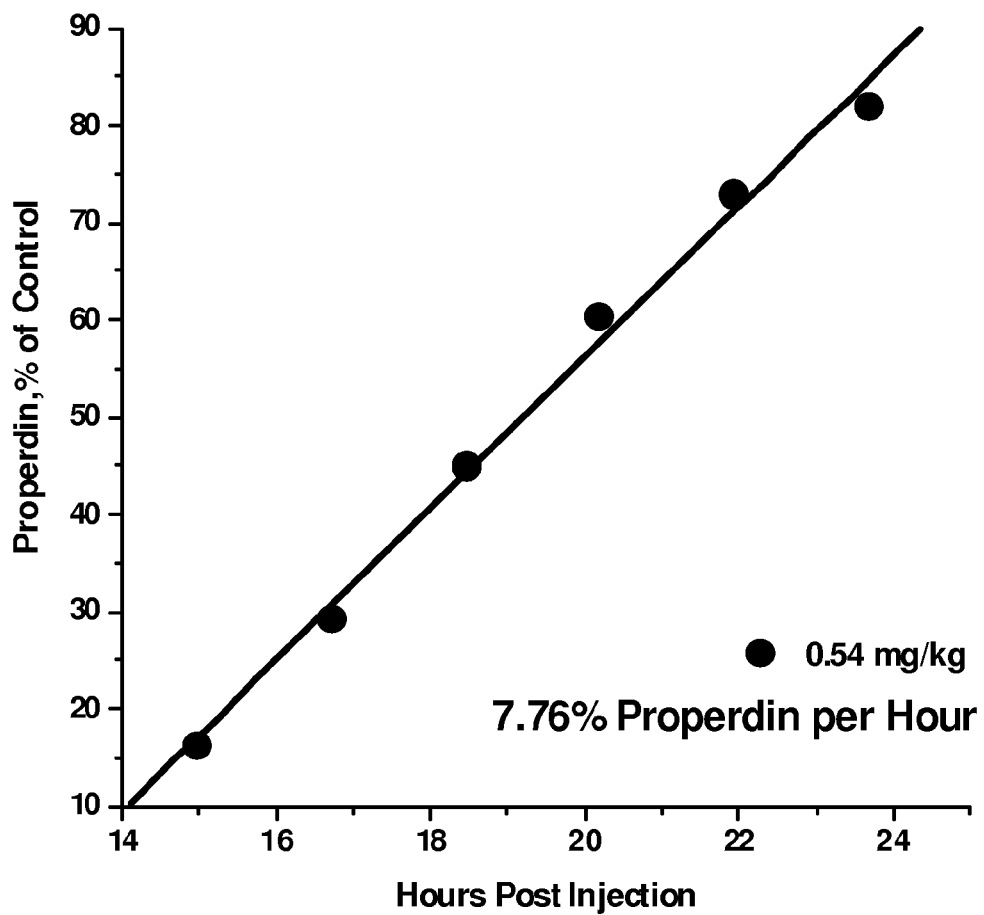
FIG. 41 illustrates a plot of the rate of properdin biosynthesis in rabbits administered i.v. a bolus of MoAb$^{71-110}$. Return of AP activity with properdin synthesis is at a dose of 0.54 mg/kg.
Figure 42:
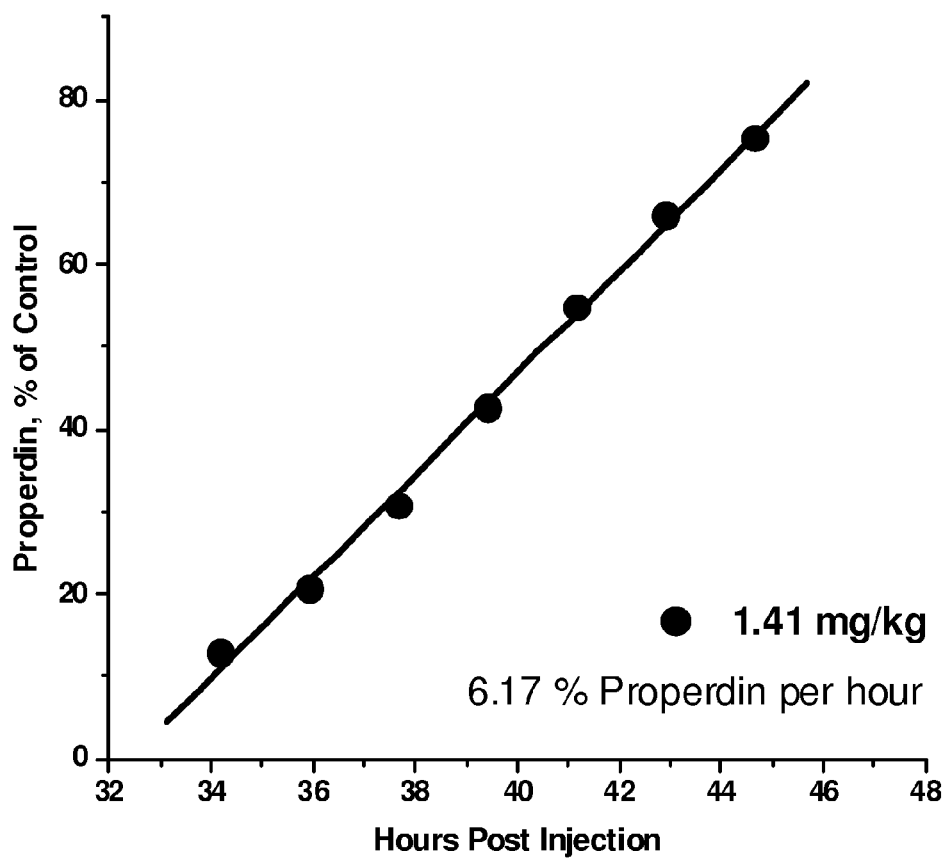
FIG. 42 illustrates a plot of the rate of properdin biosynthesis in rabbits administered i.v. a bolus MoAb$^{71-110}$. Return of AP activity with properdin synthesis is at a dose of 1.41 mg/kg.

FIG. 39 shows that levels of properdin return to normal after the effect of the drug is gone, where the effect of the drug is measured in terms of inhibition of complement activity. As shown in FIGS. 38 and 39, the slope of the return of complement activity and properdin at each dose in rabbits give very similar slope. Rate of properdin synthesis appear to be consistent for each of the three higher doses used. The rate of synthesis was calculated based on the percentage synthesis per hour. FIGS. 41 and 42 show that the rate of properdin synthesis following the diminution of inhibition of complement activity is 6-7% per hour. Within 15-20 hours after the effects of the drug, the properdin concentration returns to normal.

Figure 43:
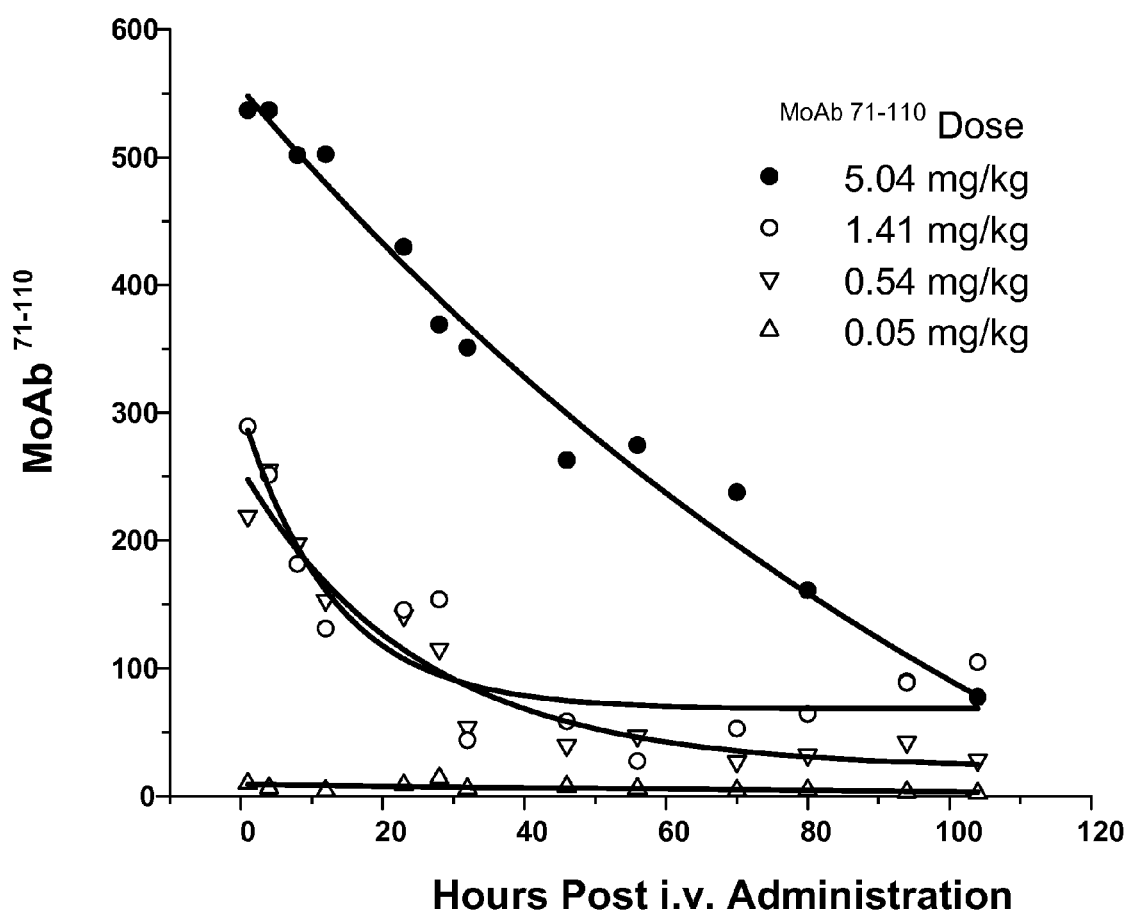
FIG. 43 illustrates a plot of the kinetics of MoAb$^{71-110}$ disappearance in rabbit serum as a function of time.

FIG. 43 shows the kinetics of MoAb$^{71-110}$ consumption as a function of time. MoAb$^{71-110}$ at all three highest concentrations show an exponential decay with time. Only 100 nM antibody remains at the end of 100 hours in rabbits administered 5 mg/kg dose of MoAb$^{71-110}$. The level of MoAb$^{71-110}$ at 100 nM (plus minus 20 nM) causes inhibition. If the MoAb$^{71-110}$ concentration falls below that level, complement activity will not be inhibited.

Example 22

MoAb$^{71-110}$ does not Inhibit the Classical Pathway Dependent Formation of C4d This assay evaluates the ability of MoAb$^{71-110}$ to inhibit the formation of C4d in a classical pathway setting. C4d is a component of the classical pathway C3 convertase. Polystyrene microtiter wells were coated with 50 µl of 1% Ovalbumin in PBS and incubated overnight at 4° C. The wells were aspirated and blocked with 300 µl of 1% BSA in PBS for 1-hour at room temperature. The wells were aspirated again and each well was incubated with 50 µl of 1:1000 diluted anti-ovalbumin antibody in 1% BSA/PBS. The plate was incubated for 1 hour at room temperature. The wells were aspirated and rinsed with PBS five times. Various concentrations of MoAb$^{71-110}$ were aliquoted into 2% human serum diluted in gelatin veronal buffer (GVB with calcium and Magnesium 5 mM each). Serum concentrations were optimized in previous assays. A 100 µl aliquot of the solution was incubated onto the respective wells and incubated at 37° C. for 2-hours. The wells were aspirated and rinsed five times with PBS. 50 μl of peroxidase conjugated anti-C4d antibody (1:2000 dilution) was added to each well and incubated at room temperature for 1-hour. The plate was aspirated and rinsed thoroughly with PBS, and 100 μl of 3,3',5,5'-tetramethyl benzidine (TMB) substrate was added. After incubation for 30 minutes at 25° C. The reaction of TMB was quenched by the addition of 100 μl of phosphoric acid, and the plate was read at 450 nm in a microplate reader.

Figure 44:
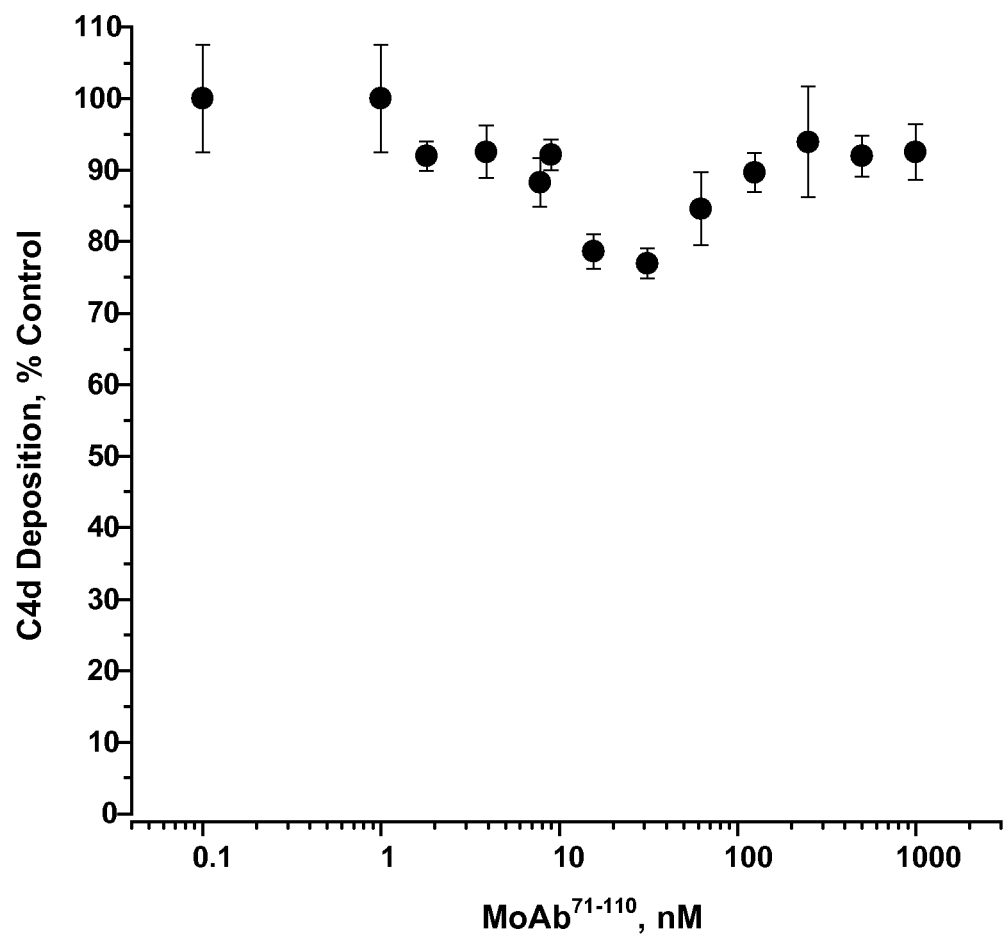
FIG. 44 illustrates a plot showing that MoAb$^{71-110}$ does not inhibit the classical pathway dependent formation of C4d.

FIG. 44 illustrates a plot showing that MoAb$^{71-110}$ does not inhibit the classical pathway dependent formation of C4d. The classical pathway is mediated via the presence of the antigen-antibody complex. The presence of the complexes causes the recruitment of C1 and C1q, which causes the cleavage of C4 into C4a and C4b, which then binds to C2a to form the C4b2a complex. This is the active classical pathway convertase, which then proceeds to cleave C3 to lead ultimately to the formation of C5b-9. As shown, MoAb$^{71-110}$ does not inhibit the C4d formation at concentrations used.

What has been described above includes examples and implementations of the present invention. Because it is not possible to describe every conceivable combination of components, circuitry or methodologies for purposes of describing the present invention, one of ordinary skill in the art will recognize that many further combinations and permutations of the present invention are possible. Accordingly, the present invention is intended to embrace all such alterations, modifications and variations that fall within the spirit and scope of the appended claims.

Having described the invention, the following is claimed:

1. A method of inhibiting alternative pathway activation in blood of a subject, the method comprising:

administering to blood of the subject a therapeutically effective amount of an antibody or fragment thereof that specifically binds to the amino acid sequence of SEQ ID NO: 2 of properdin and inhibits the alternative pathway activation without affecting the classical pathway activation.

2. The method of claim 1, wherein the antibody is a monoclonal antibody.

3. The method of claim 1, wherein the antibody is a chimeric, recombinant, humanized, de-immunized or fully human antibody.

4. The method of claim 1, wherein the subject has or is at risk of developing atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, macular degeneration, and combinations thereof.

5. The method of claim 1, wherein the antibody is administered in vivo or ex vivo.

6. The method of claim 1, wherein the antibody is produced by the hybridoma cell line deposited under ATCC Accession Number PTA-9019.

7. The method of claim 1, wherein the antibody or fragment thereof, binds to the same epitope on properdin as an antibody produced by the hybridoma cell line deposited under ATCC Accession Number PTA-9019.

8. The method of claim 1, wherein the antibody or fragment thereof comprises the murine variable regions of an antibody produced by the hybridoma cell line deposited under ATCC Accession Number PTA-9019 and human constant regions.

9. The method of claim 1, the antibody or fragment thereof, comprising:
a heavy chain variable domain that includes the amino acid sequences of the three CDRs in SEQ ID NO: 7, and
a light chain variable domain that includes the amino acid sequences of the three CDRs in SEQ ID NO: 8, wherein the antibody binds to human properdin.

10. The method of claim 1, the antibody or fragment thereof exhibiting at least one of the functional properties: the antibody inhibits properdin binding to C3b, the antibody reduces the formation of C3bB, the antibody reduces the formation of C3 convertase, the antibody reduces the production of C3a and C5a, the antibody reduces C5b-9 complex formation, the antibody reduces the activation of neutrophils, the antibody reduces the activation of monocytes, the antibody reduces the activation of platelets, or the antibody reduces the formation of leukocyte-platelet conjugates.

11. The method of claim 1, wherein the antibody or fragment thereof inhibits alternative pathway dependent rabbit erythrocyte lysis in human serum/plasma.

12. The method of claim 1, wherein the antibody or fragment thereof binds to properdin oligomers and promotes dissociation of the properdin oligomers to properdin monomers.

13. The method of claim 9, wherein the heavy chain variable regions CDR1, CDR2, and CDR3 comprise the amino acid sequences of SEQ ID NO: 9, 10, and 11, respectively.

14. The method of claim 9, wherein the light chain variable regions CDR1, CDR2, and CDR3 comprise the amino acid sequences of SEQ ID NO: 12, 13, and 14, respectively.

15. The method of claim 1, wherein the antibody or fragment thereof is a single chain antibody, IgG, F(ab)2, F(ab')2, F(ab) fragment, or truncated antibody.

16. The method of claim 1, wherein the antibody or fragment thereof lacks the ability to activate Fcγ receptors.

17. The method of claim 1, wherein the antibody or fragment thereof lacks immunogenicity in a human.

18. The method of claim 1, wherein the antibody or fragment thereof contains more than one antigen binding domain and binds antigen at a stoichiometry of 1:1.

19. The method of claim 1, wherein the subject has or is at risk of developing arthritis.

20. The method of claim 1, wherein the antibody or fragment thereof inhibits alternative pathway mediated formation of TNF alpha.

21. The method of claim 1, wherein the antibody or fragment thereof inhibits alternative pathway mediated release of TNF alpha.

22. The method of claim 1, wherein the antibody or fragment thereof inhibits alternative pathway mediated release of neutrophil elastase.

* * * * *

SEQUENCE LISTING

<160> NUMBER OF SEQ ID NOS: 14

<210> SEQ ID NO 1
<211> LENGTH: 469
<212> TYPE: PRT
<213> ORGANISM: Homo sapiens

<400> SEQUENCE: 1

Met Ile Thr Glu Gly Ala Gln Ala Pro Arg Leu Leu Leu Pro Pro Leu
1               5                   10                  15

Leu Leu Leu Leu Thr Leu Pro Ala Thr Gly Ser Asp Pro Val Leu Cys
                20                  25                  30

Phe Thr Gln Tyr Glu Glu Ser Ser Gly Lys Cys Lys Gly Leu Leu Gly
            35                  40                  45

Gly Gly Val Ser Val Glu Asp Cys Cys Leu Asn Thr Ala Phe Ala Tyr
        50                  55                  60

Gln Lys Arg Ser Gly Gly Leu Cys Gln Pro Cys Arg Ser Pro Arg Trp
65                  70                  75                  80

Ser Leu Trp Ser Thr Trp Ala Pro Cys Ser Val Thr Cys Ser Glu Gly
                85                  90                  95

Ser Gln Leu Arg Tyr Arg Arg Cys Val Gly Trp Asn Gly Gln Cys Ser
                100                 105                 110

Gly Lys Val Ala Pro Gly Thr Leu Glu Trp Gln Leu Gln Ala Cys Glu
            115                 120                 125

Asp Gln Gln Cys Cys Pro Glu Met Gly Gly Trp Ser Gly Trp Gly Pro
        130                 135                 140

Trp Glu Pro Cys Ser Val Thr Cys Ser Lys Gly Thr Arg Thr Arg Arg
145                 150                 155                 160

Arg Ala Cys Asn His Pro Ala Pro Lys Cys Gly Gly His Cys Pro Gly
                165                 170                 175

Gln Ala Gln Glu Ser Glu Ala Cys Asp Thr Gln Gln Val Cys Pro Thr
            180                 185                 190

His Gly Ala Trp Ala Thr Trp Gly Pro Trp Thr Pro Cys Ser Ala Ser
        195                 200                 205

Cys His Gly Gly Pro His Glu Pro Lys Glu Thr Arg Ser Arg Lys Cys
    210                 215                 220

Ser Ala Pro Glu Pro Ser Gln Lys Pro Pro Gly Lys Pro Cys Pro Gly
225                 230                 235                 240

Leu Ala Tyr Glu Gln Arg Arg Cys Thr Gly Leu Pro Pro Cys Pro Val
                245                 250                 255

```
Ala Gly Gly Trp Gly Pro Trp Gly Pro Val Ser Pro Cys Pro Val Thr
            260                 265                 270

Cys Gly Leu Gly Gln Thr Met Glu Gln Arg Thr Cys Asn His Pro Val
        275                 280                 285

Pro Gln His Gly Gly Pro Phe Cys Ala Gly Asp Ala Thr Arg Thr His
    290                 295                 300

Ile Cys Asn Thr Ala Val Pro Cys Pro Val Asp Gly Glu Trp Asp Ser
305                 310                 315                 320

Trp Gly Glu Trp Ser Pro Cys Ile Arg Arg Asn Met Lys Ser Ile Ser
                325                 330                 335

Cys Gln Glu Ile Pro Gly Gln Gln Ser Arg Gly Arg Thr Cys Arg Gly
            340                 345                 350

Arg Lys Phe Asp Gly His Arg Cys Ala Gly Gln Gln Gln Asp Ile Arg
        355                 360                 365

His Cys Tyr Ser Ile Gln His Cys Pro Leu Lys Gly Ser Trp Ser Glu
    370                 375                 380

Trp Ser Thr Trp Gly Leu Cys Met Pro Pro Cys Gly Pro Asn Pro Thr
385                 390                 395                 400

Arg Ala Arg Gln Arg Leu Cys Thr Pro Leu Leu Pro Lys Tyr Pro Pro
                405                 410                 415

Thr Val Ser Met Val Glu Gly Gln Gly Glu Lys Asn Val Thr Phe Trp
            420                 425                 430

Gly Arg Pro Leu Pro Arg Cys Glu Glu Leu Gln Gly Gln Lys Leu Val
        435                 440                 445

Val Glu Glu Lys Arg Pro Cys Leu His Val Pro Ala Cys Lys Asp Pro
    450                 455                 460

Glu Glu Glu Glu Leu
465

<210> SEQ ID NO 2
<211> LENGTH: 40
<212> TYPE: PRT
<213> ORGANISM: Homo sapiens

<400> SEQUENCE: 2

Leu Cys Gln Pro Cys Arg Ser Pro Arg Trp Ser Leu Trp Ser Thr Trp
1               5                   10                  15

Ala Pro Cys Ser Val Thr Cys Ser Glu Gly Ser Gln Leu Arg Tyr Arg
            20                  25                  30

Arg Cys Val Gly Trp Asn Gly Gln
        35                  40

<210> SEQ ID NO 3
<211> LENGTH: 114
<212> TYPE: PRT
<213> ORGANISM: Homo sapiens

<400> SEQUENCE: 3

Thr Leu Pro Ala Thr Gly Ser Asp Pro Val Leu Cys Phe Thr Gln Tyr
1               5                   10                  15

Glu Glu Ser Ser Gly Lys Cys Lys Gly Leu Leu Gly Gly Gly Val Ser
            20                  25                  30

Val Glu Asp Cys Cys Leu Asn Thr Ala Phe Ala Tyr Gln Lys Arg Ser
        35                  40                  45

Gly Gly Leu Cys Gln Pro Cys Arg Ser Pro Arg Trp Ser Leu Trp Ser
    50                  55                  60
```

-continued

```
Thr Trp Ala Pro Cys Ser Val Thr Cys Ser Glu Gly Ser Gln Leu Arg
 65                  70                  75                  80

Tyr Arg Arg Cys Val Gly Trp Asn Gly Gln Cys Ser Gly Lys Val Ala
                 85                  90                  95

Pro Gly Thr Leu Glu Trp Gln Leu Gln Ala Cys Glu Asp Gln Gln Cys
            100                 105                 110

Cys Pro

<210> SEQ ID NO 4
<211> LENGTH: 10
<212> TYPE: PRT
<213> ORGANISM: Homo sapiens

<400> SEQUENCE: 4

Cys Arg Ser Pro Arg Trp Ser Leu Trp Ser
  1               5                  10

<210> SEQ ID NO 5
<211> LENGTH: 10
<212> TYPE: PRT
<213> ORGANISM: Homo sapiens

<400> SEQUENCE: 5

Arg Tyr Arg Arg Cys Val Gly Trp Asn Gly
  1               5                  10

<210> SEQ ID NO 6
<211> LENGTH: 10
<212> TYPE: PRT
<213> ORGANISM: Homo sapiens

<400> SEQUENCE: 6

Gln Arg Arg Cys Thr Gly Leu Pro Pro Cys
  1               5                  10

<210> SEQ ID NO 7
<211> LENGTH: 151
<212> TYPE: PRT
<213> ORGANISM: Artificial Sequence
<220> FEATURE:
<223> OTHER INFORMATION: Vh amino acid sequence of MoAb71-110

<400> SEQUENCE: 7

Leu Asn Met Glu Arg His Trp Ile Phe Leu Phe Leu Leu Ser Val Thr
  1               5                  10                  15

Ala Gly Val His Ser Gln Val Leu Leu Gln Gln Ser Ala Pro Glu Leu
                 20                  25                  30

Ala Arg Pro Gly Ala Ser Val Lys Met Ser Cys Thr Ala Ser Gly Tyr
             35                  40                  45

Ile Phe Thr Asn Tyr Pro Ile His Trp Val Lys Gln Arg Pro Gly Gln
         50                  55                  60

Gly Leu Glu Trp Ile Gly Phe Ile Asp Pro Gly Gly Tyr Asp Glu
 65                  70                  75                  80

Pro Asp Glu Arg Phe Arg Asp Arg Ala Thr Leu Thr Ala Asp Lys Ser
                 85                  90                  95

Ser Ser Thr Ala Tyr Met Gln Leu Ser Ser Leu Thr Ser Glu Asp Ser
            100                 105                 110

Ala Ile Tyr Tyr Cys Ala Arg Arg Gly Gly Gly Tyr Tyr Leu Asp Tyr
        115                 120                 125
```

-continued

Trp Gly Gln Asp Thr Thr Leu Thr Val Ser Ala Ala Ser Thr Thr Pro
    130                 135                 140

Pro Ser Val Lys Gly Glu Phe
145                 150

<210> SEQ ID NO 8
<211> LENGTH: 156
<212> TYPE: PRT
<213> ORGANISM: Artificial Sequence
<220> FEATURE:
<223> OTHER INFORMATION: VL amino acid sequence of MoAb71-110

<400> SEQUENCE: 8

Lys Glu Ile His Gln Ala Gly Lys Gly Ile Lys Met Lys Ser Gln Thr
1               5                   10                  15

Gln Val Phe Val Phe Leu Leu Leu Cys Val Ser Gly Ala His Gly Ser
            20                  25                  30

Ile Val Met Thr Gln Thr Pro Lys Phe Leu Leu Val Ser Ala Gly Asp
        35                  40                  45

Arg Ile Thr Ile Thr Cys Lys Ala Ser Gln Ser Val Asn Asn Asp Val
    50                  55                  60

Ala Trp Tyr Gln Gln Lys Pro Gly Gln Ser Pro Lys Leu Leu Ile Tyr
65                  70                  75                  80

Tyr Ala Ser Asn Arg Tyr Thr Gly Val Pro Asp Arg Phe Thr Gly Ser
                85                  90                  95

Gly Tyr Gly Thr Asp Phe Thr Phe Thr Ile Thr Thr Val Lys Ala Glu
            100                 105                 110

Asp Leu Ala Val Tyr Phe Cys Gln Gln Asp Tyr Ser Ser Pro Leu Thr
        115                 120                 125

Phe Gly Ala Gly Thr Lys Leu Glu Leu Lys Arg Ala Asp Ala Ala Pro
    130                 135                 140

Thr Val Ser Ala Cys Thr Lys Gly Glu Phe Ala Ala
145                 150                 155

<210> SEQ ID NO 9
<211> LENGTH: 16
<212> TYPE: PRT
<213> ORGANISM: Artificial Sequence
<220> FEATURE:
<223> OTHER INFORMATION: CDR1 of Vh

<400> SEQUENCE: 9

Cys Thr Ala Ser Gly Tyr Ile Phe Thr Asn Tyr Pro Ile His Trp Val
1               5                   10                  15

<210> SEQ ID NO 10
<211> LENGTH: 25
<212> TYPE: PRT
<213> ORGANISM: Artificial Sequence
<220> FEATURE:
<223> OTHER INFORMATION: Vh CDR2

<400> SEQUENCE: 10

Leu Glu Trp Ile Gly Phe Ile Asp Pro Gly Gly Gly Tyr Asp Glu Pro
1               5                   10                  15

Asp Glu Arg Phe Arg Asp Arg Ala Thr
            20                  25

<210> SEQ ID NO 11
<211> LENGTH: 16
<212> TYPE: PRT
<213> ORGANISM: Artificial Sequence -continued

```
<220> FEATURE:
<223> OTHER INFORMATION: Vh CDR3

<400> SEQUENCE: 11

Cys Ala Arg Arg Gly Gly Gly Tyr Tyr Leu Asp Tyr Trp Gln Asp
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Vl CDR1

<400> SEQUENCE: 12

Cys Lys Ala Ser Gln Ser Val Asn Asn Asp Val Ala Trp Tyr Gln
1               5                   10                  15

<210> SEQ ID NO 13
<211> LENGTH: 9
<212> TYPE: PRT
<213> ORGANISM: Artificial Sequence
<220> FEATURE:
<223> OTHER INFORMATION: VL CDR2

<400> SEQUENCE: 13

Ile Tyr Tyr Ala Ser Asn Arg Tyr Thr
1               5

<210> SEQ ID NO 14
<211> LENGTH: 14
<212> TYPE: PRT
<213> ORGANISM: Artificial Sequence
<220> FEATURE:
<223> OTHER INFORMATION: VL CDR3

<400> SEQUENCE: 14

Cys Gln Gln Asp Tyr Ser Ser Pro Leu Thr Phe Gly Ala Gly
1               5                   10
```